(12) United States Patent
Bilodeau et al.

(10) Patent No.: US 9,403,858 B2
(45) Date of Patent: Aug. 2, 2016

(54) PLATINUM COMPOUNDS, COMPOSITIONS, AND USES THEREOF

(71) Applicant: PLACON THERAPEUTICS, INC., Watertown, MA (US)

(72) Inventors: Mark T. Bilodeau, Concord, MA (US); Benoît Moreau, Newton, MA (US); Adam H. Brockman, Arlington, MA (US)

(73) Assignee: Placon Therapeutics, Inc., Watertown, MA (US)

( * ) Notice: Subject to any disclaimer, the term of this patent is extended or adjusted under 35 U.S.C. 154(b) by 0 days.

(21) Appl. No.: 14/944,610

(22) Filed: Nov. 18, 2015

(65) Prior Publication Data
US 2016/0068557 A1   Mar. 10, 2016

Related U.S. Application Data

(63) Continuation of application No. PCT/US2015/037071, filed on Jun. 23, 2015.

(60) Provisional application No. 62/015,714, filed on Jun. 23, 2014, provisional application No. 62/034,124, filed on Aug. 6, 2014, provisional application No. 62/035,126, filed on Aug. 8, 2014, provisional application No. 62/035,739, filed on Aug. 11, 2014, provisional application No. 62/150,045, filed on Apr. 20, 2015.

(51) Int. Cl.
| | |
|---|---|
| C07D 207/16 | (2006.01) |
| C07D 209/44 | (2006.01) |
| C07F 15/00 | (2006.01) |
| A61K 31/282 | (2006.01) |
| A61K 33/24 | (2006.01) |

(52) U.S. Cl.
CPC .............. *C07F 15/00* (2013.01); *A61K 31/282* (2013.01); *A61K 33/24* (2013.01)

(58) Field of Classification Search
CPC .......................... C07D 207/16; C07D 209/44
See application file for complete search history.

(56) References Cited

U.S. PATENT DOCUMENTS

2006/0205810 A1   9/2006 Zong et al.

OTHER PUBLICATIONS

Johnson et al., 2014, caplus an 2014:1753215.*
Liu et al., 2015, caplus an 2015:1726749.*
Bilodeau et al., 2015, caplus an 2015:1129122.*
International Search Report and Written Opinion from International Application No. PCT/US2015/037071 entitled "Platinum Compounds, Compositions, and Uses Thereof." Date of mailing: Sep. 21, 2015.
Pichler, V et al. "Maleimide-functionalised platinum(IV) complexes as a synthetic platform for targeted drug delivery." Chem. Commun. 2013. vol. 49, pp. 2249-2251.
Geng, X et al. Synthesis and characterization of cisplatin-loaded, EGFR-targeted biopolymer and in vitro evaluation for targeted delivery.. Journal of Biomedical Materials Research A. 2012. vol. 100 A(10), pp. 2839-2848.
Reithofer. MR et al. "Novel Di- and Tetracarboxylatoplatinum(IV) Complexes. Synthesis, Characterization, Cytotoxic Activity, and DNA Platination," J. Med. Chem. 2007. vol. 50, pp. 6692-6699.
Xiao, H et al. "A dual-targeting hybrid platinum(IV) prod rug for enhancing efficacy," Chern. Commun. 2012. vol. 48, pp. 10730-10732.
Galanski M, Jakupec MA, Keppler BK., Update of the Preclinical Situation of Anticancer Platinum Complexes: Novel Design Strategies and Innovative Analytical Approaches, Curr. Med. Chem. 2005; 12:2075-2094.
Wheate NJ, Walker S, Craig GE, Oun R., Dalton Trans., An International Journal of Inorganic Chemistry, The status of platinum anticancer drugs in the clinic and in clinical trials, 2010; 39:8113-8127.
Heffeter P, Jungwirth U, Jakupec M, Hartinger C, Galanski M, Elbling L, Micksche M, Keppler B, Berger W., Resistance against novel anticancer metal compounds: differences and similarities, Drug Resist. Updates. 2008; 11:1-16.
Choy H, Park C, Yao M., Current Status and Future Prospects for Satraplatin, an Oral Platinum Analogue, Clin. Cancer Res. 2008; 14:1633-1638.
Barnes KR, Kutikov A, Lippard S, Synthesis, Characterization, and Cytotoxicity of a Series of Estrogen-Tethered Platinum (IV) Complexes, J. Chem. Biol. 2004; 11:557-564.
Ang WH, Khalaila I, Allardyce CS, Juillerat-Jeanneret L, Dyson PJ., Rational Design of Platinum (IV) Compounds to Overcome Glutathione-S-Transferase Mediated Drug Resistance, J. Am. Chem. Soc. 2005; 127:1382-1383.
Dhar S, Liu Z, Thomale J, Dai H, Lippard SJ., Targeted Single Wall Carbon Nanotube Mediated Pt(IV) Prodrug Delivery Using Folate as a Homing Device, J. Am. Chem. Soc. 2008; 130:11467-11476.
Feazell RP, Nakayama-Ratchford N, Dai H, Lippard SJ., Soluble Single-Walled Carbon Nanotubes as Longboat Delivery Systems for Platinum (IV) Anticancer Drug Design, J. Am. Chem. Soc. 2007; 129:8438-8439.
Dhar S, Daniel WL, Giljohann DA, Mirkin CA, Lippard SJ., Polyvalent Oligonucleotide Gold Nanoparticles Conjugates as Delivery Vehicles for Platinum (IV) Warheads, J. Am. Chem. Soc. 2009; 131:14652-1465.
Grek CL, Tew KD., Redox Metabolism and Malignancy, Curr. Opin. Pharmacol. 2010; 10:362-368.
Wexselblatt E, Gibson D., What do we know about the reduction of Pt(IV) pro-drugs? J. Inorg. Biochem. 2012; 117:220-229.
Jungwirth U, Xanthos DN, Gojo J, Bytzek AK, Korner W, Heffeter P, Abramkin SA, Jakupec MA, Hartinger CG, Windberger U, Galanski M, Keppler BK, Berger W., Anticancer Activity of Methyl-Substituted Oxaliplatin Analogs, Mol. Pharmacol. 2012; 81:719-728.
Carr JL, Tingle MD, McKeage MJ., Rapid Biotransformation of Satraplatin by Human Red Blood Cells in Vitro, Cancer Chemother. Pharmacol. 2002; 50:9-15.

(Continued)

*Primary Examiner* — Sun Jae Yoo
(74) *Attorney, Agent, or Firm* — DT Ward, PC; Donna T. Ward; Heng Zhu

(57) ABSTRACT

The present teachings relate to compounds and compositions for treatment of cancers. In some embodiments, the composition comprises a platinum (IV) complex having at least one reacting group for reacting with a functional group on a protein, engineered protein, antibody, antibody fragment, peptide, agonist, antagonist, aptamer or ligand which may be capable of recognizing a selected target cell population, and/or derivatives/analogs/mimics thereof.

12 Claims, 31 Drawing Sheets

(56) References Cited

OTHER PUBLICATIONS

Carr JL, Tingle MD, McKeage MJ., Satraplatin Activation by Haemoglobin, Cytochrome C and Liver Microsomes in Vitro, Cancer Chemother. Pharmacol. 2006; 57:483-490.

Baban DF, Seymour LW., Control of Tumour Vascular Permeability, Adv. Drug Delivery Rev. 1998; 34:109-119.

Kratz F. J., Albumin as a drug carrier: Design of prodrugs, drug conjugates and nanoparticles, Controlled Release. 2008; 132:171-183.

Frei E., Albumin Binding Ligands and Albumin Conjugate Uptake by Cancer Cells, Diabetol. Metab. Syndr. 2011; 3:11.

Kratz F., Inno-206 (DOXO-EMCH), an Albumin-Binding Prodrug of Doxorubicin Under Development for Phase II Studies, Curr. Bioact. Compd. 2011; 7:33-38.

Miele E, Spinelli GP, Tomao F, Tomao S., Albumin-bound Formulation of Paclitaxel (Abraxane ABI-007) in the treatment of breast cancer), Int. J. Nanomed. 2009; 4:99.

Reithofer MR, Valiandi SM, Jakupec MA, Arion VB, Egger A, Galanski M, Keppler BK., Novel Di- and Tetracarboxylatoplatinum (IV) Complexes. Synthesis, Characterization, Cytotoxic Activity, and DNA Platination, J. Med. Chem. 2007; 50:6692-6699.

Pichler V, Valiandi SM, Jakupec MA, Arion VB, Galanski M, Keppler BK., Mono-carboxylated diaminedichloridoplatinum (iv) complexes- selective synthesis, characterization, and cytotoxicity, Dalton Trans. 2011;40:8187-8192.

R. M. De Figueiredo, P. Oczipka, R. Froehlich and M. Christmann, Synthesis of 4-Maleimidobutyric Acid and Related Maleimides, Synth., 2008, 1316-1318.

T. N. Bansode, J. V. Shelke and V. G. Dongre, Synthesis and antimicrobial activity of some new N-acyl substituted phenothiazines, Eur. J. Med. Chem., 2009, 44, 5094-5098.

J. J. Wilson and S. J. Lippard, Synthesis, Characterization, and Cytotoxicity of Platinum (IV) Carbamate Complexes, Inorg. Chem., 2011, 50, 3103-3115.

G. M. Sheldrick, Acta Crystallogr., A Short History of SHELX, Sect. A: Found. Crystallogr., 2007, 64, 112-122.

N. D. Chasteen, J. K. Grady and C. E. Holloway, Characterization of the Binding, Kinetics, and Redox Stability of Vanadium (IV) and Vanadium (V) Protein Complexes in Serum, Inorg. Chem., 1986, 25, 2754-2760.

K. Oettl and R. Stauber, Physiological and Pathological Changes in the Redox State of Human Serum Albumin Critically Influence its Binding Properties, Br J. Pharmacol., 2007, 151, 580-590.

C. K. Riener, G. Kada and H. J. Gruber, Quick Measurement of Protein Sulfhydryls with Ellman's Reagent and with 4,4'-dithiodipyridine, Anal. Bioanal. Chem., 2002, 373, 266-276.

D. R. Grassetti and J. F. Murray Jr, Determination of Sulfhydryl Groups with 2,2'- or 4,4'- Dithiodipyridine, Arch. Biochem. Biophys., 1967, 119, 41-49.

\* cited by examiner

KRAS
Mutant
MiaPaca-2

KRAS
WT
BxPC3

Representative images from day 10 of NCI-H520 study

Representative images from day 10 of NCI-H520 study (Apoptag)

PLATINUM COMPOUNDS, COMPOSITIONS, AND USES THEREOF

REFERENCED TO RELATED APPLICATIONS

The present application is a continuation of PCT Application No. PCT/US15/37071 filed Jun. 23, 2015, entitled Platinum Compounds, Compositions, and Uses Thereof, which claims priority to U.S. Provisional Patent Application No. 62/015,714, filed Jun. 23, 2014, entitled Monomaleimide Compounds, Compositions, and Uses Thereof, U.S. Provisional Patent Application No. 62/034,124, filed Aug. 6, 2014, entitled Monomaleimide Compounds, Compositions, and Uses Thereof, U.S. Provisional Patent Application No. 62/035,126, filed Aug. 8, 2014, entitled Novel Procedures of Synthesizing and Purifying Platinum Compounds, U.S. Provisional Patent Application No. 62/035,739, filed Aug. 11, 2014, entitled Novel Procedures of Synthesizing and Purifying Platinum Compounds, and U.S. Provisional Patent Application No. 62/150,045, filed Apr. 20, 2015, entitled Platinum Compounds, Compositions, and Uses Thereof, the contents of each of which are herein incorporated by reference in their entirety.

FIELD OF THE INVENTION

The invention relates to platinum based compounds.

BACKGROUND OF THE INVENTION

Platinum-based drugs are among the most active and widely used anticancer agents. Cisplatin is one of the few FDA-approved, platinum-based cancer chemotherapeutics. Although cisplatin is effective against a number of solid tumors, especially testicular and ovarian cancer, its clinical use has been limited because of its toxic effects as well as the intrinsic and acquired resistance of some tumors to this drug.

To overcome these limitations, platinum analogs with lower toxicity and greater activity in cisplatin-resistant tumors have been developed and tested, resulting in the approval of carboplatin and oxaliplatin in the United States. For example, carboplatin has the advantage of being less nephrotoxic, but its cross-resistance with cisplatin has limited its application in otherwise cisplatin-treatable diseases.

Oxaliplatin, however, exhibits a different anticancer spectrum from that of cisplatin. It has been approved as the first or second line therapy in combination with 5-fluorouracil/leucovorin for advanced colorectal cancer, for which cisplatin and carboplatin are essentially inactive. These platinum drugs have platinum in the 2+ oxidative state (Pt(II)) and are not orally active.

Platinum complexes in the 4+ oxidative state (Pt(IV) complexes) provide several advantages. Platinum(IV) complexes are substantially inactive in the 4+ oxidation state but become activated upon reduction to the platinum(II) state. As such Pt(IV) complexes constitute prodrugs of Pt(II) drugs that are activated in tumor cells. The two additional coordination sites (the axial sites) of Pt(IV) complexes can also be modified to change the pharmacokinetic properties of the complexes.

The two axial sites, as well as the four equatorial sites, can include a reacting group capable of reacting with amino groups, hydroxyl groups or thiol groups, forming a conjugate with a protein, antibody, antibody fragment, peptide, agonist, antagonist, aptamer or ligand which may be capable of recognizing a selected target cell population. The conjugation of the platinum(IV) complex can be performed prior to administration or can take place in vivo. The benefits of the conjugation for the platinum (IV) complex include increased circulation time, improved delivery to a target organ or to a targeted cell population.

The inclusion of a reacting group as disclosed in the present teachings may increase the Pt concentration in tumor cells and, in certain instances, may increase the efficacy in treating a disease or a condition discussed herein. In certain instances, Pt(IV) complexes of the present teachings can have a reduced long-term toxicity.

SUMMARY OF THE INVENTION

The present teachings relate to compositions, for example, for reducing, disrupting, or inhibiting the growth of a cancer cell or inducing the death of a cancer cell.

The composition can include a platinum (IV) compound. In various embodiments, the platinum (IV) compound includes a suitable reacting group for reacting with a functional group on a protein, engineered protein, antibody, antibody fragment, peptide, agonist, antagonist, aptamer or ligand which may be capable of recognizing a selected target cell population, and/or derivatives/analogs/mimics thereof. Such compounds are referred to herein as Pt(IV)M. The reacting group may be a Michael acceptor and/or alkylating functionality. For example, a Michael acceptor can be introduced by a linker between platinum and the Michael acceptor and/or alkylating functionality and/or alkylating functionality. In various embodiments, one of or both the axial positions of platinum each comprises one or more Michael acceptors and/or alkylating functionality.

In some embodiments, the present teachings provide a compound of Formula I:

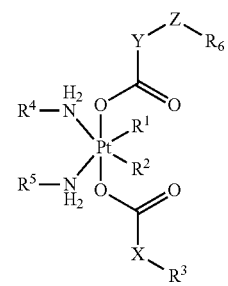

or a pharmaceutically acceptable salt thereof, wherein:
X and Y are independently selected from NH, alkyl and aryl;
$R^1$ and $R^2$ each is Cl, or $R^1$ and $R^2$ are joined to form an oxalate;
$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl;

$R^4$ and $R^5$ are each H or together constitute a cyclohexyl ring; and

Z is alternatively absent, alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

$R^6$ is a suitable reacting group for reacting a functional group of a protein, engineered protein, antibody, antibody fragment, peptide, agonist, antagonist, aptamer or ligand which may be capable of recognizing a selected target cell population, and/or derivatives/analogs/mimics thereof, and wherein $R^6$ is selected from any of the following groups:

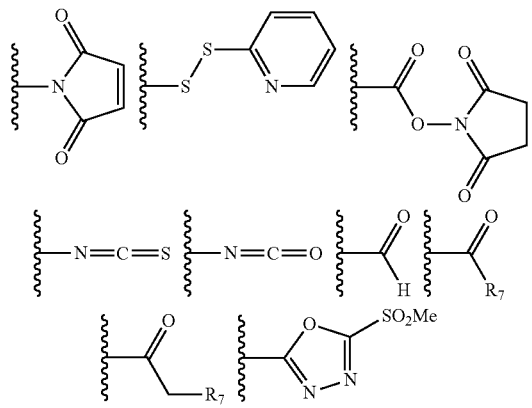

where $R^7$ is Cl, Br, F, mesylate, tosylate, O-(4-nitrophenyl), 0-pentafluorophenyl. The reacting group can also comprise an activated disulfide group, a vinylcarbonyl group, a vinyl acetylene group, an epoxide, an aziridine group or an acetylene group. The groups may be substituted, where appropriate.

The present teachings also provide compositions including a compound as described herein and methods of using a compound or a composition as described herein. In various embodiments, the methods of the present teachings are useful for the prevention or treatment of diseases that benefit from increased cell death or decreased cell proliferation. For example, the method of the present teachings can be used to increase cancer cell death or decrease cancer cell proliferation. The increased cancer cell death or decreased cancer proliferation can occur, for example, outside the body (in vitro) or inside the body (in vivo).

Certain embodiments of the present teachings also provide for use of a compound as described herein as a medicament for treating or preventing a disease and/or in the manufacture of such a medicament, e.g., for use in the treatment of a disease. Some embodiments provide the use of a compound as described herein for use as a medicament. In certain embodiments, the teachings provide a compound or composition as described herein for the treatment of disease, e.g. for the treatment of a cancer. In certain embodiments, the teachings provide a compound or composition as described herein for the treatment of a tumor, wherein the tumor cells express one or more KRAS mutations.

The present teachings also provide a novel method of synthesizing and purifying compounds as described herein.

DETAILED DESCRIPTION

Figure 1:
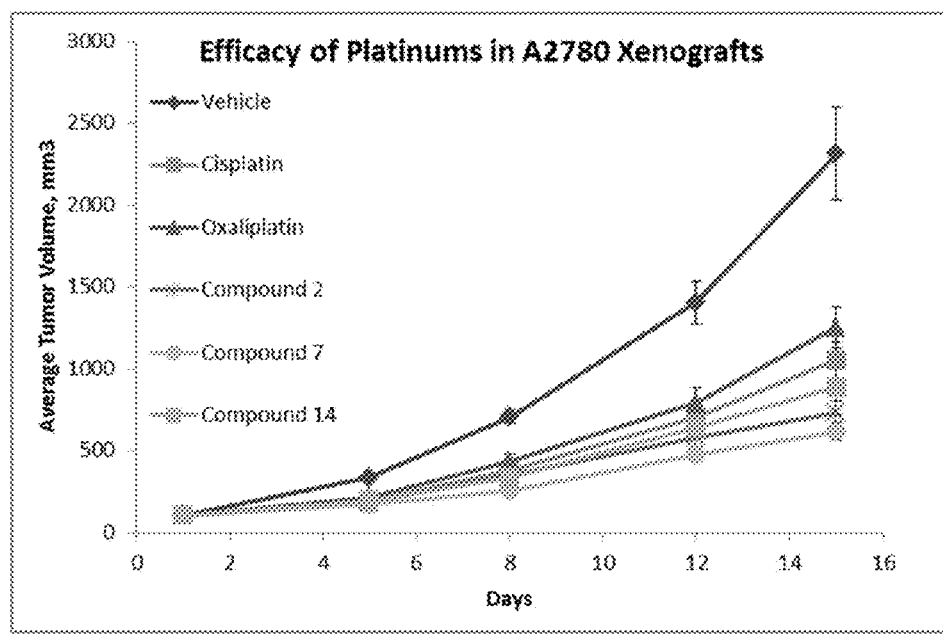
FIG. 1 is a graph illustrating growth curves of A2780 tumors in nude mouse xenografts when mice were dosed with two control drugs, vehicle or three Pt(IV)M of the present teachings.

Applicants have discovered that Pt(IV) compounds having a suitable reacting group for reacting with a functional group on a protein, engineered protein, antibody, antibody fragment, peptide, agonist, antagonist, aptamer or ligand which may be capable of recognizing a selected target cell population, and/or derivatives/analogs/mimics thereof, are effective inhibitors of cellular proliferation and tumor growth. Such compounds are referred to herein as Pt(IV)M compounds. The product resulting from the reaction of Pt(IV)M with a functional group present on either a protein, engineered protein, antibody, antibody fragment, peptide, agonist, antagonist, aptamer or ligand are referred to herein as Pt(IV)M conjugates.

The term "ligand" as used herein includes any molecule that specifically binds or reactively associated or complexes with a receptor or other receptive moiety associated with a given target cell population.

The term "reacting group" as used herein refers to a functional group of the Pt(IV) compounds that may react with a functional group on a protein, engineered protein, antibody, antibody fragment, peptide, agonist, antagonist, aptamer or ligand which may be capable of recognizing a selected target cell population, and/or derivatives/analogs/mimics thereof. The functional group on a protein, engineered protein, antibody, antibody fragment, peptide, agonist, antagonist, aptamer or ligand which may be capable of recognizing a selected target cell population, and/or derivatives/analogs/mimics thereof, may be amino groups, hydroxyl groups or thiol groups.

Non-limiting examples of a reacting group include an activated disulfide group, a vinylcarbonyl group, a vinyl acetylene group, an epoxide, an aziridine group or an acetylene group. The groups may be substituted, where appropriate. The reacting group may also be any of:

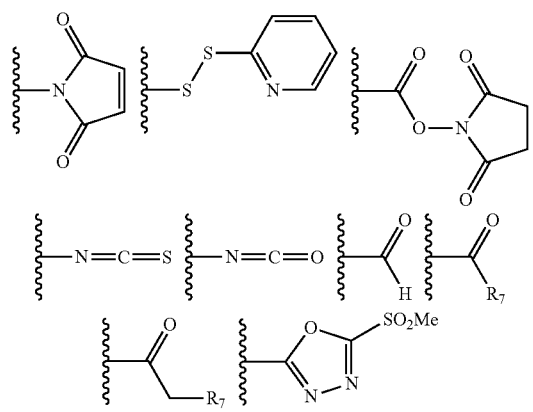

where $R^7$ is Cl, Br, F, mesylate, tosylate, O-(4-nitrophenyl), 0-pentafluorophenyl.

In some embodiments, the Pt(IV)M conjugate results from the reaction of the Pt(IV)M compound with the protein, engineered protein, antibody, antibody fragment, peptide, agonist, antagonist, aptamer or ligand which may be capable of recognizing a selected target cell population, and/or derivatives/analogs/mimics thereof, in vivo, i.e., the conjugation between the reacting group and the functional group takes place in vivo.

In some embodiments, Pt(IV)M conjugate results from the reaction of the Pt(IV)M compound with the protein, engineered protein, antibody, antibody fragment, peptide, agonist, antagonist, aptamer or ligand which may be capable of recognizing a selected target cell population, and/or derivatives/analogs/mimics thereof, prior to administration outside of the body, i.e., the conjugation between the reacting group and the functional group is performed prior to administration in vivo.

The protein, engineered protein, antibody, antibody fragment, peptide, agonist, antagonist, aptamer or ligand which may be capable of recognizing a selected target cell population, and/or derivatives/analogs/mimics thereof may be any ligand disclosed in EP 0554708 to Willner et al. (BMS), the contents of which are incorporated herein by reference in their entirety. For example, the protein, engineered protein, antibody, antibody fragment, peptide, agonist, antagonist, aptamer or ligand which may be capable of recognizing a selected target cell population, and/or derivatives/analogs/mimics thereof may be non-immunoreactive, such as but not limited to transferrin, epidermal growth factors ("EGF"), bombesin, gastrin, gastrin-releasing peptide, platelet-derived growth factor, IL-2, IL-6, tumor growth factors ("TGF"), such as TGF-α and TGF-β, vaccinia growth factor ("VGF"), insulin and insulin-like growth factors I and II. Non-peptidyl ligands may include, for example, steroids, carbohydrates and lectins. The protein, engineered protein, antibody, antibody fragment, peptide, agonist, antagonist, aptamer or ligand which may be capable of recognizing a selected target cell population, and/or derivatives/analogs/mimics thereof may also be non-immunoreactive such as but not limited to an antigen-recognizing immunoglobulin (also referred to as "antibody"), or antigen-recognizing fragment thereof. The immunoglobulins may be immunoglobulins which can recognize a tumor-associated antigen. As used, "immunoglobulin" may refer to any recognized class or subclass of immunoglobulins such as IgG, IgA, IgM, IgD, or IgE. The immunoglobulin can be derived from any species such as human, murine, or rabbit origin. Further, the immunoglobulin may be polyclonal, monoclonal, chimeric, bifunctional or hybrid.

In some embodiments, the protein is albumin or derivatives/analogs/mimics thereof. In some embodiments, the engineered protein may be a recombinant albumin (rAlbumin) such as the recombinant albumin disclosed in US 20090280534 to Christensen et al. (Novozymes), the contents of which are incorporated herein by reference in their entirety.

The reacting group may be a Michael acceptor and/or alkylating functionality. In some embodiments, the Pt(IV)M compounds comprise a maleimide group and/or derivatives thereof.

"Michael acceptor", as used herein, refers to an α,β-unsaturated electrophile, such as, but not limited to, an α,β-unsaturated carbonyl derivative or an α,β-unsaturated nitrite: "Electrophile" means able to accept an electron pair; "α,β-unsaturated electrophile" means the compound class that includes, but is not limited to, α,β-unsaturated carbonyl derivative, α,β-unsaturated nitrite, α,β-unsaturated sulfone, or other vinyl derivative substituted with a strong electron withdrawing group, such as, but not limited to, a nitro group; "α,β-unsaturated carbonyl derivative" means the compound class that includes, but is not limited to, α,β-unsaturated ketone, quinone or derivative thereof, α,β-unsaturated aldehyde, α,β-unsaturated carboxylic acid derivative, such as, but not limited to, an ester, an amide, a substituted amide, or a maleimide or a derivative thereof.

A feature of the Pt(IV)M compounds and/or Pt(IV)M conjugates is their relatively low toxicity to an organism while maintaining efficacy at inhibiting, e.g. slowing or stopping tumor growth. As used herein, "toxicity" refers to the capacity of a substance or composition to be harmful or poisonous to a cell, tissue organism or cellular environment. Low toxicity refers to a reduced capacity of a substance or composition to be harmful or poisonous to a cell, tissue organism or cellular environment. Such reduced or low toxicity may be relative to a standard measure, relative to a treatment or relative to the absence of a treatment.

Toxicity may further be measured relative to a subject's weight loss where weight loss over 15%, over 20% or over 30% of the body weight is indicative of toxicity. Other metrics of toxicity may also be measured such as patient presentation metrics including lethargy and general malaiase. Neutropenia or thrombopenia may also be metrics of toxicity.

Pharmacologic indicators of toxicity include elevated AST/ALT levels, neurotoxicity, kidney damage, GI damage and the like.

Furthermore, in some embodiments, such Pt(IV)M compounds and/or Pt(IV)M conjugates are effective for inhibiting tumor growth, whether measured as a net value of size (weight, surface area or volume) or as a rate over time, in multiple types of tumors.

In some embodiments the size of a tumor is reduced by 60% or more. In some embodiments, the size of a tumor is reduced by at least 20%, at least 30%, at least 40%, at least 50%, at least 60%, at least 70%, at least 80%, at least 90%, at least 95%, at least 96%, at least 97%, at least 98%, at least 99%, at least 100%, by a measure of weigth, and/or area and/or volume.

In some embodiments, the RECIST (Response Evaluation Criteria In Solid Tumors) criteria are used to characterize the effects of the compounds of the invention on solid tumors. The guidelines for gauging tumors were updated and published in the European Journal of Cancer (EJC) in January 2009 (Eisenhauer, et al., European Journal of Cancer: 45 (2009) 228-247), the contents of which are incorporated herein by reference in their entirety. Any of the RECIST metrics may be used to characterize the effects of the compounds of the invention on tumors including but not limited to response, assessment and measurement criteria.

In some embodiments Progression Free Survival and Overall Survival are used to characterize the effects of the compounds of the invention on solid tumors.

It has been surprisingly found that the relative ability of Pt(IV)M compounds and/or Pt(IV)M conjugates of the invention to inhibit in vitro cell proliferation is not predictive of their relative ability to inhibit tumor growth, i.e., their relative ability to inhibit tumor growth is greater than their relative ability to inhibit cell proliferation in vitro.

Without wishing to be bound to any theory, the effective delivery of a Pt(IV)M compound may be related to the covalent attachment of the compound to a protein such as albumin. Conjugation to albumin prevents rapid clearance and delivers stable and inactive form of platinum to tumor sites. The compound-albumin bond may be cleaved at a tumor site, creating an active platinum compound, e.g., a Pt(II) compound. Trafficking of a Pt(IV)M compound by albumin is being studied with MIA PaCa-2 and BxPC-3 cell lines (Commisso et al., Nature, vol. 497:633-637 (2013), the contents of which are incorporated herein by reference in their entirety).

In some embodiments, a Pt(IV)M compound and/or Pt(IV)M conjugates as described herein is administered to a subject who has a tumor comprising cells that express one or more KRAS mutations. A subject's tumor may be assayed for KRAS mutations using methods known in the art, for example, see Anderson, 2011, Expert Rev Mol Diagn. 11:635-642 and Thierry et al., 2014, Nature Medicine 20:430-435, the contents of each of which are incorporated herein by reference in their entirety. If the tumor has a KRAS mutation, the tumor is likely to be responsive to treatment by the Pt(IV)M compounds and/or Pt(IV)M conjugates disclosed herein. In some embodiments, the tumor is directly assayed for the presence of a KRAS mutation. In some embodiments, a non-tumor tissue, e.g., tumor DNA that is circulating in the plasma is assayed for the presence of a KRAS mutation.

This finding is also important because some tumors containing cells that express one or more KRAS mutants are not sensitive to certain treatments. For example, colorectal cancer patients are tested for the presence of KRAS mutations because the presence of certain of these mutations predicts resistance to therapies directed against EGFR (Siena et al., 2009, J Natl Cancer Inst 101:1308-24, the contents of which are incorporated herein by reference in their entirety). Such patients are candidates for treatments with a Pt(IV)M compound and/or Pt(IV)M conjugates described herein.

For convenience, before further description of the present teachings, certain definitions of terms employed in the specification and claims are collected here. These definitions should be read in light of the remainder of the disclosure and as understood by a person of ordinary skill in the art. Unless defined otherwise, all technical and scientific terms used herein have the same meaning as commonly understood by a person of ordinary skill in the art.

The articles "a" and "an," as used herein, should be understood to mean "at least one," unless clearly indicated to the contrary.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements.

In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to.

Only the transitional phrases "consisting of" and "consisting essentially of" shall be closed or semi-closed transitional phrases, respectively, as set forth in the United States Patent Office Manual of Patent Examining Procedures.

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with cancer or otherwise known to have cancer or one selected for treatment, observation, or experiment on the basis of a known cancer in the subject.

As used herein, "treatment" or "treating" refers to amelioration of a disease or disorder, or at least one sign or symptom thereof "Treatment" or "treating" can refer to reducing the progression of a disease or disorder, as determined by, e.g., stabilization of at least one sign or symptom or a reduction in the rate of progression as determined by a reduction in the rate of progression of at least one sign or symptom. In another embodiment, "treatment" or "treating" refers to delaying the onset of a disease or disorder.

As used herein, "prevention" or "preventing" refers to a reduction of the risk of acquiring or having a sign or symptom a given disease or disorder, i.e., prophylactic treatment.

The phrase "therapeutically effective amount" as used herein means that amount of a compound, material, or composition comprising a compound of the present teachings that is effective for producing a desired therapeutic effect. Accordingly, a therapeutically effective amount treats or prevents a disease or a disorder, e.g., ameliorates at least one sign or symptom of the disorder. In various embodiments, the disease or disorder is a cancer.

A dash ("-") that is not between two letters or symbols is used to indicate a point of attachment for a substituent. For example, —$CONH_2$ is attached through the carbon atom (C).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "alkyl" as used herein refers to a saturated straight or branched hydrocarbon, such as a straight or branched group of 1-22, 1-8, 1-6, or 1-4 carbon atoms, referred to herein as ($C_1$-$C_{22}$)alkyl, ($C_1$-$C_8$)alkyl, ($C_1$-$C_6$) alkyl, and ($C_1$-$C_4$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkenyl" as used herein refers to an unsaturated straight or branched hydrocarbon having at least one carbon-carbon double bond (shown, for example, as "="), such as a straight or branched group of 2-22, 2-8, 2-6, or 2-4 carbon atoms, referred to herein as $(C_2-C_{22})$alkenyl, $(C_2-C_8)$alkenyl, $(C_2-C_6)$alkenyl, and $(C_2-C_4)$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkynyl" as used herein refers to an unsaturated straight or branched hydrocarbon having at least one carbon-carbon triple bond (shown, for example, as "≡"), such as a straight or branched group of 2-22, 2-8, 2-6, 2-4 carbon atoms, referred to herein as $(C_2-C_{22})$alkynyl, $(C_2-C_8)$alkynyl, $(C_2-C_6)$alkynyl, and $(C_2-C_4)$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "cycloalkyl" as used herein refers to a saturated or unsaturated monocyclic, bicyclic, other multicyclic, or bridged cyclic hydrocarbon group. A cyclocalkyl group can have 3-22, 3-12, or 3-8 ring carbons, referred to herein as $(C_3-C_{22})$cycloalkyl, $(C_3-C_{12})$cycloalkyl, or $(C_3-C_8)$cycloalkyl, respectively. A cycloalkyl group can also have one or more carbon-carbon double bond or carbon-carbon triple bond.

Exemplary monocyclic cycloalkyl groups include, but are not limited to, cyclopentanes (cyclopentyls), cyclopentenes (cyclopentenyls), cyclohexanes (cyclohexyls), cyclohexenes (cyclopexenyls), cycloheptanes (cycloheptyls), cycloheptenes (cycloheptenyls), cyclooctanes (cyclooctyls), cyclooctenes (cyclooctenyls), cyclononanes (cyclononyls), cyclononenes (cyclononenyls), cyclodecanes (cyclodecyls), cyclodecenes (cyclodecenyls), cycloundecanes (cycloundecyls), cycloundecenes (cycloundecenyls), cyclododecanes (cyclododecyls), and cyclododecenes (cyclododecenyls). Other exemplary cycloalkyl groups, including bicyclic, multicyclic, and bridged cyclic groups, include, but are not limited to, bicyclobutanes (bicyclobutyls), bicyclopentanes (bicyclopentyls), bicyclohexanes (bicyclohexyls), bicycleheptanes (bicycloheptyls, including bicyclo[2,2,1]heptanes (bicycle[2,2,1]heptyls) and bicycle[3,2,0]heptanes (bicycle[3,2,0]heptyls)), bicyclooctanes (bicyclooctyls, including octahydropentalene (octahydropentalenyl), bicycle [3,2,1]octane (bicycle[3,2,1]octyl), and bicylo[2,2,2]octane (bicycle[2,2,2]octyl)), and adamantanes (adamantyls). Cycloalkyl groups can be fused to other cycloalkyl saturated or unsaturated, aryl, or heterocyclyl groups.

The term "aryl" as used herein refers to a mono-, bi-, or other multi-carbocyclic aromatic ring system. The aryl can have 6-22, 6-18, 6-14, or 6-10 carbons, referred to herein as $(C_6-C_{22})$aryl, $(C_6-C_{18})$aryl, $(C_6-C_{14})$aryl, or $(C_6-C_{10})$aryl, respectively. The aryl group can optionally be fused to one or more rings selected from aryls, cycloalkyls, and heterocyclyls. The term "bicyclic aryl" as used herein refers to an aryl group fused to another aromatic or non-aromatic carbocyclic or heterocyclic ring. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl" or phenyl. The phenyl group can also be fused to a cyclohexane or cyclopentane ring to form another aryl.

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$ arylalkyl." The term "benzyl" as used herein refers to the group —$CH_2$-phenyl.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "heteroalkenyl" and "heteroalkynyl" refer to unsaturated aliphatic groups analogous in length and possible substitution to the heteroalkyls described above, but that contain at least one double or triple bond, respectively.

The term "heterocycle" refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. Thus, heterocycles also include bicyclic, tricyclic, and tetracyclic groups in which any of the above heterocyclic rings is fused to one or two rings independently selected from aryls, cycloalkyls, and heterocycles. The heterocycle may also be fused to a spirocyclic group.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like.

In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, isoquinoline, benzoquinoline, benzoisoquinoline, phenanthridine-1, 9-diamine, or the like.

The term "heteroaromatic" or "heteroaryl" as used herein refers to a mono-, bi-, or multi-cyclic aromatic ring system containing one or more heteroatoms, for example 1-3 heteroatoms, such as nitrogen, oxygen, and sulfur. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or stable 12- to 14-membered fused tricyclic heterocyclic ring system which contains an aromatic ring that contains at least one heteroatom selected from the group consisting of N, O, and S. In some embodiments, at least one nitrogen is in the aromatic ring.

Heteroaromatics or heteroaryls can include, but are not limited to, a monocyclic aromatic ring, wherein the ring comprises 2-5 carbon atoms and 1-3 heteroatoms, referred to herein as "($C_2$-$C_5$)heteroaryl." Illustrative examples of monocyclic heteroaromatic (or heteroaryl) include, but are not limited to, pyridine (pyridinyl), pyridazine (pyridazinyl), pyrimidine (pyrimidyl), pyrazine (pyrazyl), triazine (triazinyl), pyrrole (pyrrolyl), pyrazole (pyrazolyl), imidazole (imidazolyl), (1,2,3)- and (1,2,4)-triazole ((1,2,3)- and (1,2,4)-triazolyl), pyrazine (pyrazinyl), pyrimidine (pyrimidinyl), tetrazole (tetrazolyl), furan (furyl), thiophene (thienyl), isoxazole (isoxazolyl), thiazole (thiazolyl), isoxazole (isoxazolyl), and oxazole (oxazolyl).

The term "bicyclic heteroaromatic" or "bicyclic heteroaryl" as used herein refers to a heteroaryl group fused to another aromatic or non-aromatic carbocyclic or heterocyclic ring. Exemplary bicyclic heteroaromatics or heteroaryls include, but are not limited to 5,6- or 6,6-fused systems, wherein one or both rings contain heteroatoms. The term "bicyclic heteroaromatic" or "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur.

Exemplary bicyclic heteroaromatics (or heteroaryls) include, but are not limited to, quinazoline (quinazolinyl), benzoxazole (benzoxazolyl), benzothiophene (benzothiophenyl), benzoxazole (benzoxazolyl), benzisoxazole (benzisoxazolyl), benzimidazole (benzimidazolyl), benzothiazole (benzothiazolyl), benzofurane (benzofuranyl), benzisothiazole (benzisothiazolyl), indole (indolyl), indazole (indazolyl), indolizine (indolizinyl), quinoline (quinolinyl), isoquinoline (isoquinolinyl), naphthyridine (naphthyridyl), phthalazine (phthalazinyl), phthalazine (phthalazinyl), pteridine (pteridinyl), purine (purinyl), benzotriazole (benzotriazolyl), and benzofurane (benzofuranyl). In some embodiments, the bicyclic heteroaromatic (or bicyclic heteroaryl) is selected from quinazoline (quinazolinyl), benzimidazole (benzimidazolyl), benzothiazole (benzothiazolyl), indole (indolyl), quinoline (quinolinyl), isoquinoline (isoquinolinyl), and phthalazine (phthalazinyl). In certain embodiments, the bicyclic heteroaromatic (or bicyclic heteroaryl) is quinoline (quinolinyl) or isoquinoline (isoquinolinyl).

The term "tricyclic heteroaromatic" or "tricyclic heteroaryl" as used herein refers to a bicyclic heteroaryl group fused to another aromatic or non-aromatic carbocyclic or heterocyclic ring. The term "tricyclic heteroaromatic" or "tricyclic heteroaryl" also encompasses reduced or partly reduced forms of fused aromatic system wherein one or both rings contain ring heteroatoms. Each of the ring in the tricyclic heteroaromatic (tricyclic heteroaryl) may contain up to three heteroatoms, independently selected from oxygen, nitrogen, and sulfur.

Exemplary tricyclic heteroaromatics (or heteroaryls) include, but are not limited to, acridine (acridinyl), 9H-pyrido[3,4-b]indole (9H-pyrido[3,4-b]indolyl), phenanthridine (phenanthridinyl), pyrido[1,2-a]benzimidazole (pyrido[1,2-a]benzimidazolyl), and pyrido[1,2-b]indazole (pyrido[1,2-b]indazolyl).

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$)alkoxy, ($C_1$-$C_8$)alkoxy, or ($C_1$-$C_6$)alkoxy, respectively. Exemplary alkoxy groups include, but are not limited to methoxy and ethoxy.

The term "cycloalkoxy" as used herein refers to a cycloalkyl group attached to an oxygen.

The term "aryloxy" or "aroxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy." The term "arylalkoxy" as used herein refers to an arylalkyl group attached to an oxygen atom. An exemplary aryalkyl group is benzyloxy group.

The term "amine" or "amino" as used herein refers to both unsubstituted and substituted amines, e.g., $NR_aR_bR_{b'}$, where $R_a$, $R_b$, and $R_{b'}$ are independently selected from alkyl, alkenyl, alkynyl, aryl, arylalkyl, carbamate, cycloalkyl, haloalkyl, heteroaryl, heterocyclyl, and hydrogen, and at least one of the $R_a$, $R_b$, and $R^{b'}$ is not hydrogen. The amine or amino can be attached to the parent molecular group through the nitrogen. The amine or amino also may be cyclic, for example any two of $R_a$, $R_b$, and $R^{b'}$ may be joined together and/or with the N to form a 3- to 12-membered ring (e.g., morpholino or piperidinyl). The term amino also includes the corresponding quaternary ammonium salt of any amino group.

Exemplary amines include alkylamine, wherein at least one of $R_a$, $R_b$, or $R^{b'}$ is an alkyl group, or cycloalkylamine, wherein at least one of $R_a$, $R_b$, or $R^{b'}$ is a cycloalkyl group.

The term "ammonia" as used herein refers to $NH_3$.

The term "aldehyde" or "formyl" as used herein refers to —CHO.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "amide" as used herein refers to the form —$NR_cC(O)(R_d)$— or —$C(O)NR_cR_e$, wherein $R_c$, $R_d$, and $R_e$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_c$, $R_d$, or $R_e$. The amide also may be cyclic, for example $R_c$ and $R_e$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa.

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —$S(O)_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "carbamate" as used herein refers to the form —$R_fOC(O)N(R_g)$—, —$R_fOC(O)N(R_g)R_h$—, or —$OC(O)NR_gR_h$, wherein $R_f$, $R_g$, and $R_h$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_f$, $R_g$ and $R_h$ are independently selected from aryl or heteroaryl, such as pyridinyl, pyridazinyl, pyrimidinyl, and pyrazinyl).

The term "carbonyl" as used herein refers to —C(O)—.

The term "carboxy" or "carboxylate" as used herein refers to $R_j$—COOH or its corresponding carboxylate salts (e.g., $R_j$—COONa), where $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. Exemplary carboxys include, but are not limited to, alkyl carboxy wherein R, is alkyl, such as —O—C(O)-alkyl. Exemplary carboxy also include aryl or heteroaryl carboxy, e.g. wherein R, is an aryl, such as phenyl and tolyl, or heteroaryl group such as pyridine, pyridazine, pyrmidine and pyrazine. The term carboxy also includes "carboxycarbonyl," e.g. a carboxy group attached to a carbonyl group, e.g., —C(O)—COOH or salts, such as —C(O)—COONa.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "cyano" as used herein refers to —CN.

The term "ester" refers to the structure —C(O)O—, —C(O)O—$R_i$—, —$R_j$C(O)O—$R_i$—, or —$R_j$C(O)O—, where O is not bound to hydrogen, and $R_i$ and $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_1$ can be a hydrogen, but $R_j$ cannot be hydrogen. The ester may be cyclic, for example the carbon atom and $R_j$, the oxygen atom and $R_i$, or $R_i$ and $R_j$ may be joined to form a 3- to 12-membered ring. Exemplary esters include, but are not limited to, alkyl esters wherein at least one of $R_i$ or $R_j$ is alkyl, such as —O—C(O)-alkyl, —C(O)—O-alkyl-, and -alkyl-C(O)—O-alkyl-. Exemplary esters also include aryl or heteroaryl esters, e.g. wherein at least one of $R_i$ or $R_j$ is an aryl group, such as phenyl or tolyl, or a heteroaryl group, such as pyridine, pyridazine, pyrimidine or pyrazine, such as a nicotinate ester. Exemplary esters also include reverse esters having the structure —$R_j$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —$R_k$O—$R_l$—, where $R_k$ and $R_l$ can independently be alkyl, alkenyl, alkynyl, aryl, cycloalkyl, heterocyclyl, and ether. The ether can be attached to the parent molecular group through $R_k$ or $R_1$. Exemplary ethers include, but are not limited to, alkoxyalkyl and alkoxyaryl groups. Ethers also includes polyethers, e.g., where one or both of $R_k$ and $R_l$ are ethers.

The terms "halo" or "halogen" or "hal" or "halide" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_m$ (such as acetyl, —C(O)CH$_3$) or —$R_m$—C(O)—$R_n$—. The ketone can be attached to another group through $R_m$ or R. $R_m$ or $R_n$ can be alkyl, alkenyl, alkynyl, cycloalkyl, heterocyclyl or aryl, or $R_m$ or $R_n$ can be joined to form, for example, a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —NO$_2$.

The term "nitrate" as used herein refers to NO$_3^-$.

The term "perfluoroalkyl" as used herein refers to an alkyl group in which all of the hydrogen atoms have been replaced by fluorine atoms. Exemplary perfluoroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "perfluoroalkoxy" as used herein refers to an alkoxy group in which all of the hydrogen atoms have been replaced by fluorine atoms.

The term "phosphate" as used herein refers to the structure —OP(O)O$_2^{2-}$, —R$_o$OP(O)O$_2^{2-}$, —OP(O)(OR$_q$)O$^-$, or —R$_o$OP(O)(OR$_p$)O$^-$, wherein R$_o$, R$_p$ and R$_q$ each independently can be alkyl, alkenyl, alkynyl, aryl, cycloalkyl, heterocyclyl, or hydrogen.

The term "sulfide" as used herein refers to the structure —R$_q$S—, where R$_q$ can be alkyl, alkenyl, alkynyl, aryl, arylalkyl, cycloalkyl, haloalkyl, heteroaryl, heterocyclyl. The sulfide may be cyclic, for example, forming a 3 to 12-membered ring. The term "alkylsulfide" as used herein refers to an alkyl group attached to a sulfur atom.

The term "sulfinyl" as used herein refers to the structure —S(O)O—, —R$_r$S(O)O—, —R$_r$S(O)OR$_s$—, or —S(O)OR$_s$—, wherein R$_r$ and R$_s$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of R$_r$ or R$_s$ is alkyl, alkenyl, or alkynyl.

The term "sulfonamide" as used herein refers to the structure —(R$_t$)—N—S(O)$_2$—R$_v$— or —R$_t$(R$_u$)N—S(O)$_2$—R$_v$, where R$_t$, R$_u$, and R$_v$ can be, for example, hydrogen, alkyl, alkenyl, alkynyl, aryl, cycloalkyl, and heterocyclyl. Exemplary sulfonamides include alkylsulfonamides (e.g., where R$_v$ is alkyl), arylsulfonamides (e.g., where R$_v$ is aryl), cycloalkyl sulfonamides (e.g., where R$_v$ is cycloalkyl), and heterocyclyl sulfonamides (e.g., where R$_v$ is heterocyclyl).

The term "sulfonate" as used herein refers to a salt or ester of a sulfonic acid. The term "sulfonic acid" refers to R$_w$SO$_3$H, where R$_w$ is alkyl, alkenyl, alkynyl, aryl, cycloalkyl, or heterocyclyl (e.g., alkylsulfonyl). The term "sulfonyl" as used herein refers to the structure R$_x$SO$_2$—, where R$_x$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "sulfonate" as used herein refers $R_w SO_3^-$, where $R_w$ is alkyl, alkenyl, alkynyl, cycloalkyl, aryl, heterocyclyl, hydroxyl, alkoxy, aroxy, or aralkoxy, where each of the alkyl, alkenyl, alkynyl, cycloalkyl, aryl, heteroaryl, alkoxy, aroxy, or aralkoxy optionally is substituted. Non-limiting examples include triflate (also known as trifluoromethanesulfonate, $CF_3SO_3$), benzenesulfonate, tosylate (also known as toluenesulfonate), and the like.

The term "thioketone" refers to the structure —$R_y$—C(S)—$R_z$—. The ketone can be attached to another group through $R_y$ or $R_z$. $R_y$ or $R_z$ can be alkyl, alkenyl, alkynyl, cycloalkyl, heterocyclyl or aryl, or $R_y$ or $R_z$ can be joined to form a ring, for example, a 3- to 12-membered ring.

Each of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of the present teachings, the heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

As a non-limiting example, in various embodiments when one of the $R_a$, $R_b$, and $R_{b'}$ in $NR_a R_b R_{b'}$, referred to herein as an amine or amino, is selected from alkyl, alkenyl, alkynyl, cycloalkyl, and heterocyclyl, each of the alkyl, alkenyl, alkynyl, cycloalkyl, and heterocyclyl independently can be optionally substituted with one or more substituents each independently selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents. In some embodiments when the amine is an alkyl amine or a cycloalkylamine, the alkyl or the cycloalkyl can be substituted with one or more substituents each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. In certain embodiments when the amine is an alkyl amine or a cycloalkylamine, the alkyl or the cycloalkyl can be substituted with one or more substituents each independently selected from amino, carboxy, cyano, and hydroxyl. For example, the alkyl or the cycloalkyl in the alkyl amine or the cycloalkylamine is substituted with an amino group, forming a diamine.

As used herein, a "suitable substituent" refers to a group that does not nullify the synthetic or pharmaceutical utility of the compounds of the invention or the intermediates useful for preparing them. Examples of suitable substituents include, but are not limited to: ($C_1$-$C_{22}$), ($C_1$-$C_8$), ($C_1$-$C_6$), or ($C_1$-$C_4$) alkyl, alkenyl or alkynyl; ($C_6$-$C_{22}$), ($C_6$-$C_{18}$), ($C_6$-$C_{14}$), or ($C_6$-$C_{10}$) aryl; ($C_2$-$C_{21}$), ($C_2$-$C_{17}$), ($C_2$-$C_{13}$), or ($C_2$-$C_9$) heteroaryl; ($C_3$-$C_{22}$), ($C_3$-$C_{12}$), or ($C_3$-$C_8$) cycloalkyl; ($C_1$-$C_{22}$), ($C_1$-$C_8$), ($C_1$-$C_6$), or ($C_1$-$C_4$) alkoxy; ($C_6$-$C_{22}$), ($C_6$-$C_{18}$), ($C_6$-$C_{14}$), or ($C_6$-$C_{10}$) aryloxy; —CN; —OH; oxo; halo; carboxy; amino, such as —NH(($C_1$-$C_{22}$), ($C_1$-$C_8$), ($C_1$-$C_6$), or ($C_1$-$C_4$) alkyl), —N(($C_1$-$C_{22}$), ($C_1$-$C_8$), ($C_1$-$C_6$), or ($C_1$-$C_4$) alkyl)$_2$, —NH(($C_6$)aryl), or —N(($C_6$-$C_{10}$) aryl)$_2$; formyl; ketones, such as —CO(($C_1$-$C_{22}$), ($C_1$-$C_8$), ($C_1$-$C_6$), or ($C_1$-$C_4$) alkyl), —CO((($C_6$-$C_{10}$) aryl) esters, such as —$CO_2$(($C_1$-$C_{22}$), ($C_1$-$C_8$), ($C_1$-$C_6$), or ($C_1$-$C_4$) alkyl) and —$CO_2$(($C_6$-$C_{10}$) aryl). One of skill in art can readily choose a suitable substituent based on the stability and pharmacological and synthetic activity of the compound of the invention.

The term "pharmaceutically acceptable counter ion" refers to a pharmaceutically acceptable anion or cation. In various embodiments, the pharmaceutically acceptable counter ion is a pharmaceutically acceptable ion. For example, the pharmaceutically acceptable counter ion is selected from citrate, malate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). In some embodiments, the pharmaceutically acceptable counter ion is selected from chloride, bromide, iodide, nitrate, sulfate, bisulfate, phosphate, acid phosphate, citrate, malate, acetate, oxalate, acetate, and lactate. In particular embodiments, the pharmaceutically acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present teachings. Compounds included in the present teachings that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, malate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present teachings that include an amino moiety may form pharmaceutically acceptable salts with various amino acids, in addition to the acids mentioned above. Compounds included in the present teachings, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

Unless otherwise specified, the chemical groups include their corresponding monovalent, divalent, trivalent, and tetravalent groups. For example, methyl includes monovalent methyl ($-CH_3$), divalent methyl ($-CH_2-$, methylyl), trivalent methyl

and tetravalent methyl

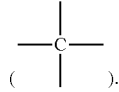

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques. For example, the term "about" can encompass variations of ±10%, ±5%, ±2%, ±1%, ±0.5%, or ±0.1% of the numerical value of the number which the term "about" modifies. In various embodiments, the term "about" encompasses variations of ±5%, ±2%, ±1%, or ±0.5% of the numerical value of the number. In some embodiments, the term "about" encompasses variations of ±5%, ±2%, or ±1% of the numerical value of the number. In certain embodiments, the term "about" encompasses variations of ±5% of the numerical value of the number. In certain embodiments, the term "about" encompasses variations of ±2% of the numerical value of the number. In certain embodiments, the term "about" encompasses variations of ±1% of the numerical value of the number.

All numerical ranges herein include all numerical values and ranges of all numerical values within the recited range of numerical values. As a non-limiting example, ($C_1$-$C_6$) alkyls also include any one of $C_1$, $C_2$, $C_3$, $C_4$, $C_5$, $C_6$, ($C_1$-$C_2$), ($C_1$-$C_3$), ($C_1$-$C_4$), ($C_1$-$C_5$), ($C_2$-$C_3$), ($C_2$-$C_4$), ($C_2$-$C_5$), ($C_2$-$C_6$), ($C_3$-$C_4$), ($C_3$-$C_5$), ($C_3$-$C_6$), ($C_4$-$C_5$), ($C_4$-$C_6$), and ($C_5$-$C_6$) alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

The present teachings generally provide Pt(IV)M compounds and/or Pt(IV)M conjugates, compositions, and methods of using the compounds, conjugates or compositions.

Compounds

In various embodiments provided herein, a platinum (IV) (Pt(IV)) compound includes a suitable reacting group for reacting with a functional group on a protein, engineered protein, antibody, antibody fragment, peptide, agonist, antagonist, aptamer or ligand which may be capable of recognizing a selected target cell population, and/or derivatives/analogs/mimics thereof. The reacting group possesses protein-conjugating properties, i.e., it binds covalently to the protein. For example, the reacting group can be introduced by a linker between the reacting group and platinum. In various embodiments, one of or both the axial positions of platinum each comprises one or more reacting groups.

In some embodiments, the protein is albumin and/or derivatives/analogs/mimics thereof.

In some embodiments, the reacting group is a Michael acceptor such as maleimide.

In some embodiments, a compound of the present teachings has Formula I:

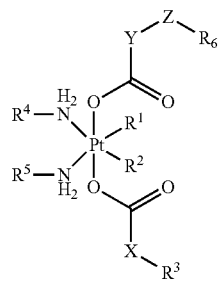

I or a pharmaceutically acceptable salt thereof, wherein:
X and Y are independently selected from NH, alkyl and aryl;
$R^1$ and $R^2$ each is Cl, or $R^1$ and $R^2$ are joined to form an oxalate;
$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl;
$R^4$ and $R^5$ are each H or together constitute a cyclohexyl ring;
Z is alternatively absent or alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl; and $R^6$ is a suitable reacting group for reacting with amino groups, hydroxyl groups or thiol groups, forming a conjugate with a protein, engineered protein, antibody, antibody fragment, peptide, agonist, antagonist, aptamer or ligand which may be capable of recognizing a selected target cell population, and/or derivatives/analogs/mimics thereof, and weherein $R^6$ is selected from any of the following groups:

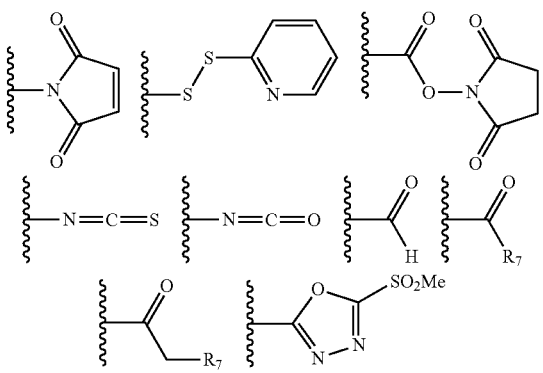

where $R^7$ is Cl, Br, F, mesylate, tosylate, O-(4-nitrophenyl), O-pentafluorophenyl. The reacting group can also be an activated disulfide group, a vinylcarbonyl group, a vinyl acetylene group, an epoxide, an aziridine group or an acetylene group. The groups may be substituted, where appropriate.

An embodiment of the invention is a compound or a pharmaceutically acceptable salt thereof wherein X together with $R^3$ is selected from the group consisting of:

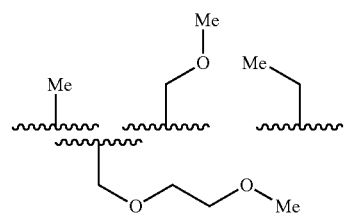

In some embodiments, the reacting group may comprise a maleimide. Such compounds may be referred to herein as "monomaleimide compounds", i.e., Pt(IV)M monomaleimide compounds. As used herein, "monomaleimide compounds" are compounds with a single maleimide group. The monomaleimide compound has Formula II:

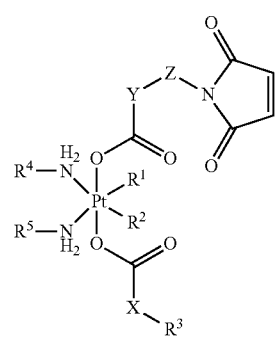

II or a pharmaceutically acceptable salt thereof, wherein:

X and Y are independently selected from NH, alkyl and aryl; $R^1$ and $R^2$ each is Cl, or $R^1$ and $R^2$ are joined to form an oxalate;

$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl;

$R^4$ and $R^5$ are each H or together constitute a cyclohexyl ring; and

Z is alternatively absent or alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

Not willing to be bound to any theory, the unsymmetrical nature of Pt(IV)M monomaleimide compounds allows for the modulation of platinum drug release.

Another embodiment of the invention is a maleimide compound or a pharmaceutically acceptable salt thereof wherein Y together with Z and the maleimide is selected from the group consisting of:

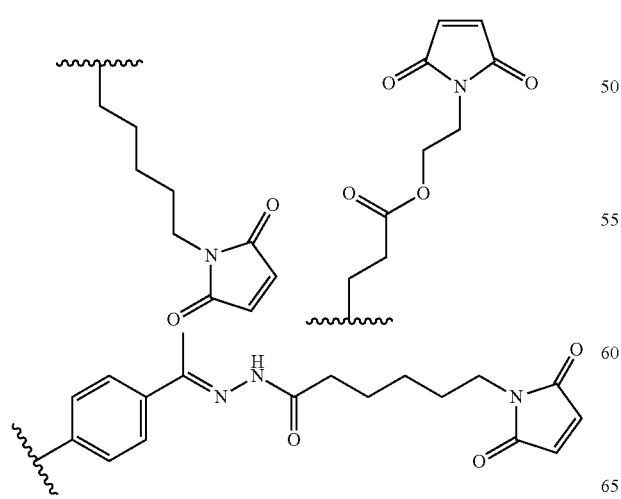

Another embodiment of the invention is a maleimide compound having Formula IIa:

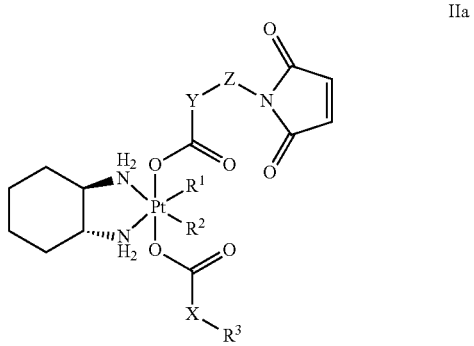

or a pharmaceutically acceptable salt thereof, wherein:

X and Y are independently selected from NH, alkyl and aryl; $R^1$ and $R^2$ each is Cl, or $R^1$ and $R^2$ are joined to form an oxalate;

$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl; and Z is alternatively absent or alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

Another embodiment of the invention is a maleimide compounds having Formular IIb:

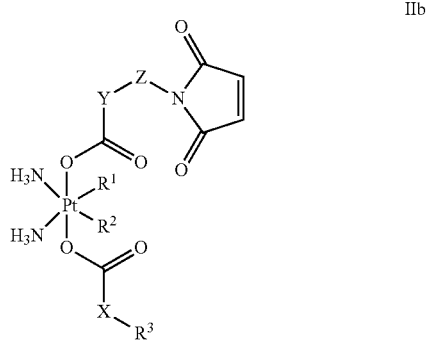

or a pharmaceutically acceptable salt thereof, wherein:

X and Y are independently selected from NH, alkyl and aryl;
$R^1$ and $R^2$ each is Cl, or $R^1$ and $R^2$ are joined to form an oxalate;
$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl; and Z is alternatively absent or alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

A non-limiting example of a Pt(IV)M compound of the invention is a compound selected from the group consisting of the compounds listed:

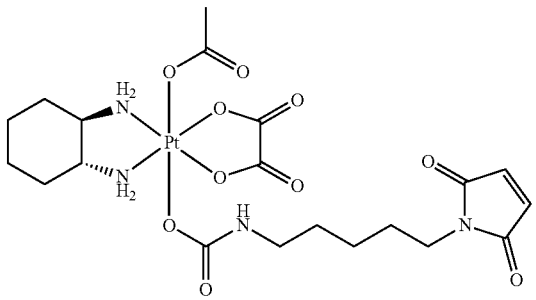

1

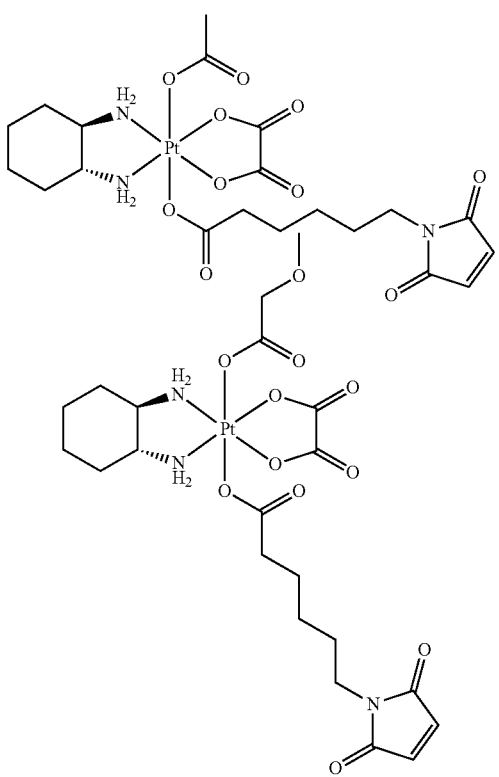

2

-continued

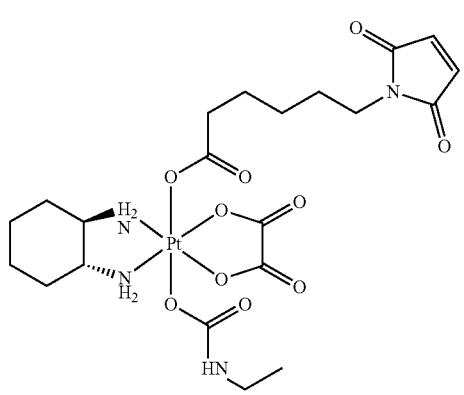

3

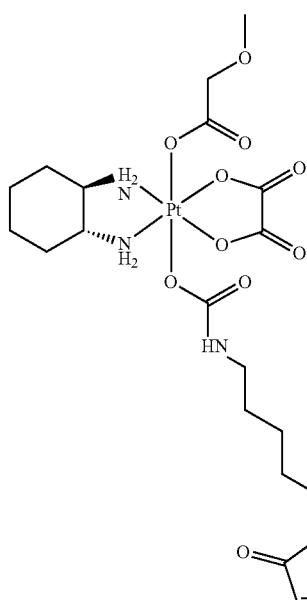

4, 5

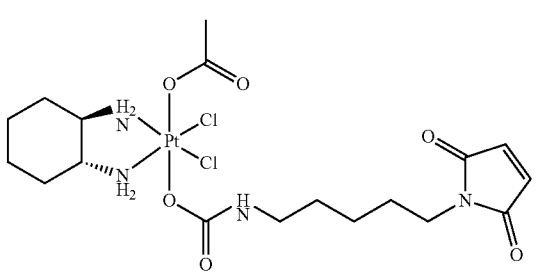

6

27
-continued
7
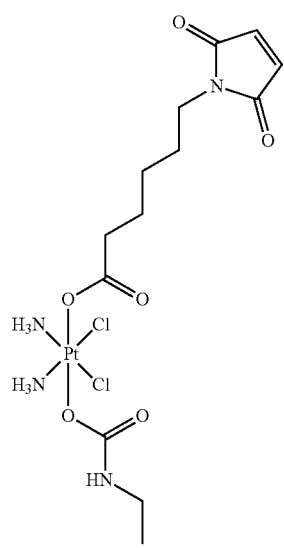
8
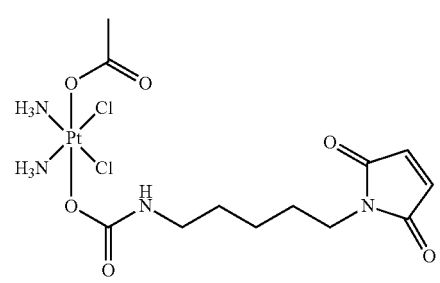
9
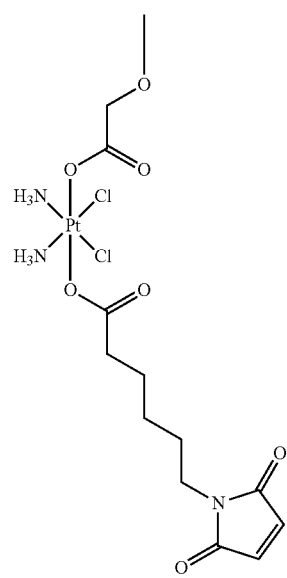
28
-continued
10
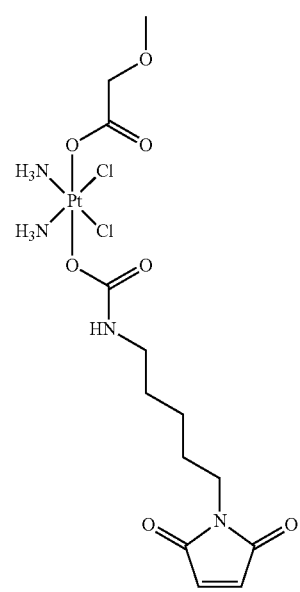
11
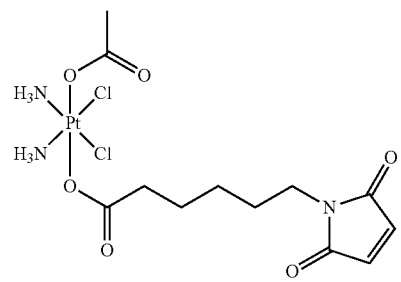
12
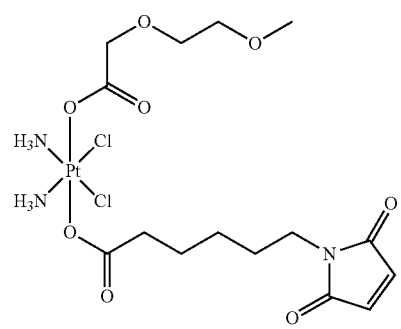

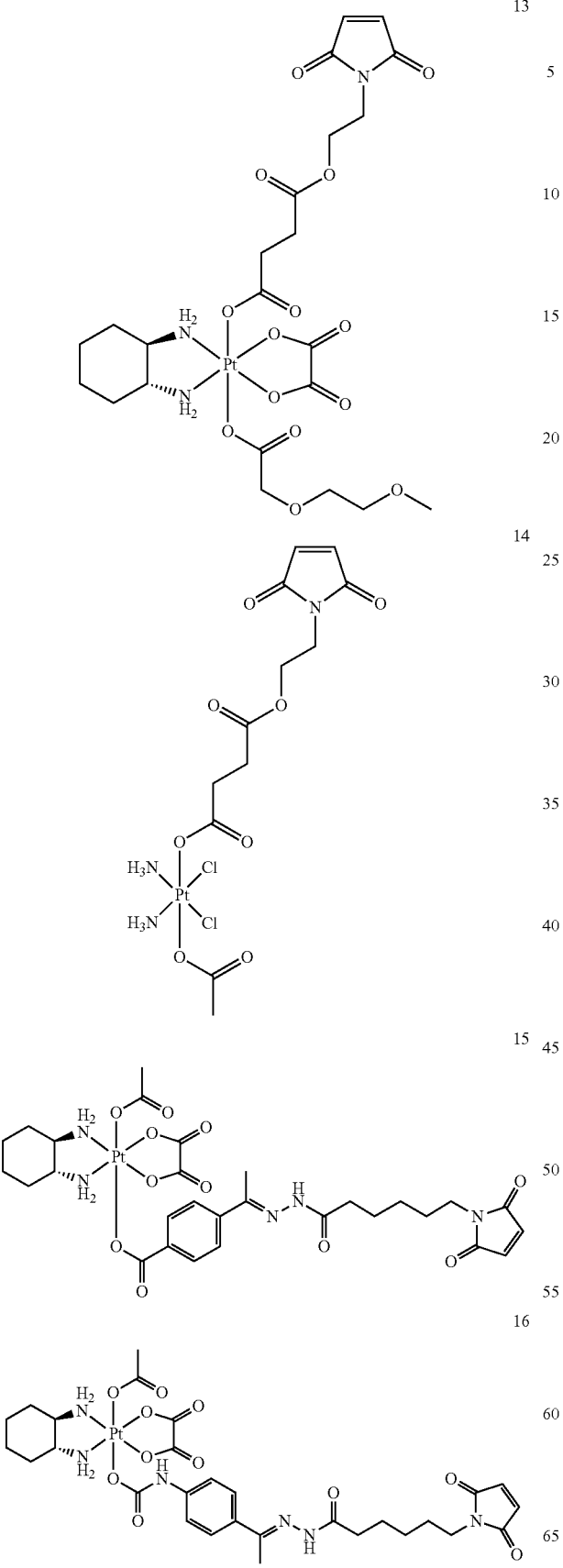
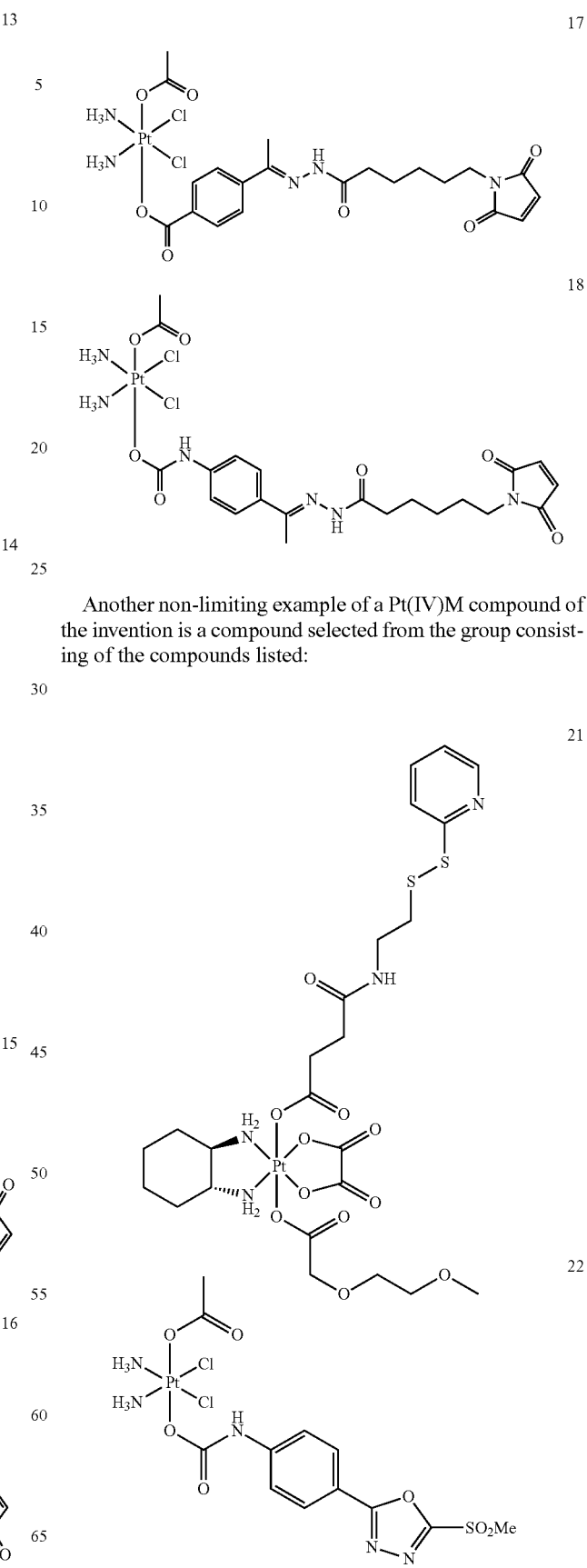
Another non-limiting example of a Pt(IV)M compound of the invention is a compound selected from the group consisting of the compounds listed:

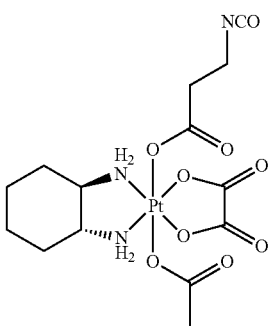

23

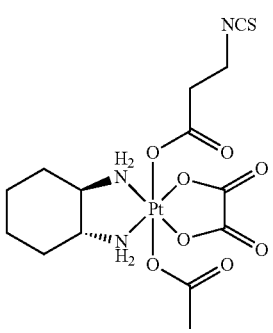

24

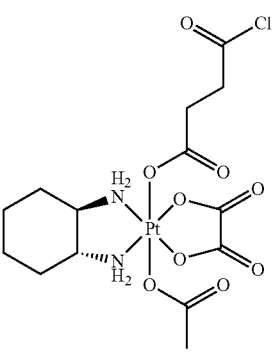

25

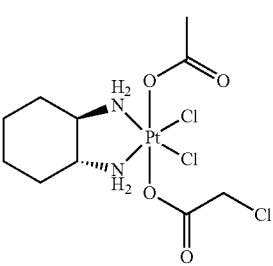

26

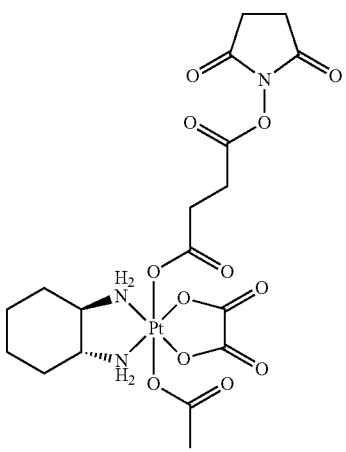

27

As described herein, some compounds of the present teachings may be provided as a salt comprising a charged platinum complex and a counter ion, including a pharmaceutically acceptable counter ion. The counter ion may be a weak or non-nucleophilic stabilizing ion, having a charge of (−1), (−2), (−3), (+1), (+2), (+3), etc. In some embodiments, the counter ion has a charge of (−1). In other embodiments, the counter ion has a charge of (−2). In some embodiments, the counter ion has a charge of (+1). In other embodiments, the counter ion has a charge of (+2).

The present teachings further comprise compositions (including pharmaceutical compositions) each comprising one or more of the compounds as described herein, and at least one pharmaceutically acceptable excipient.

Formulation, Delivery, Administration, and Dosing

In some embodiments, compositions are administered to humans, human patients or subjects. For the purposes of the present disclosure, the phrase "active ingredient" generally refers to the Pt(IV)M compounds and/or Pt(IV)M conjugates to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

The Pt(IV)M compounds and/or Pt(IV)M conjugates of the present invention can be formulated using one or more excipients to: (1) increase stability; (2) permit the sustained or delayed release (e.g., from a depot formulation of the Pt(IV)M compounds and/or Pt(IV)M conjugates); (3) alter the biodistribution (e.g., target the Pt(IV)M compounds and/or Pt(IV)M conjugates to specific tissues or cell types); (4) alter the release profile of the Pt(IV)M compounds and/or Pt(IV)M conjugates in vivo. Non-limiting examples of the excipients include any and all solvents, dispersion media, diluents, or other liquid vehicles, dispersion or suspension aids, surface active agents, isotonic agents, thickening or emulsifying agents, and preservatives. Excipients of the present invention may also include, without limitation, lipidoids, liposomes, lipid nanoparticles, polymers, lipoplexes, core-shell nanoparticles, peptides, proteins, hyaluronidase, nanoparticle mimics and combinations thereof. Accordingly, the formulations of the invention may include one or more excipients, each in an amount that together increases the stability of the Pt(IV)M compounds and/or Pt(IV)M conjugates.

In some embodiments, the pH value of the pharmaceutical composition is between about 4 to about 7, between 4 and 6, between 4 and 5, about 4, about 5, about 6 or about 7.

Excipients

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006; incorporated herein by reference in its entirety) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEENn®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOX- AMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof Excipients such as cocoa butter and suppository waxes, coloring agents, coating agents, sweetening, flavoring, and/or perfuming agents can be present in the composition, according to the judgment of the formulator.

Administration

The Pt(IV)M compounds and/or Pt(IV)M conjugates of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier.

Dosing

The present invention provides methods comprising administering Pt(IV)M compounds and/or Pt(IV)M conjugates to a subject in need thereof. Pt(IV)M compunds as described herein may be administered to a subject using any amount and any route of administration effective for preventing or treating or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like.

Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

As used herein, a "split dose" is the division of single unit dose or total daily dose into two or more doses, e.g, two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the Pt(IV)M compounds and/or Pt(IV)M conjugates of the present invention are administed to a subject in split doses. The Pt(IV)M compounds and/or Pt(IV)M conjugates may be formulated in buffer only or in a formulation described herein.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous).

Liquid Dosage Forms

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions may be mixed with solubilizing agents such as CREMOPHOR®, alcohols, oils, modified oils, glycols, polysorbates, cyclodextrins, polymers, and/or combinations thereof.

Injectable

Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it may be desirable to slow the absorption of the active ingredient from subcutaneous or intramuscular injection. This may be accomplished by the use of a liquid suspension of crystalline or amorphous material with poor water solubility. The rate of absorption of the Pt(IV)M compounds and/or Pt(IV)M conjugates then depends upon its rate of dissolution which, in turn, may depend upon crystal size and crystalline form. Alternatively, delayed absorption of a parenterally administered Pt(IV)M compound and/or Pt(IV)M conjugates may be accomplished by dissolving or suspending the monomalimide in an oil vehicle. Injectable depot forms are made by forming microencapsule matrices of the Pt(IV)M compounds and/or Pt(IV)M conjugates in biodegradable polymers such as polylactide-polyglycolide. Depending upon the ratio of Pt(IV)M compounds and/or Pt(IV)M conjugates to polymer and the nature of the particular polymer employed, the rate of Pt(IV)M compound and/or Pt(IV)M conjugates release can be controlled. Examples of other biodegradable polymers include, but are not limited to, poly(orthoesters) and poly (anhydrides). Depot injectable formulations may be prepared by entrapping the Pt(IV)M compounds and/or Pt(IV)M conjugates in liposomes or microemulsions which are compatible with body tissues.

Pulmonary

Formulations described herein as being useful for pulmonary delivery may also be used for intranasal delivery of a pharmaceutical composition. Another formulation suitable for intranasal administration may be a coarse powder comprising the active ingredient and having an average particle from about 0.2 um to 500 um. Such a formulation may be administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, contain about 0.1% to 20% (w/w) active ingredient, where the balance may comprise an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Pharmaceutical Compositions and Methods of Use

Embodiments of the present teachings also relate to treating a hyperproliferative disorder, cancer and/or a tumor according to any of the techniques and compositions and combinations of compositions described herein.

In various embodiments, methods for treating a subject having a cancer are provided, wherein the method comprises administering a therapeutically-effective amount of a Pt(IV)M compound and/or Pt(IV)M conjugate, as described herein, to a subject having a cancer, suspected of having cancer, or having a predisposition to a cancer. According to the present invention, cancer embraces any disease or malady characterized by uncontrolled cell proliferation, e.g., hyperproliferation. Cancers may be characterized by tumors, e.g., solid tumors or any neoplasm.

In some embodiments, the subject may be otherwise free of indications for treatment with the Pt(IV)M compound and/or Pt(IV)M conjugate. In some embodiments, methods include use of cancer cells, including but not limited to mammalian cancer cells. In some instances, the mammalian cancer cells are human cancer cells.

In some embodiments, the Pt(IV)M compound and/or Pt(IV)M conjugate of the present teachings have been found to inhibit cancer and/or tumor growth. They may also reduce cell proliferation, invasiveness, and/or metastasis, thereby rendering them useful for the treatment of a cancer.

In some embodiments, the Pt(IV)M compound and/or Pt(IV)M conjugate of the present teachings may be used to prevent the growth of a tumor or cancer, and/or to prevent the metastasis of a tumor or cancer. In some embodiments, compositions of the present teachings may be used to shrink or destroy a cancer.

In some embodiments, a Pt(IV)M compound and/or Pt(IV)M conjugate provided herein is useful for inhibiting proliferation of a cancer cell. In some embodiments a compound provided herein is useful for inhibiting cellular proliferation, e.g., inhibiting the rate of cellular proliferation, preventing cellular proliferation, and/or inducing cell death. In general, a compound as described herein can inhibit cellular proliferation of a cancer cell or both inhibiting proliferation and/or inducing cell death of a cancer cell.

The cancers treatable by methods of the present teachings generally occur in mammals. Mammals include, for example, humans, non-human primates, dogs, cats, rats, mice, rabbits, ferrets, guinea pigs horses, pigs, sheep, goats, and cattle. In various embodiments, the cancer is lung cancer, e.g., small cell lung cancer, non-small cell lung cancer, squamous cell lung cancer, breast cancer, non-BRCA-associated breast cancer, colorectal cancer, colon cancer, ovarian cancer, pancreatic cancer, bladder cancer, prostate cancer, cervical cancer, renal cancer, leukemia, central nervous system cancers, myeloma, melanoma, mesothelioma, stomach cancer, rectal cancer, cancer of the large intestine, cancer of the small intestine, esophageal cancer, uterine cancer, head and neck cancer, endometrial cancer, eye cancer, thyroid cancer, testicular cancer, bile duct cancer, liver cancer, kidney cancer, pituitary cancer, lymphoma, brain cancer, glioma, glioblastoma multiforme, meningioma, medulloblastoma, astrocytoma, neuroblastoma, basal cell carcinoma of the skin, sarcoma, synovial sarcoma, rhabdomyosarcoma, leiomyosarcoma, chondrosarcoma, and fibrosarcoma. In some embodiments, the cancer is lung cancer. In certain embodiments, the cancer is human lung carcinoma, ovarian cancer, pancreatic cancer or colorectal cancer including mutant BRCA1 and/or mutant BRCA2 or non-BRCA-associated forms of these cancers.

In some embodiments, the Pt(IV)M compound and/or Pt(IV)M conjugate of the present teachings may be administered to the cancer cells having BRCA1 mutations, BRCA2 mutations, ERCC1 or ERCC2 mutations, mutations in the fanconi anemia genes, MLH1, MSH2, PTEN, Mutations in genes that code for proteins involved in DNA repair, mutations in genes that code for proteins involved in non-homologous DNA repair, mutations in genes that code for proteins involved in nucleotide excision repair, mutations in genes that code for proteins involved in DNA mismatch repair, genetic tests that identify tumors that have a defect in DNA repair, changes in the expression of genes involved in DNA repair such as ERCC1 or ERCC2, and so on. The mutations may be germline or somatic.

In another aspect, the Pt(IV)M compound and/or Pt(IV)M conjugate of the present teachings may be administered to cells with increased albumin uptake, for example, but not limited to, cells with mutations that increase micropinocytosis, cells with mitogen activated kinase pathway mutations, cells with KRAS mutations, cells with BRAF mutations, cells with RAC mutations, cells with RAS overexpression, cells with RAC1 activation, or cells with CDC42 activation.

In some embodiments, cells with increased albumin update may be identified with imaging techniques. For example, a contrast agent is administered to a patient and the level of accumulation of the contrast agent at a tumor site is measured with an imaging technique. The imaging technique may be ultrasound, X-ray, single-photon emission tomography/computed tomography (SPECT/CT), positron emission tomography/computed tomography (PET/CT), magnetic resonance imaging (MRI), computed tomography (CT), single-photon emission tomography (SPECT), fluorescence tomography, and fluorescence spectroscopy.

In yet another aspect, the Pt(IV)M compound and/or Pt(IV)M conjugate of the present teachings may be administered to tumors with a high level of enhanced permeability and retention (EPR) effect. In some embodiments, tumors with a high level of enhanced permeability and retention effect may be identified with imaging techniques. As a non-limited example, iron oxide nanoparticle magnetic resonance imaging may be administered to a patient and EPR effects are measured.

In some embodiments, the Pt(IV)M compound and/or Pt(IV)M conjugate of the present teachings may be administered to a subject selected with the method disclosed in WO2015017506, the contents of which are incorporated herein by reference in their entirety, the method comprising:
(a) administering a contrast agent to the subject;
(b) measuring the level of accumulation of the contrast agent at at least one intended site of treatment; and
(c) selecting the subject based on the level of the accumulation of the contrast agent; wherein the intended site of treatment is a tumor.

Kits and Devices

The invention provides a variety of kits and devices for conveniently and/or effectively carrying out methods of the present invention. Typically kits will comprise sufficient amounts and/or numbers of components to allow a user to perform multiple treatments of a subject(s) and/or to perform multiple experiments.

In one embodiment, the present invention provides kits for inhibiting tumor cell growth in vitro or in vivo, comprising a Pt(IV)M compound and/or Pt(IV)M conjugate of the present invention or a combination of Pt(IV)M compounds and/or Pt(IV)M conjugates of the present invention, optionally in combination with any other active agents.

The kit may further comprise packaging and instructions and/or a delivery agent to form a formulation composition. The delivery agent may comprise a saline, a buffered solution, or any delivery agent disclosed herein. The amount of each component may be varied to enable consistent, reproducible higher concentration saline or simple buffer formulations. The components may also be varied in order to increase the stability of Pt(IV)M compounds and/or Pt(IV)M conjugates in the buffer solution over a period of time and/or under a variety of conditions.

The present invention provides for devices which may incorporate Pt(IV)M compounds and/or Pt(IV)M conjugates of the present invention. These devices contain in a stable formulation available to be immediately delivered to a subject in need thereof, such as a human patient. In some embodiments, the subject has cancer.

Non-limiting examples of the devices include a pump, a catheter, a needle, a transdermal patch, a pressurized olfactory delivery device, iontophoresis devices, multi-layered microfluidic devices. The devices may be employed to deliver Pt(IV)M compounds and/or Pt(IV)M conjugates of the present invention according to single, multi- or split-dosing regiments. The devices may be employed to deliver Pt(IV)M compounds and/or Pt(IV)M conjugates of the present invention across biological tissue, intradermal, subcutaneously, or intramuscularly. More examples of devices suitable for delivering Pt(IV)M compounds and/or Pt(IV)M conjugates include but not limited to a medical device for intravesical drug delivery disclosed in International Publication WO 2014036555, a glass bottle made of type I glass disclosed in US Publication No. 20080108697, a drug-eluting device comprising a flim made of a degrable polymer and an active agent as disclosed in US Publication No. 20140308336, an infusion device having an injection micropump, or a container containing a pharmaceutically stable preparation of an active agent as disclosed in U.S. Pat. No. 5,716,988, an implantable device comprising a reservoir and a channeled member in fluid communication with the reservoir the as disclosed in International Publication WO 2015023557, a hollow-fibre-based biocompatible drug delivery device with one or more layers as disclosed in US Publication No. 20090220612, an implantable device for drug delivery including an elongated, flexible device having a housing defining a reservoir that contains a drug in solid or semi-solid form as disclosed in International Publication WO 2013170069, a bioresorbable implant device disclosed in U.S. Pat. No. 7,326,421, contents of each of which are incorporated herein by reference in their entirety.

It will be appreciated that the following examples are intended to illustrate but not to limit the present invention. Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

EXAMPLES

Example 1

Description of HPLC Analytical Methods

Analysis of the Products by C18 Reverse Phase HPLC (Method A)

The HPLC analysis was carried out on SunFire™ C18 reverse phase column (4.6×50 mm, 3.5 µm) (Waters Corp., Millford, Mass.) with a mobile phase consisting of water+ 0.01% TFA (solvent A) and acetonitrile+0.01% trifluoroacetic acid (TFA) (solvent B) at a flow rate of 2.0 mL/minute and column temperature of 50° C. The injection volume was 10 µL and the analyte was detected using UV at 220 and 254 nm. The initial gradient was 5% solvent B, increased to 95% solvent B within 1.4 minutes, then maintained at 95% solvent B for 1.6 minutes. All solvents were HPLC grade.

Analysis of the Product by C18 Reverse Phase HPLC (RPHPLC) (Method B).

RPHPLC analysis was carried out on Zorbax® Eclipse XDB-C18 reverse phase column (4.6×100 mm, 3.5 µm, Agilent PN: 961967-902, Agilent Technologies, Santa Clara, Calif.) with a mobile phase consisting of water+0.1% TFA (solvent A) and acetonitrile+0.1% TFA (solvent B) at a flow rate of 1.5 mL/minute and column temperature of 35° C. The injection volume was 10 µL and the analyte was detected using UV at 220 and 254 nm. The initial gradient was 5% solvent B, increased to 95% solvent B within 6 minutes, and

Example 2

Synthesis of Acetate 6-(2,5-dioxo-2H-pyrrol-1(5H)-yl) Hexanoate Oxaliplatin

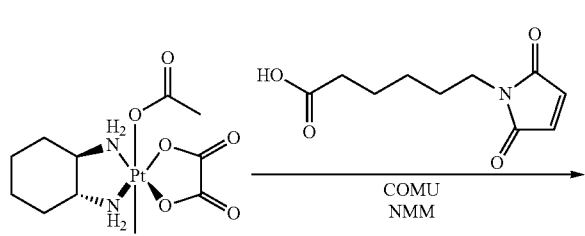

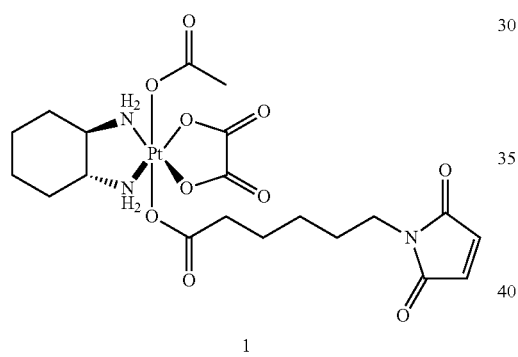

1

Hydroxy (acetoxy) oxaliplatin (150 mg, 0.317 mmol, 1.0 equiv), 6-(2,5-Dioxo-2,5-dihydro-1H-pyrrol-1-yl)hexanoic acid (73.6 mg, 0.349 mmol, 1.10 equiv) and 1-cyano-2-ethoxy-2-oxoethylidenaminooxy)dimethylamino-morpholino-carbenium hexafluorophosphate (COMU®) (149 mg, 0.349 mmol, 1.10 equiv) were mixed in dimethylformamide (DMF) (6.3 mL) and N-methylmorpholine (38 μL, 0.349 mmol, 1.1 equiv) was added. The reaction mixture was stirred at room temperature for 2 hours. The reaction was then concentrated to dryness and the residue was loaded directly onto a C18 column (30 g) eluting with 0-30% MeCN/$H_2O$ gradient over 15 minutes. Fractions containing the product were concentrated on a rotavap before the residue was triturated in $CH_2Cl_2$ and methyl tert-butyl etherTBME, yielding a yellow solid. The product was re-submitted to purification using a silica gel column (4 g), eluted with 0-10% MeOH/$CH_2Cl_2$ gradient over 15 minutes. Fractions containing the product were combined, concentrated, diluted with MeCN/$H_2O$ and lyophilized to provide the product as a white solid (24.0 mg, 11% yield, 97% pure); $^1$H NMR (500 MHz, $D_2O$) δ 8.92-8.37 (m, 4H), 7.01 (s, 2H), 3.46-3.41 (m, 2H), 2.92-2.80 (m, 2H), 2.37-2.29 (m, 2H), 2.27-2.21 (m, 2H), 1.94 (s, 3H), 1.67-1.56 (m, 4H), 1.55-1.45 (m, 4H), 1.33-1.26 (m, 2H), 1.26-1.20 (m, 2H); HPLC-MS 97%. m/z for $C_{20}H_{29}N_3O_{10}Pt$ [(M+1)+]=667.3.

Example 3

Synthesis of a Pt(IV)M Monomaleimide, Compound 2

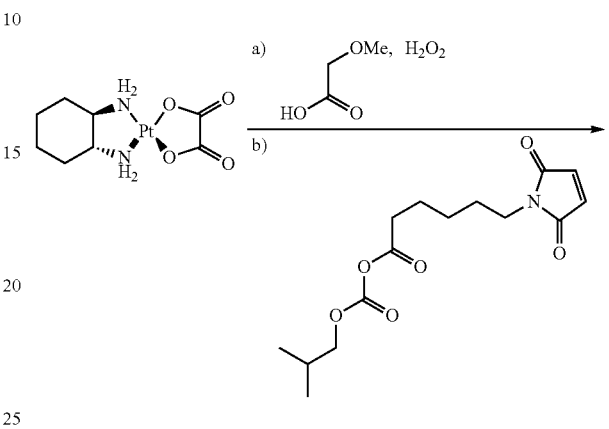

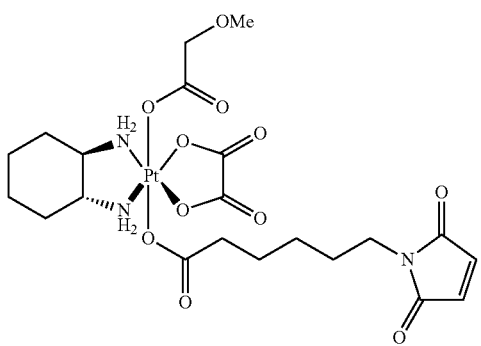

2

Step 1: Oxaliplatin (300 mg, 0.76 mmol, 1.0 equiv) was suspended in methoxyacetic acid (3.40 g, 37.8 mmol, 50 equiv), then hydrogen peroxide (30% w/w in water, 0.13 mL, 3.8 mmol, 5.0 equiv) was added and solution was stirred for 1 hour. Diethyl ether was added and resulting precipitate was filtered and dried to afford a white solid (400 mg).

Step 2: 6-maleimidohexanoic acid (126 mg, 0.596 mmol, 1.0 equiv) was suspended in tetrahydrofuran (THF) (5 mL) then 4-methyl morpholine (65 μL, 0.596 mmol, 1.0 equiv) was added followed by isobutyl chloroformate (77 μL, 0.596 mmol, 1.0 equiv). The solution was stirred at room temperature for 1 hour, then water (10 mL) and EtOAc (10 mL) were added and the layers were separated. The organic layer was concentrated on a rotavap to dryness. The methoxyacetate hydroxy oxaliplatin (300 mg, 0.596 mmol, 1.00 equiv) was dissolved in DMF (1 mL) then activated ester was added and solution was stirred at room temperature for 2 hours. The crude product was purified by reverse phase chromatography (MeCN/$H_2O$, 0.2% AcOH) to afford the desired product, maintained at 95% solvent B for 2 minutes, then returned to 5% solvent B and maintained for 2 minutes.

which was lyophilized, resulting in a lyophilized powder (115 mg, 28% yield). HPLC/MS (Method A): 1.333 minutes, M+H=696.2, 697.2, 698.3.

Example 4

Synthesis of a Pt(IV)M monomaleimide, Compound 3

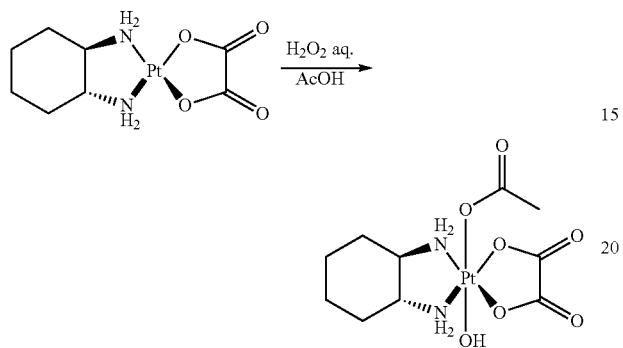

Another example of a compound taught herein was synthesized starting with oxaliplatin (1.0 g, 2.52 mmol, 1 equiv) that was dissolved in acetic acid (6 mL, 100 mmol, 40 equiv) and reacted with 30% $H_2O_2$ (1 mL, 12.6 mmol, 5 equiv). The reaction mixture was covered with aluminium foil and stirred at room temperature for 24 hours. Following this reaction, more acetic acid (3 mL, 50 mmol, 20 equiv) and 30% $H_2O_2$ (1 mL, 12.6 mmol, 5 equiv) were added and the reaction mixture was stirred for an additional 24 hours. The suspension was filtered and the white solid residue was washed with diethylether ($Et_2O$) to yield hydroxy(acetoxy)oxaliplatin (878 mg, 74% yield, 70% pure). $^1$H NMR (500 MHz, DMF-d7) δ 10.42 (brs, 2H), 8.93 (m, 1H), 8.39 (brs, 1H), 7.96 (brs, 1H), 7.26 (brs, 1H), 2.91-2.80 (m, 2H), 2.31-2.22 (m, 2H), 1.98 (s, 3H), 1.89 (s, 3H), 1.73-1.49 (m, 4H), 1.34-1.21 (m, 2H); HPLC-MS 91%, m/z for $C_{10}H_{18}N_2O_7Pt$ [(M+H)$^+$]=474.2.

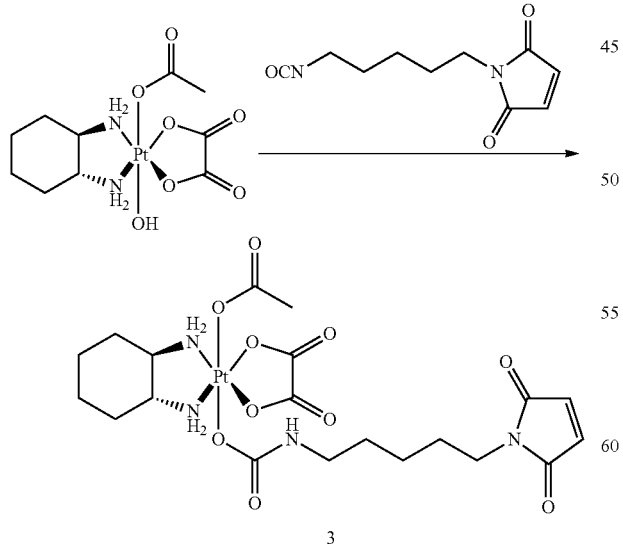

Hydroxy(acetoxy)oxaliplatin (200 mg, 0.422 mmol, 1.0 equiv) and DMF (1.10 mL) were loaded in a round bottom flask. At room temperature, isocyanate (176 mg, 0.845 mmol, 2.0 equiv) in DMF (1.0 mL) was added in one portion and the reaction was stirred at room temperature for 2 hours. HPLC trace demonstrated the reaction to be completed producing also ~30% of bis-addition product due to the presence of bishydroxyoxaliplatin in the starting material. Water (8.0 mL) was added to the reaction mixture and the solution was loaded directly onto a C18 column (60 g). The reaction mixture was purified using a 0-40% MeCN/$H_2O$ gradient over 12 column volumes. The compound eluted at 26% MeCN/$H_2O$. Pure fractions were combined and lyophilized to provide the product as a white solid (157.6 mg, 55%); $^1$H NMR (500 MHz, DMF-d7) δ 10.10 (s, 1H), 8.92-8.63 (m, 2H), 8.35 (s, 1H), 7.07 (t, J=5.6 Hz, 1H), 7.01 (s, 2H), 3.44 (t, J=7.2 Hz, 2H), 3.09-2.95 (m, 2H), 2.90-2.84 (m, 2H), 2.33 (t, J=11.4 Hz, 2H), 1.94 (s, 3H), 1.67-1.14 (m, 12H); HPLC-MS 98.6%. m/z for $C_{20}H_{30}N_4O_{10}Pt$ [(M+1)$^+$]=682.3.

Example 5

Synthesis of a Pt(IV)M monomaleimide, Compound 4

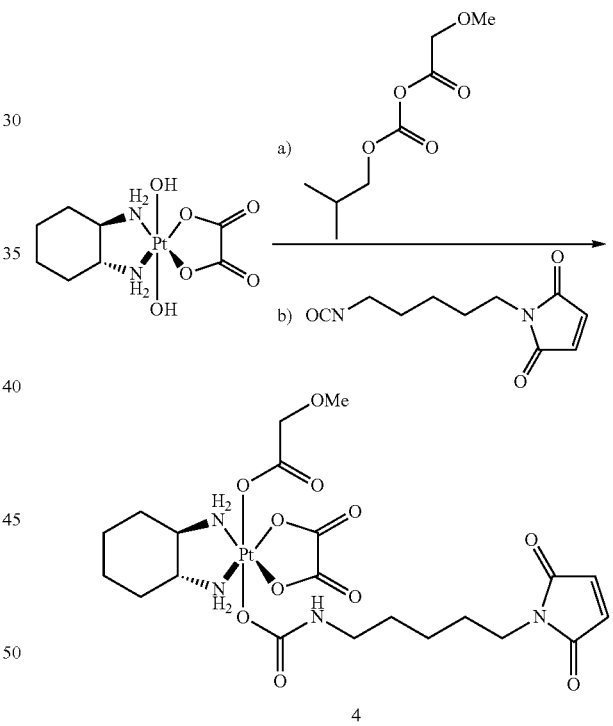

Methoxyacetic acid (42 mg, 0.464 mmol, 1.00 equiv) was suspended in THF (3 mL) then 4-methyl morpholine (51 μL, 0.464 mmol, 1.00 equiv) was added followed by isobutyl chloroformate (60 μL, 0.464 mmol, 1.00 equiv). The solution was stirred at room temperature for 1 hour, then water (5 mL) and EtOAc (5 mL) were added and the layers were separated. The organic layer was concentrated on a rotavap to dryness. Dihydroxyoxaliplatin (200 mg, 0.464 mmol, 1.00 equiv) was suspended in DMSO (4 mL) then the activated ester was added and solution was stirred at room temperature for 3 days. The remaining solid was filtered, then diethyl ether (10 mL) was added to the filtrate and stirred for 5 minutes before layers were separated. Acetone was added (20 mL) to the DMSO layer, which caused a solid to precipitate. After stirring for 5 minutes, the solid was filtered, washed with acetone, and dried under vacuum to afford an off-white solid (105 mg).

2-Methoxyacetate hydroxyl oxaliplatin (105 mg, 0.21 mmol, 1.0 equiv) was dissolved in DMF (1 mL) then 1-(5-isocyanatopentyl)-1H-pyrrole-2,5-dione (65 mg, 0.31 mmol, 1.5 equiv) was added and the solution was stirred at room temperature for 16 hours. The crude product was purified by reverse phase chromatography (MeCN/H$_2$O, 0.2% AcOH) to afford desired product as a lyophilized powder (67 mg). HPLC/MS (Method A): 1.203 minutes, M+H=711.2, 712.2, 713.3.

Example 6

Synthesis of a Pt(IV)M monomaleimide, Compound 5

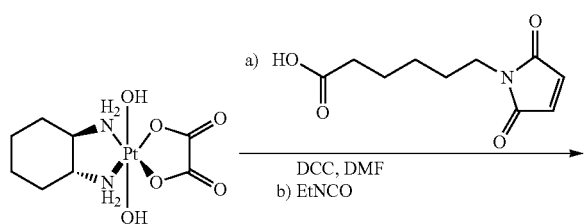

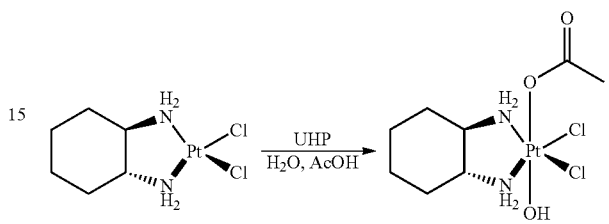

6-maleimidohexanoic acid (844 mg, 4.0 mmol, 2.0 equiv) and dicyclohexylcarbodiimide (DCC) (822 mg, 4.0 mmol, 2.0 equiv) were charged in a vial and dissolved in DMF (10 mL). The solution was stirred for 30 minutes, by which time a precipitate had formed. The solid was filtered, the filtrate was added to dihydroxyoxaliplatin (862 mg, 2.0 mmol, 1.0 equiv) suspended in DMF (10 mL) and solution was stirred at room temperature for 4 hours. The suspension was filtered, then ethyl isocyanate (EtNCO) (206 mL, 4.0 mmol, 2.0 equiv) was added to filtrate and solution was stirred at room temperature for 30 minutes. Solvent was then evaporated and the residue was purified on silica gel (2-7% MeOH/DCM (dichloromethane)). Concentrated pure fractions were dissolved in MeOH (2 mL) and added to TBME (50 mL) to afford a white precipitate that was filtered and dried. The desired product was obtained as a white solid (340 mg). HPLC/MS (Method B): 3.81 minutes, M+H=695, 696, 697.

Example 7

Synthesis of a Pt(IV)M monomaleimide, Compound 6

Hydroxy(acetoxy)(DACH)PtCl$_2$:(DACH)PtCl$_2$ (1.00 g, 2.63 mmol, 1.0 equiv) and urea hydroperoxide (UHP) (1.24 g, 13.15 mmol, 5.0 equiv) were loaded in a round bottom flask. AcOH (13 mL) and H$_2$O (13 mL) were added and the reaction was stirred at room temperature overnight. The yellow solution reaction mixture was then concentrated to dryness. We noted that starting material was still present according to HPLC-MS traces. The crude solid obtained was suspended in about 10 mL of MeOH and DCM was slowly added to obtain a suspension. After stirring for 30 minutes, filtration of the solid over a Buchner funnel provided the desired compound as an off-white solid (410 mg, 34.2%). HPLC-MS 93%, m/z for C$_8$H$_{18}$Cl$_2$N$_2$O$_3$Pt [(M+H)$^+$]=457.2.

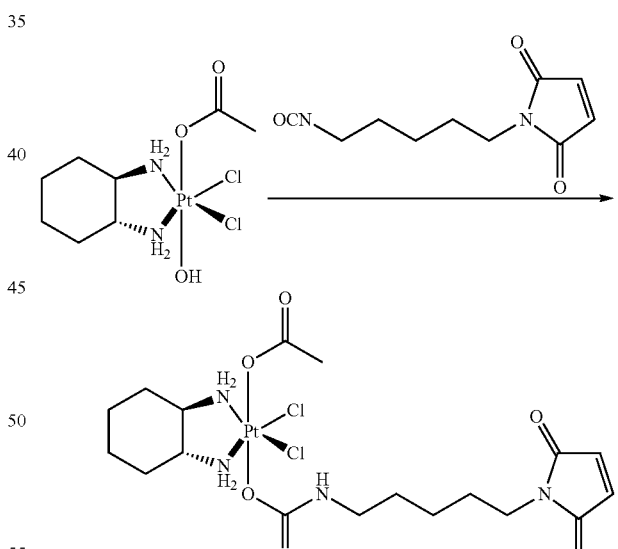

Hydroxy(acetoxy)(DACH)PtCl$_2$ (200 mg, 0.438 mmol, 1.0 equiv) and DMF (3.0 mL) were loaded in a round bottom flask. At room temperature, 1-(5-isocyanatopentyl)-1H-pyrrole-2,5-dione (273 mg, 1.31 mmol, 3.0 equiv) in DMF (1.40 mL) was added in one portion and the reaction stirred at room temperature overnight. The next day, HPLC traces demonstrated the reaction to be completed. The reaction mixture was loaded directly onto a C18 column (60 g) and purified using 0-60% MeCN/H$_2$O gradient over 15 column volumes.

The compound eluted at 32% MeCN/H$_2$O. Pure fractions were combined and lyophilized to provide the product as a white solid (182 mg, 63%). $^1$H NMR (500 MHz, DMF-d7) δ 10.94 (s, 1H), 9.74 (s, 1H), 8.43 (s, 1H), 8.11 (s, 1H), 7.05 (t, J=6.0 Hz, 1H), 7.03-7.00 (m, 2H), 3.47-3.42 (m, 2H), 3.10-2.94 (m, 2H), 2.90-2.80 (m, 1H), 2.44-2.30 (m, 2H), 1.93 (s, 3H), 1.69-1.37 (m, 9H), 1.37-1.15 (m, 4H); HPLC-MS 95.4%, m/z for C$_{18}$H$_{30}$Cl$_2$N$_4$O$_6$Pt [(M+H)$^+$]=665.2.

Example 8

Synthesis of a Pt(IV)M monomaleimide, Compound 7

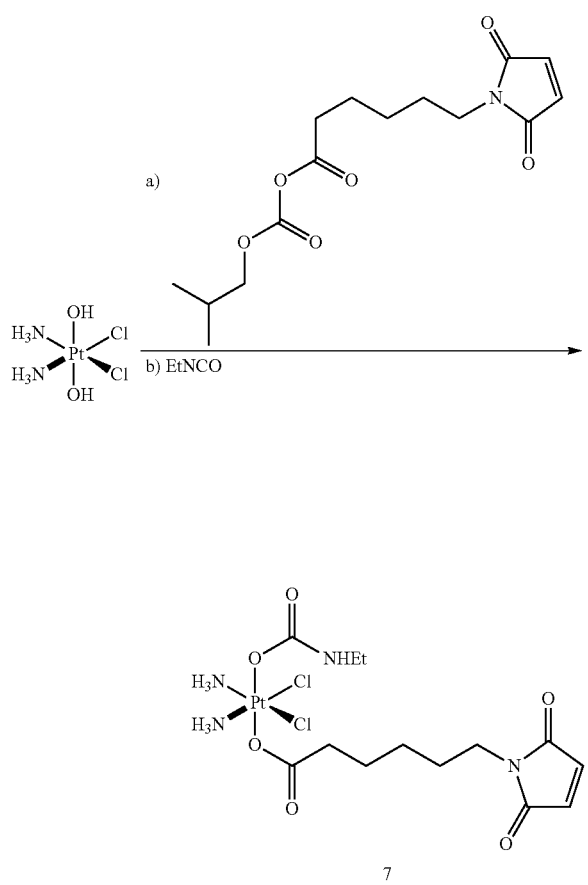

6-Maleimidohexanoic acid (285 mg, 1.35 mmol, 1.00 equiv) was suspended in THF (10 mL) then 4-methyl morpholine (148 μL, 1.35 mmol, 1.00 equiv) was added followed by isobutyl chloroformate (175 μL, 1.35 mmol, 1.00 equiv). The solution was stirred at room temperature for 1 hour, then water (20 mL) and EtOAc (20 mL) were added and layers were separated. Dihydroxy cisplatin (450 mg, 1.35 mmol, 1.00 equiv) was suspended in DMSO (8 mL) then activated ester was added and the solution was stirred at room temperature for 3 days. Ethyl isocyanate (500 μL, 9.7 mmol, 7.0 equiv) was added as a solution in DMF (2 mL) and solution was stirred at room temperature for 1 hour. The product was purified by reverse phase chromatography (MeCN/H$_2$O, 0.2% AcOH) to afford the desired product as a lyophilized powder (160 mg). HPLC/MS (method A): 1.473 minutes, M+H=597.1, 598.1 599.1.

Example 9

Synthesis of a Pt(IV)M monomaleimide, Compound 8

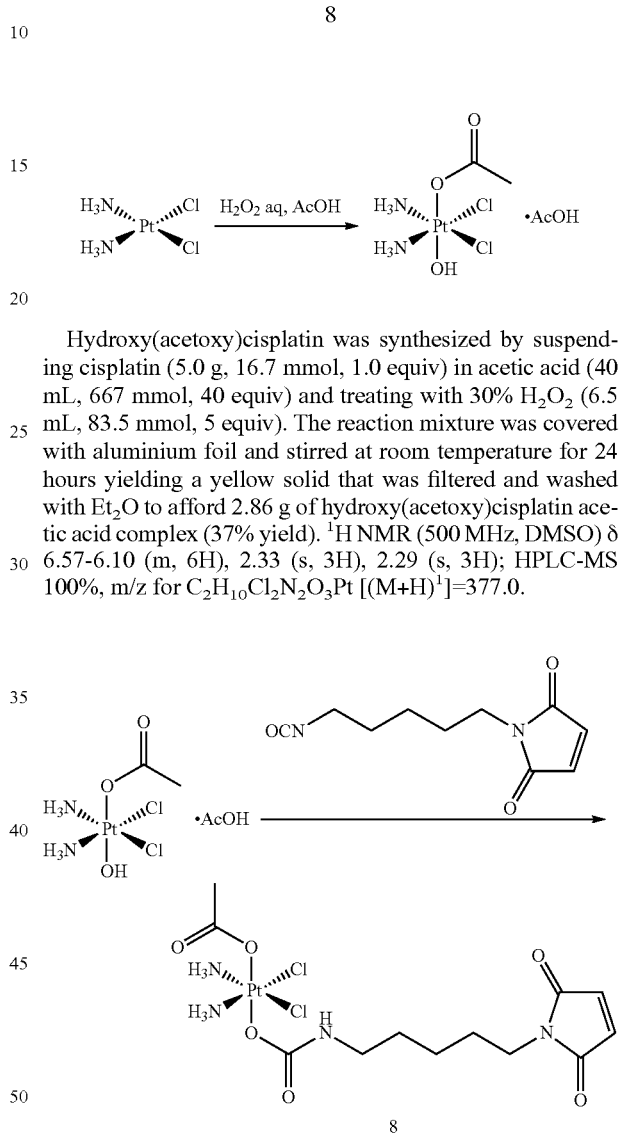

Hydroxy(acetoxy)cisplatin was synthesized by suspending cisplatin (5.0 g, 16.7 mmol, 1.0 equiv) in acetic acid (40 mL, 667 mmol, 40 equiv) and treating with 30% H$_2$O$_2$ (6.5 mL, 83.5 mmol, 5 equiv). The reaction mixture was covered with aluminium foil and stirred at room temperature for 24 hours yielding a yellow solid that was filtered and washed with Et$_2$O to afford 2.86 g of hydroxy(acetoxy)cisplatin acetic acid complex (37% yield). $^1$H NMR (500 MHz, DMSO) δ 6.57-6.10 (m, 6H), 2.33 (s, 3H), 2.29 (s, 3H); HPLC-MS 100%, m/z for C$_2$H$_{10}$Cl$_2$N$_2$O$_3$Pt [(M+H)$^1$]=377.0.

Hydroxy(acetoxy)cisplatin acetic acid complex (100 mg, 0.229 mmol, 1.00 equiv) and DMF (1.0 mL) were loaded in a round bottom flask. At room temperature, 1-(5-isocyanatopentyl)-1H-pyrrole-2,5-dione (111 mg, 0.532 mmol, 2.32 equiv) in DMF (0.8 mL) was then added in one portion and reaction stirred at room temperature overnight. Water (4.0 mL) was added to the reaction mixture and the solution was loaded directly onto a C18 column (60 g). The reaction mixture purified using a 0-80% MeCN/H$_2$O gradient over 15 column volumes. The compound eluted at 30% MeCN/H$_2$O. Pure fractions were combined and lyophilized to provide compound 8 as a white solid (117.0 mg, 87% yield). $^1$H NMR (500 MHz, DMF-d7) δ 7.19-6.75 (m, 9H), 3.45 (t, J=7.2 Hz, 2H), 3.04-2.95 (m, 2H), 1.90 (s, 3H), 1.59-1.50 (m, 2H), 1.49-1.37 (m, 2H), 1.34-1.20 (m, 2H); HPLC-MS 96.7%. m/z for $C_{12}H_{22}Cl_2N_4O_6Pt$ [(M+H)$^+$]=585.2.

Example 10

Synthesis of a Pt(IV)M monomaleimide, Compound 9

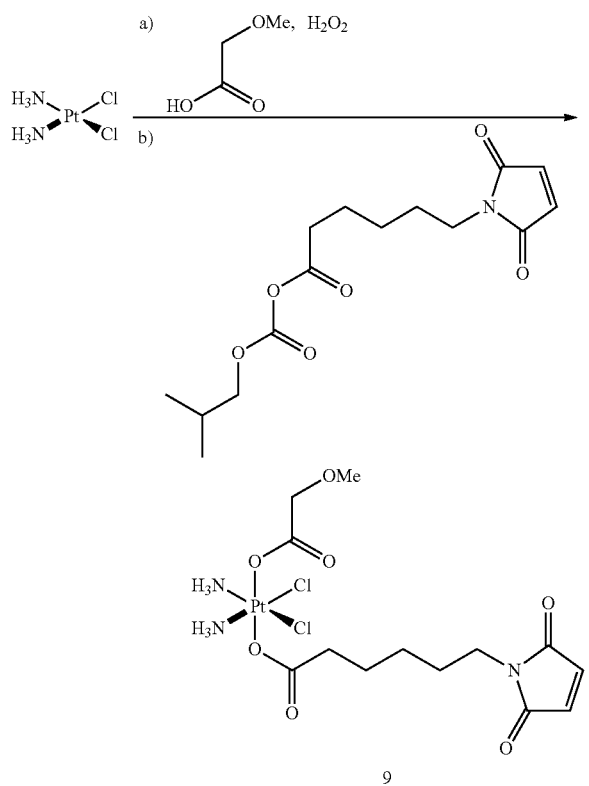

Step 1: Cisplatin (300 mg, 1.00 mmol, 1.00 equiv) was suspended in methoxyacetic acid (4.5 g, 50 mmol, 50 equiv), then hydrogen peroxide (30% w/w in water, 0.57 mL, 5 mmol, 5.0 equiv) was added and the solution was stirred for 2 days. Diethyl ether was then added and the resulting precipitate was filtered and dried to afford a mixture of dimethoxyacetate cisplatin and methoxyacetate hydroxy cisplatin (1.5:1). The white solid (400 mg) was suspended in DMF (10 mL) and used for subsequent steps. To prepare an activated ester, 6-maleimidohexanoic acid (316 mg, 1.5 mmol, 1.0 equiv) was suspended in THF (10 mL) then 4-methyl morpholine (165 μL, 1.5 mmol, 1.0 equiv) was added followed by isobutyl chloroformate (194 μL, 1.5 mmol, 1.0 equiv). The solution was stirred at room temperature for 1 hour, then water (20 mL) and EtOAc (20 mL) were added and the layers were separated. The organic layer was concentrated on a rotavap to dryness. The resulting activated ester was dissolved in DMF (2 mL), added to methoxyacetate hydroxy cisplatin solution and stirred at room temperature for 2 hours then purified by reverse phase chromatography (MeCN/H$_2$O, 0.2% AcOH) to afford the desired product as a lyophilized powder (115 mg). HPLC/MS (method A): 1.199 minutes, M+H=599.0, 600.0, 601.1.

Example 11

Synthesis of a Pt(IV)M monomaleimide, Compound 10

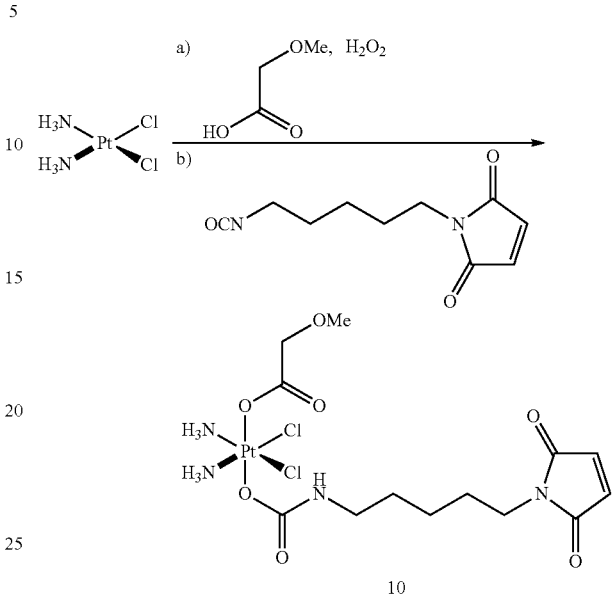

Step 1: Cisplatin (250 mg, 0.83 mmol, 1.00 equiv) was suspended in methoxyacetic acid (3.75 g, 41.7 mmol, 50.0 equiv), then hydrogen peroxide (30% w/w in water, 0.47 mL, 4.17 mmol, 5.0 equiv) was added and solution was stirred for 2 days. Diethyl ether was added and resulting precipitate was filtered and dried to afford a mixture of dimethoxyacetate cisplatin and methoxyacetate hydroxycisplatin (1.5:1). The white solid (350 mg) was dissolved in DMF (1 mL) then isocyanate (260 mg, 1.25 mmol, 1.50 equiv) was added and the solution was stirred at room temperature for 2 hours. Crude product was purified by reverse phase chromatography (MeCN/H2O, 0.2% AcOH) to afford desired product as a lyophilized powder (139 mg). HPLC/MS (Method A): 1.184 minutes, M+H=614.1, 615.1, 616.1.

Example 12

Synthesis of a Pt(IV)M monomaleimide, Compound 11

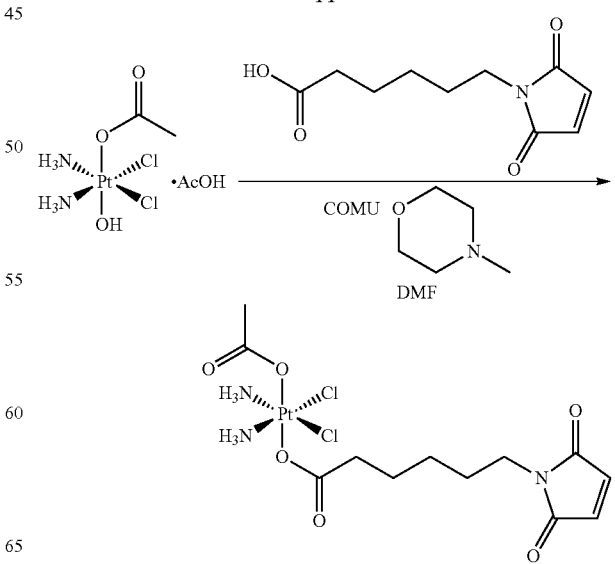

To hydroxy(acetoxy)cisplatin acetic acid complex (200 mg, 0.459 mmol, 1.00 equiv) suspended in DMF (0.035 M, 15 mL) was added 6-maleimidohexanoic acid (130 mg, 0.61 mmol, 1.33 equiv) followed by N-methylmorpholine (67 µL, 0.61 mmol, 1.33 equiv) and COMU peptide coupling reagent (263 mg, 0.61 mmol, 1.33 equiv). The reaction mixture was stirred at room temperature for 15 hours. The resulting clear yellow solution was concentrated under reduced pressure. The resulting residue was diluted in water (20 mL) and washed twice with methyl tertiary-butyl ether (MTBE) (2×15 mL). The aqueous layer was concentrated under reduced pressure to an approximate residual volume of 5 mL. This solution containing the product was injected onto a pre-packed C-18 cartridge (30 g) and eluted on a reverse phase system with a 15-50% (MeCN/water) 15 minute gradient. Pure collected fractions were combined and concentrated under reduce pressure and residual water was removed by lyophilization to afford compound 11 as an off-white solid (119 mg, 46%). $^1$H NMR (500 MHz, DMF-$d_7$) δ (ppm): 7.02 (s, 2H), 7.03-6.67 (m, 6H), 3.44 (t, J=7.3 Hz, 2H), 2.22 (t, J=7.3 Hz, 2H), 1.90 (s, 3H), 1.57-1.46 (m, 4H), 1.31-1.23 (m, 2H). HPLC-MS 99%, m/z for $C_{12}H_{21}Cl_2N_3O_6Pt$ [(M+H)$^+$]= 570.2.

Example 13

Synthesis of a Pt(IV)M monomaleimide, Compound 12

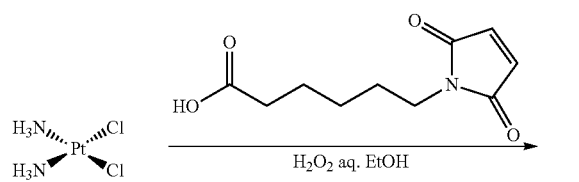

Synthesis of hydroxy(6-(2,5-dioxo-2H-pyrrol-1 (5H)-yl)hexanoate)cisplatin

Cisplatin (200 mg, 0.67 mmol, 1.00 equiv) was suspended in ethanol (1 mL) and was added the 6-(2,5-dioxo-2,5-dihydro-1H-pyrrol-1-yl)hexanoic acid (703 mg, 3.33 mmol, 5.00 equiv) followed by 30% $H_2O_2$ (160 µL, 2.01 mmol, 3.00 equiv). The reaction mixture was covered with aluminum foil and stirred at room temperature for 60 hours. The reaction mixture was concentrated on a rotavap to dryness, dissolved in DMF, loaded directly onto a C18 column (30 g) and eluted with a 0-40% MeCN/$H_2O$ gradient over 15 minutes. Pure fractions were combined and lyophilized to provide hydroxy (6-(2,5-dioxo-2H-pyrrol-1(5H)-yl)hexanoate)cisplatin as a yellow solid (90.4 mg); HPLC-MS m/z for $C_{10}H_{19}Cl_2N_3O_5Pt$ [(M+H)+]=528.2.

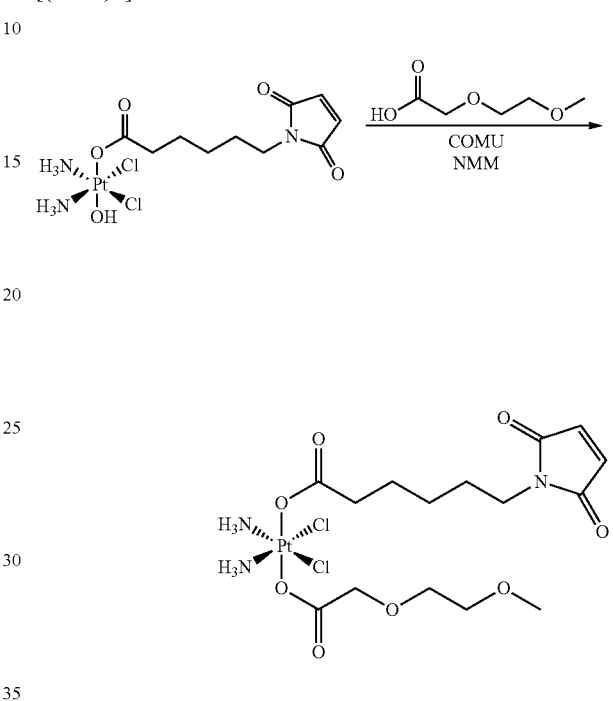

12

Synthesis of 2-(2-Methoxyethoxy)acetate6-(2,5-dioxo-2H-pyrrol-1(5H)-yl)hexanoatecisplatin Hydroxy(6-(2,5-dioxo-2H-pyrrol-1(5H)-yl)hexanoate) cisplatin (140 mg, 0.265 mmol, 1.00 equiv), 3,6-dioxaheptanoic acid (39.0 mg, 0.292 mmol, 1.10 equiv) and COMU (125 mg, 0.292 mmol, 1.10 equiv) were mixed in DMF (5 mL) followed by the addition of N-methylmorpholine (32 µL, 0.29 mmol, 1.1 equiv). The reaction mixture was stirred at room temperature overnight. The reaction mixture was then diluted with water and the aqueous layer was washed with MTBE. The aqueous layer was concentrated to dryness, dissolved in water, loaded directly onto a C18 column (30 g) and eluted using a 0-30% MeCN/$H_2O$ gradient over 15 minutes. Fractions containing the product were concentrated on a rotavap to dryness. The residue was adsorbed on silica gel and purified using a silica gel column (24 g), eluted using 97-70% MeCN/$H_2O$ gradient over 15 minutes. Fractions containing the product were concentrated, the residue was adsorbed on silica gel and purified using a silica gel column (4 g), eluted using 0-10% MeOH/$CH_2Cl_2$ gradient over 15 minutes. Fractions containing the product were concentrated and the residue was diluted with MeCN/$H_2O$ and lyophilized to provide the product, compound 12, as a yellow solid (31.8 mg, 19% yield); $^1$H NMR (500 MHz, $D_2O$) δ 6.85 (s, 2H), 4.26 (s, 2H), 3.75-3.72 (m, 2H), 3.67-3.64 (m, 2H), 3.55-3.50 (m, 2H), 3.40 (s, 3H), 2.45-2.38 (m, 2H), 1.62-1.55 (m, 4H), 1.35-1.25 (m, 2H); HPLC-MS 97%. m/z for $C_{15}H_{27}Cl_2N_3O_8Pt$ [(M+H)+]=644.2.

Example 14

Synthesis of a Pt(IV)M monomaleimide, Compound 13

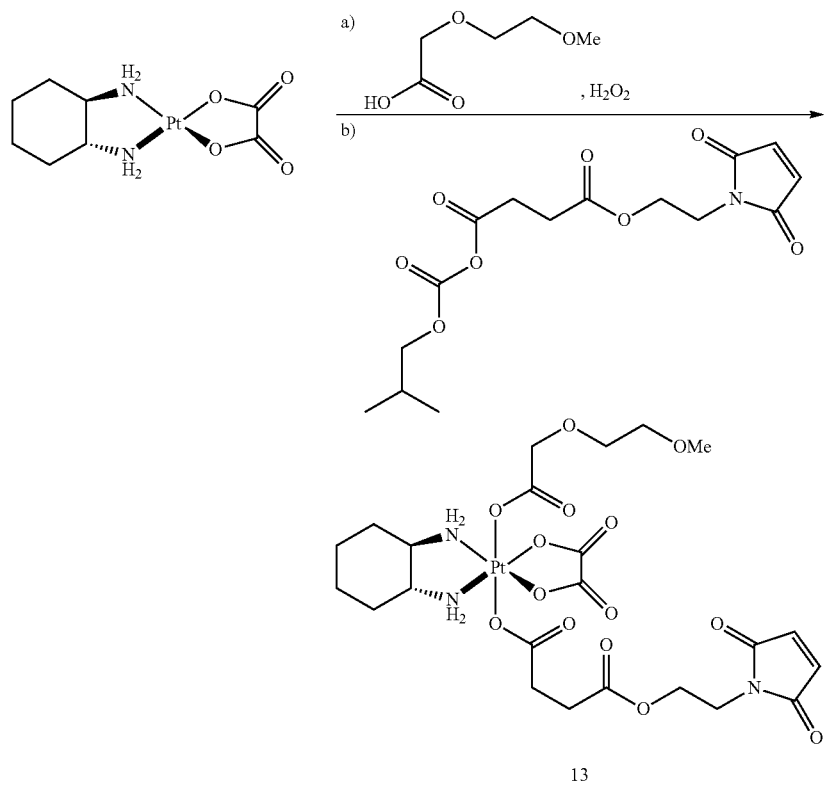

13

Oxaliplatin (2.05 g, 5.00 mmol, 1.00 equiv) was suspended in 2-methoxyethoxyacetic acid (22.7 mL, 200 mmol, 40.0 equiv), then hydrogen peroxide (30% w/w in water, 0.775 mL, 25 mmol, 5.0 equiv) was added and solution was stirred for 16 hours. MTBE (175 mL) was added and the filtrate was decanted. The gummy residue was dissolved in DMF (5 mL) and added dropwise onto EtOAc (125 mL). The resulting precipitate was filtered, rinsed with EtOAc (3×20 mL) and dried under vacuum to afford a white solid (1.75 g). HPLC/MS (method B): 2.29 minutes, M+H=547, 548, 549 and 2.81 minutes, M+H=663, 664, 665. The solid consists of a 1:1 mixture of desired product and bis acylation product and was used in that composition for next step.

2-Hydroxyethyl maleimide (120 mg, 0.85 mmol, 2.00 equiv) was suspended in THF (4.0 mL) then N-methyl morpholine (93 μL, 0.85 mmol, 2.0 equiv) was added followed by succinic anhydride (85 mg, 0.85 mmol, 2.0 equiv). The solution was stirred at room temperature for 16 hours, then N-methyl morpholine (93 μL, 0.85 mmol, 2.0 equiv) was added followed by isobutyl chloroformate (110 μL, 0.85 mmol, 2.0 equiv) and the solution was stirred at room temperature for 45 minutes. Water (10 mL) and ethyl acetate (10 mL) were added and the layers were separated. Solvent was then evaporated, then the activated ester was dissolved in DMF and hydroxy(2-methylethoxyacetoxy)oxalplatin(IV) (233 mg, 0.43 mmol, 1.0 equiv) was added and solution was stirred at 50° C. for 18 hours. Solvent was evaporated from this mixture and the crude product was purified on silica gel (0-8% MeOH/DCM gradient) to afford the desired product with residual MeOH. The residue was dissolved in MeOH (2 mL) and the resulting solution was added to TBME (50 mL) to obtain a white precipitate (compound 13) that was filtered and dried under vacuum. Compound 13 was obtained as an off-white solid (131 mg, 40% yield). HPLC/MS (method B): 3.41 minutes, M+H=771.

Example 15

Synthesis of a Pt(IV)M monomaleimide, Compound 14

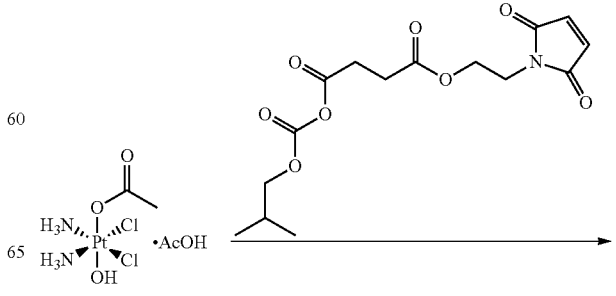

-continued

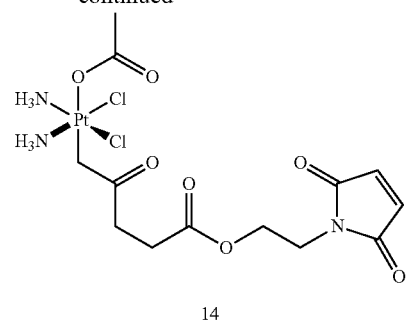

14

2-Hydroxyethyl maleimide (120 mg, 0.85 mmol, 2.3 equiv) was suspended in THF (4.0 mL) then N-methyl morpholine (93 µL, 0.85 mmol, 2.3 equiv) was added followed to succinic anhydride (85 mg, 0.85 mmol, 2.3 equiv). Solution was stirred at room temperature for 16 hours, then N-methyl morpholine (93 µL, 0.85 mmol, 2.3 equiv) was added followed by isobutyl chloroformate (110 µL, 0.85 mmol, 2.3 equiv) and solution was stirred at room temperature for 45 minutes. Water (10 mL) and ethyl acetate (10 mL) were added and layers were separated. Solvent was evaporated, then activated ester was dissolved in DMF and hydroxy(acetoxy)cisplatin(IV) acetic acid complex (160 mg, 0.367 mmol, 1.00 equiv) was added and solution was stirred at 50° C. for 18 hours. The solvent was evaporated and crude was purified on silica gel (3-8% MeOH/DCM gradient) to afford the desired product with residual MeOH. The residue was dissolved in MeOH (1 mL) and solution was added to TBME (50 mL) to obtain a white precipitate that was filtered and dried under vacuum. Compound 14 was obtained as an off-white solid (83 mg, 38% yield). HPLC/MS (method B): 3.21 minutes, M+H=600.

Example 16

Synthesis of a Pt(IV)M monomaleimide, Compound 15

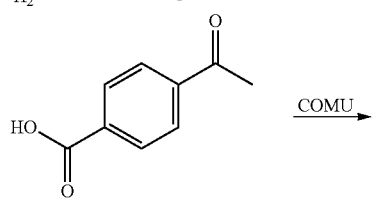

15

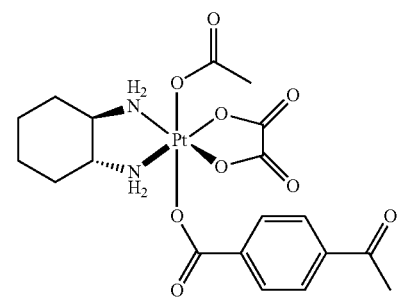

Acetoxyoxaliplatin(4-acetylphenyl)carboxylate: Acetoxy (hydroxyl)oxaliplatin (409 mg, 0.86 mmol, 1.00 equiv), 4-acetylbenzoic acid (170 mg, 1.03 mmol, 1.20 equiv) and COMU (444 mg, 1.03 mmol, 1.20 equiv) were suspended in DMF (0.1 M, 8 mL) and N-methylmorpholine (114 µL, 1.03 mmol, 1.20 equiv) was added at room temperature. The reaction mixture was stirred at room temperature for 16 hours. The reaction mixture was concentrated and the residue was suspended on silica gel and purified by normal phase chromatography using a silica gel column (40 g) eluted with 5-20% MeOH/CH$_2$Cl$_2$ gradient over 15 minutes. Pure fractions were combined and concentrated in vacuum to provide the product as an off-white solid (328 mg, 61%, 94.8% pure). HPLC-MS 94.8%, m/z for C$_{19}$H$_{24}$N$_2$O$_9$Pt [(M+H)+]=620.2.

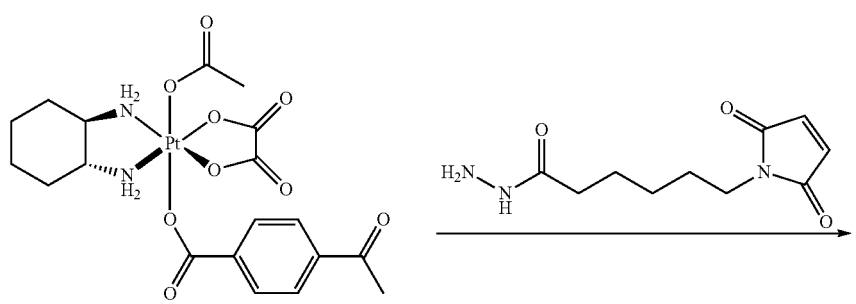

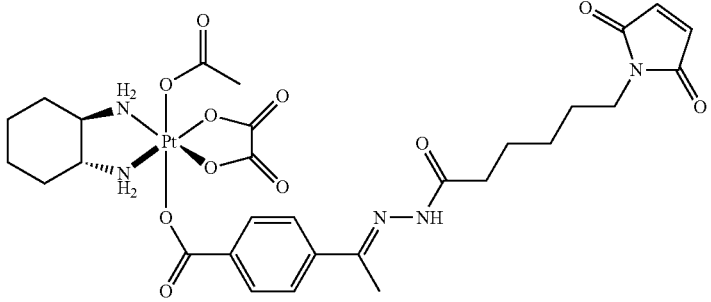

15

Acetate 4-(1-(2-(6-(2,5-dioxo-2H-pyrrol-1(5H)-yl)hex-anoyl)hydrazono)ethyl)benzoate oxaliplatin was synthesized using acetoxyoxalplatin(4-acetylphenyl)carboxylate (328 mg, 0.529 mmol, 1.00 equiv) that was dissolved in DMF (0.05 M, 10 mL) and treated with 6-(2,5-dioxo-2,5-dihydro-1H-pyrrol-1-yl)hexanehydrazide TFA salt (359 mg, 1.05 mmol, 2.00 equiv). The reaction mixture was stirred at room temperature for 16 hours. MTBE was added to the reaction mixture until a gum was formed and the solvent was decanted. To the gummy residue was added more MTBE and the mixture was incubated in an ultrasonic bath until the gum turned into a yellow solid. The solid was filtered and rinsed with MTBE to afford compound 15 (126 mg, 29%, 93.2% pure); 1H NMR (500 MHz, DMF-d7) δ 10.50 (s, 0.4H), 10.42 (s, 0.6H), 8.95-8.44 (m, 4H), 7.92-7.88 (m, 4H), 7.03 (s, 0.8H), 7.02 (s, 1.2H), 3.62-3.35 (m, 6H), 2.46-2.33 (m, 5H), 1.98 (s, 3H), 1.78-1.50 (m, 8H), 1.43-1.22 (m, 4H); HPLC-MS 93.2%, m/z for C29H37N5O11Pt [(M+H)+]=828.3

Example 17

Synthesis of a Pt(IV)M monomaleimide, Compound 16

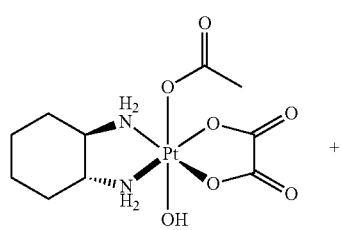

+

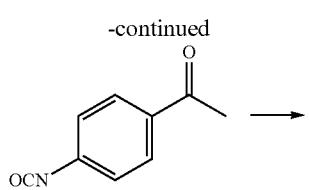

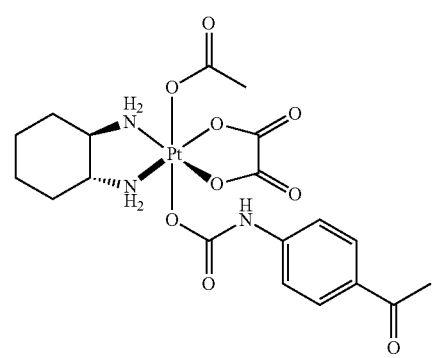

Acetoxyoxaliplatin(4-acetylphenyl)carbamate was first synthesized using acetoxy(hydroxyl)oxaliplatin (243 mg, 0.51 mmol, 1.00 equiv) and 4-acetylphenylisocyanate (124 mg, 0.77 mmol, 1.50 equiv) dissolved in DMF (0.1 M, 5 mL). The reaction mixture was stirred at room temperature overnight. The reaction mixture was concentrated and impregnated on silica gel. The crude product was purified by normal phase chromatography using silica gel column (40 g) eluted with 5-20% MeOH/CH2Cl2 gradient over 15 minutes. Pure fractions were combined and concentrated under vacuum to provide the product as a yellow solid (241 mg, 74%, 83% pure). HPLC-MS 83.1%, m/z for C19H25N3O9Pt [(M+H)+]= 635.2.

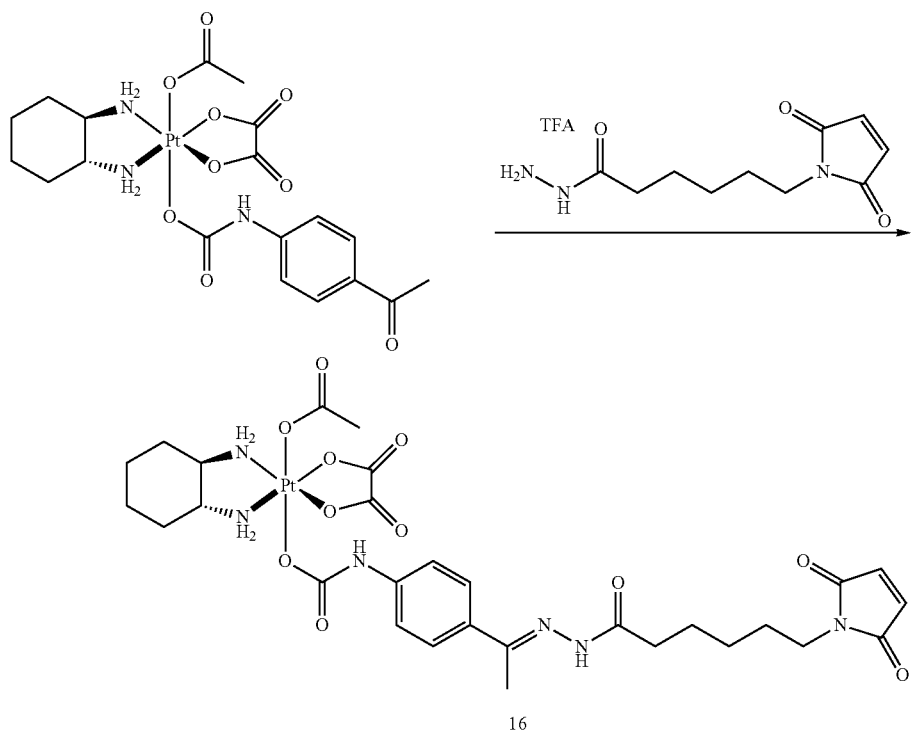

Synthesis of acetate 4-(1-(2-(6-(2,5-dioxo-2H-pyrrol-1(5H)-1)-hexanoyl)hydrazono)ethyl) phenyl carbamate oxaliplatin Acetoxyoxalplatin(4-acetylphenyl)carbamate (228 mg, 0.36 mmol, 1.00 equiv) was dissolved in DMF (0.05 M, 7 mL) and treated with 6-(2,5-dioxo-2,5-dihydro-1H-pyrrol-1-yl) hexanehydrazide TFA salt (158 mg, 0.47 mmol, 1.30 equiv). The reaction mixture was stirred at room temperature for 16 hours. The reaction mixture was concentrated and the residue was triturated with acetonitrile to precipitate the product as a yellow powder. This powder was triturated first with isopropyl alcohol (iPrOH) and then with DCM to afford the desired product (70 mg, 23%, 93.5% pure). HPLC-MS 93.5%, m/z for $C_{29}H_{38}N_6O_{11}Pt$ [(M+H)+]=842.3. $^1$H NMR (500 MHz, DMF-$d_7$) δ 10.34-10.15 (m, 1H), 9.91-9.66 (m, 1H), 9.37-9.24 (m, 1H), 8.88-8.66 (m, 2H), 8.59-8.48 (m, 1H), 7.80-7.73 (m, 2H), 7.61-7.53 (m, 2H), 7.04-6.98 (m, 2H), 3.50-3.43 (m, 2H), 3.14-3.02 (m, 1H), 2.75-2.70 (m, 1H), 2.43-2.25 (m, 6H), 2.01-1.92 (m, 3H), 1.74-1.53 (m, 9H), 1.42-1.24 (m, 4H).

Example 18

Synthesis of a Pt(IV)M monomaleimide, Compound 17

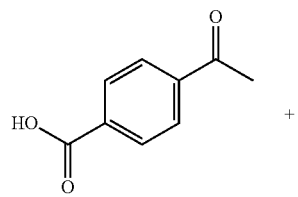

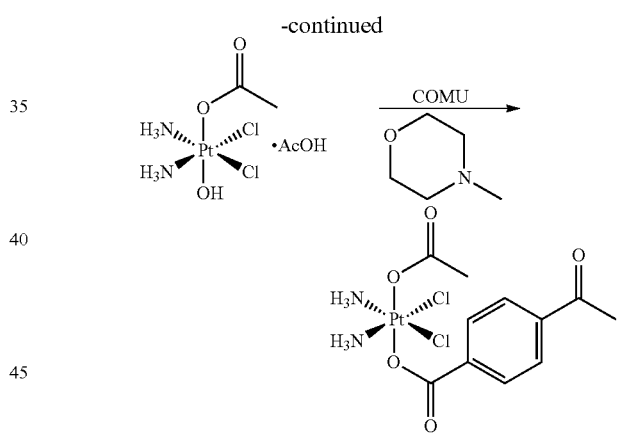

Acetoxycisplatin(4-acetylphenyl)carboxylate: Hydroxy (acetoxy)cisplatin acetic acid complex (500 mg, 1.15 mmol, 1.0 equiv), 4-acetylbenzoic acid (240 mg, 1.46 mmol, 1.27 equiv) and COMU (625 mg, 1.46 mmol, 1.27 equiv) were suspended in DMF (0.05M, 25 mL) followed by N-methylmorpholine (160 μL, 1.46 mmol, 1.27 equiv) at room temperature. The reaction mixture was stirred at room temperature overnight and the suspension slowly became a yellow solution. The HPLC-MS showed incomplete conversions, and more COMU (205 mg, 0.478 mmol, 0.42 equiv) and N-methylmorpholine (160 uL, 1.46 mmol, 1.27 equiv) were added. The reaction mixture was then stirred for an additional 3 hours. The reaction mixture was concentrated and the residue was dissolved in water and purified by reversed phase chromatography using a pre-packed C18 60 g-column, eluted with 0-30% MeCN/H$_2$O gradient over 15 minutes. Pure fractions were combined and lyophilized to provide the product as a yellow solid (236 mg, 34%, 80% pure). The solid was triturated in MTBE to afford acetoxycisplatin(4-acetylphenyl)carboxylate (180 mg, 30% yield). HPLC-MS 100%, m/z for $C_{11}H_{16}Cl_2N_2O_5Pt$ $[(M+H)^+]=523.1$.

Example 19

Synthesis of a Pt(IV)M monomaleimide, Compound 18

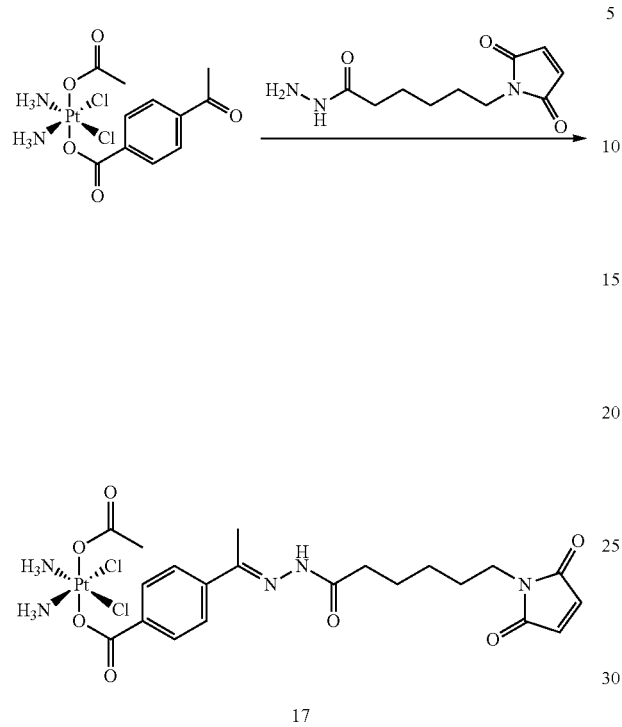

17

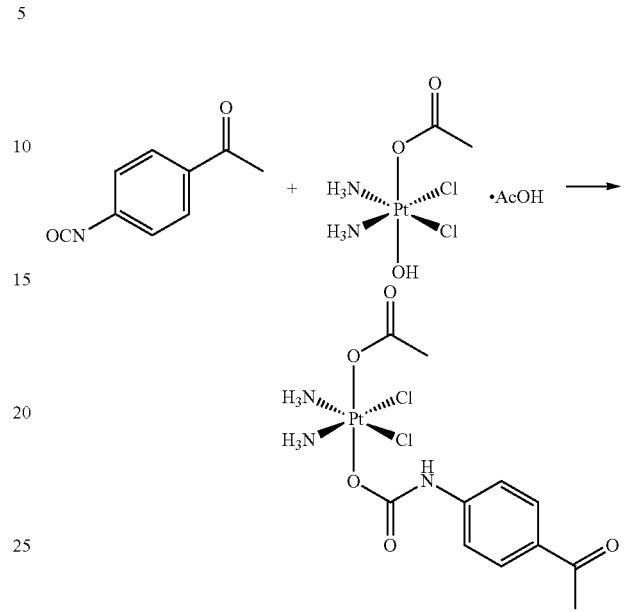

Synthesis of acetoxycisplatin(4-acetylphenyl)carbamate

Acetoxycisplatin(4-acetylphenyl)carboxylate (178 mg, 0.341 mmol, 1 equiv) was dissolved in DMF (0.05 M, 6.8 mL) and treated with 6-(2,5-dioxo-2,5-dihydro-1H-pyrrol-1-yl)hexanehydrazide TFA salt (139 mg, 0.409 mmol, 1.2 equiv). The reaction mixture was stirred at room temperature for 5 hours. MTBE was added to the reaction mixture until a suspension was obtained and a yellow solid was filtered to afford compound 17 (159 mg, 64%, 97% pure). $^1$H NMR (500 MHz, DMF-d7) δ 10.48 (s, 0.3H), 10.40 (s, 0.6H), 7.97-7.92 (m, 2H), 7.91-7.86 (m, 2H), 7.24-6.77 (m, 6H), 7.02 (s, 2H), 3.50-3.44 (m, 2H), 2.77-2.72 (m, 1.4H), 2.44-2.38 (m, 0.6H), 2.40 (s, 2H), 2.37 (s, 1H), 1.94 (s, 3H), 1.73-1.64 (m, 2H), 1.63-1.54 (m, 2H), 1.42-1.29 (m, 2H); HPLC-MS 98%, m/z for $C_{21}H_{29}Cl_2N_5O_7Pt$ $[(M+H)^+]=730.2$.

Hydroxy(acetoxy)cisplatin acetic acid complex (300 mg, 0.688 mmol, 1.00 equiv) was suspended in DMF (0.05 M, 16 mL) and before 4-isocyanatoacetophenone (257 mg, 1.60 mmol, 2.33 equiv) was added at room temperature. The reaction mixture was stirred at room temperature overnight. The next morning the reaction mixture was concentrated to dryness and the residue was triturated in a water and methanol mixture. The suspension was filtered and 340 mg of a yellow solid was obtained containing product and 18% of a 4-acetylphenyl by-product. The solid was dissolved in DMF and purified by reverse phase chromatography using a prepacked C18 60 g column, eluted with 0-30% MeCN/H$_2$O gradient over 15 minutes. Pure fractions were combined and lyophilized to provide the product as a yellow solid (218 mg, 59% yield). HPLC-MS 100%, m/z for $C_{11}H_{17}Cl_2N_3O_5Pt$ $[(M+H)+]=538.1$.

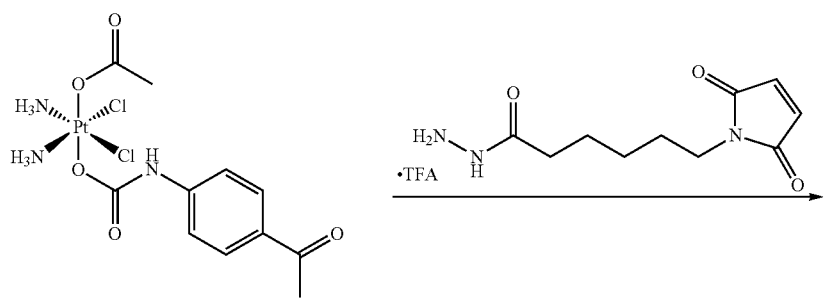

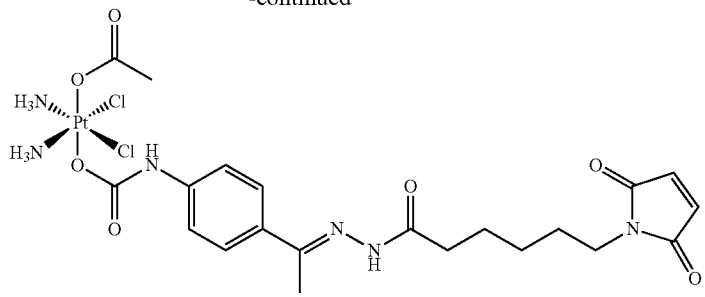

18

Acetoxycisplatin(4-acetylphenyl)carbamate (215 mg, 0.400 mmol, 1.0 equiv) was dissolved in DMF (0.05M, 8 mL) and treated with 6-(2,5-dioxo-2,5-dihydro-1H-pyrrol-1-yl)hexanehydrazide TFA salt (163 mg, 0.480 mmol, 1.2 equiv) at room temperature. The reaction mixture was stirred at room temperature overnight. Dichloromethane was added to the reaction mixture and the suspension was filtered to provide a yellow solid (230 mg, 77% yield, 90.9% pure). The residue obtained was triturated with MeCN to provide compound 18 as a yellow solid (144 mg, 48% yield, 97.3% pure). $^1$H NMR (500 MHz, DMF-d7) δ 10.28 (s, 0.4H), 10.15 (s, 0.6H), 9.74 (brs, 1H), 7.79-7.72 (m, 2H), 7.61-7.54 (m, 2H), 7.22-6.81 (m, 6H), 7.02 (s, 2H), 3.50-3.44 (m, 2H), 2.74-2.70 (m, 1.2H), 2.40-2.35 (m, 0.8H), 2.33 (s, 2H), 2.29 (s, 1H), 1.93 (s, 3H), 1.72-1.63 (m, 2H), 1.62-1.53 (m, 2H), 1.42-1.29 (m, 2H); HPLC-MS 97%, m/z for $C_{21}H_{30}Cl_2N_6O_7Pt$ [(M+H)+]= 745.2.

Example 20

In Vitro Inhibition of Cell Proliferation by Pt(IV)M Monomaleimide Compounds Human cancer cell lines were plated in 96 well plates (Costar) and 24 hours later were treated with a compound for 48-72 hours. Specifically, H460 cells (ATCC) were plated at a concentration of 1,500 cells per well and compound treatment was carried out for 48 hours. Compound starting dose was 20 μM and three-fold serial dilutions were done for a total of ten points. Inhibition of cell proliferation was measured using CellTiter-Glo® reagent using the standard protocol (Promega) and a Glomax® multi+detection system (Promega). Percent proliferation inhibition was calculated using the following formula: % inhibition=(control-treatment)/control*100. Control is defined as vehicle alone. IC50 curves were generated using the nonlinear regression analysis (four parameter) with GraphPad Prism 6.

Selected compounds of the present teachings each has an $IC_{50}$ between 0.0001 μM and 50 μM. For example, as shown in Table 1, some examples of compounds are less active than cisplatin and have $IC_{50}$ value greater than 10 μM.

TABLE 1

| Compound | H460 $IC_{50}$ (μM) |
|---|---|
| Cisplatin | 2.0 |
| 4 | 18.9 |
| 5 | >500 |

TABLE 1-continued

| Compound | H460 $IC_{50}$ (μM) |
|---|---|
| 7 | 40.6 |
| 9 | 14.2 |

These data demonstrate that some Pt(IV)M compounds described herein are weakly efficacious compared to cisplatin for inducing cell death in a cancer cell under the conditions of these experiments.

Example 21

Effect of Pt(IV)M Monomaleimide Compounds on Tumor Growth

Despite the weak efficacy in vitro on cell proliferation compared to cisplatin, applicants assessed the activity of Pt(IV)M monomaleimide compounds in vivo. In these experiments, the ability of compounds to affect the growth of human Calu-6 NSCLC (non-small cell lung cancer) A2780 (ovarian), MIA Paca-2 (pancreatic) and BxPC-3 (pancreatic) xenografts was tested. All mice were treated in accordance with the OLAW Public Health Service Policy on Human Care and Use of Laboratory Animals and the ILAR Guide for the Care and Use of Laboratory Animals, and were conducted at Charles River Laboratories (Morrisville, N.C.). All in vivo studies were conducted following the protocols approved by the Charles River Institutional Animal Care and Use Committee. The MX-1 study was carried out at TD2 (Scottsdale, Ariz.) and all procedures were carried out under institutional guidelines of Translational Drug Development Institutional Animal Care and Use Committee. For the A2780 in vivo studies, 10 week old female NCR nude mice were inoculated subcutaneously into the right flank with 10 million cells in 1:1 RPMI 1640 (Invitrogen, Carlsbad, Calif.)/Matrigel® (BD Biosciences, San Jose, Calif.). For the Calu-6 in vivo studies, 10 week old female NCR nude mice were inoculated subcutaneously into the right flank with 5 million cells in 1:1 RPMI 1640/Matrigel. For the MIA Paca-2, BxPC-3 in vivo studies, the tumor material was maintained by serial engraftment in female nude NCR nude mice. To initiate tumor growth, a 1 mm$^3$ fragment was implanted subcutaneously in the right flank of each test animal. The animals were 9 and 10-11 weeks old at the time the study started for BxPC-3 and MIA Paca-2 models, respectively. For the MX-1 in vivo studies, tumor material was maintained by serial engraftment in athymic nude mice. To initiate tumor growth a 3×3 mm pieces implanted subcutaneously in the right flank of each test animal. The animals were 5 weeks old at the time of implantation.

Tumor measurements were taken twice weekly, using vernier calipers. Tumor volume was calculated using the formula: V=0.5×width×width×length.

When tumors approached a volume of 100 mm³, mice were randomized into three groups of ten animals. Mice were treated with vehicle control (10% Solutol® HS15 in saline), compound 3 or 4 at 10 mg/kg, compounds 2, 7, 8, 11, 14 at 20 mg/kg, or 30 mg/kg compound 13; compound 5 was given at 30 mg/kg by intravenous injection for the A2780 and Calu-6 studies. Compound 5 was dosed at 15 mg/kg for the BxPC-3 and MIA Paca-2 studies. Mice were dosed twice weekly for the duration of the study. Compound 8 was dosed at 10 mg/kg and 15 mg/kg for the MX-1 study, animals were dosed twice weekly for a total of four doses. Twenty-four hours after the final dose tumor volumes were measured again for calculation of tumor growth inhibition. All statistical analyses were performed using GraphPad PRISM® Version 6.00. Final tumor volumes were analyzed using with a one-way analysis of variance and Tukey multiple comparison test.

Figure 2:
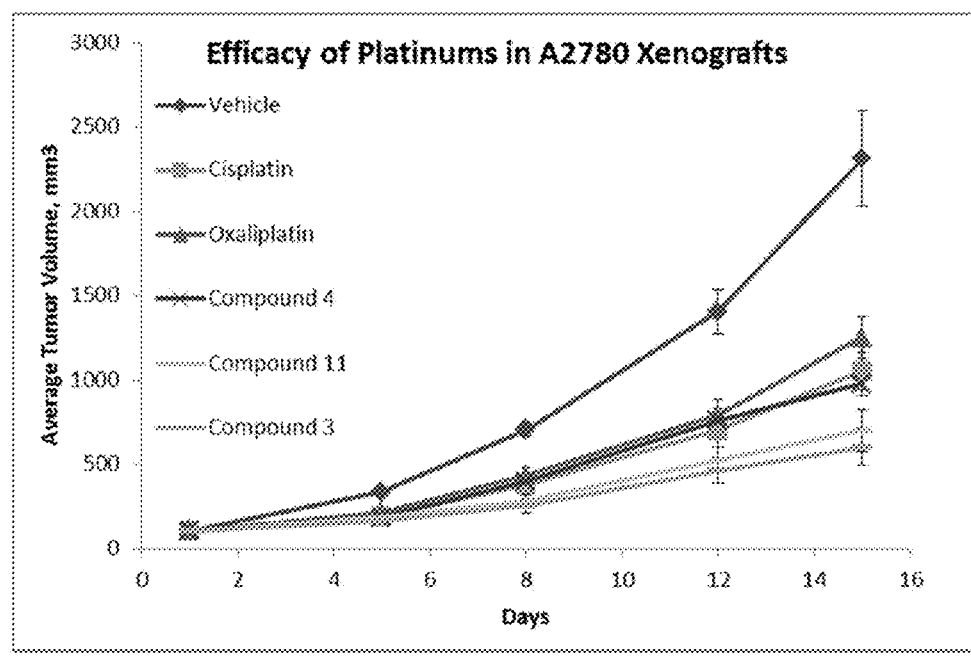
FIG. 2 is a graph illustrating growth curves of A2780 tumors in nude mouse xenografts when the mice were dosed with two control drugs, vehicle or three Pt(IV)M of the present teachings.
Figure 3:
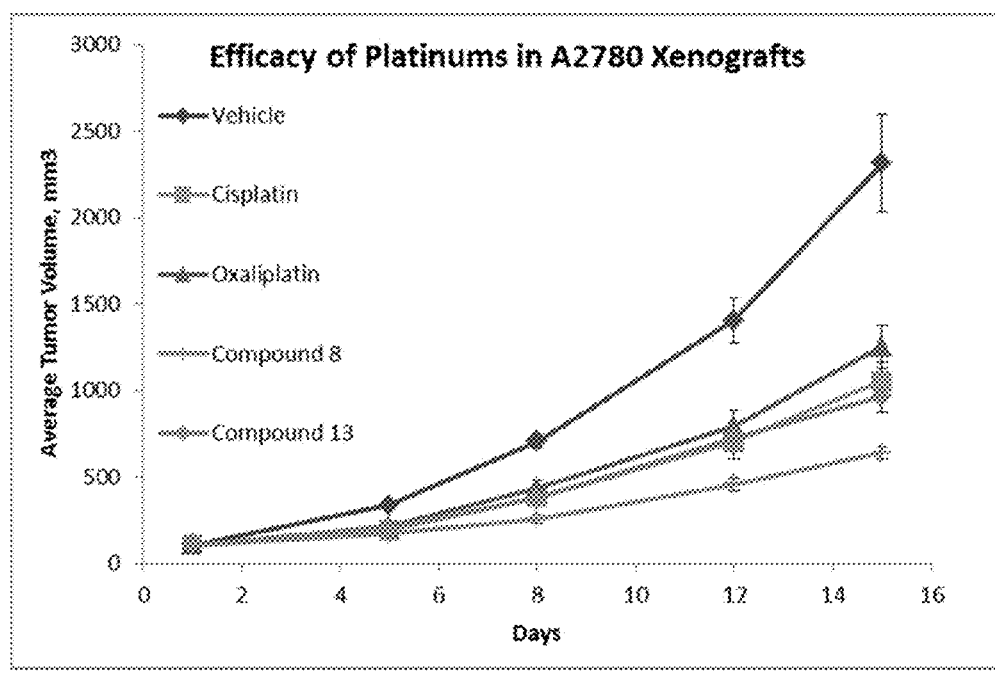
FIG. 3 is a graph illustrating growth curves of A2780 tumors in nude mouse xenografts when the mice were dosed with two control drugs, vehicle or two Pt(IV)M of the present teachings.

Efficacy data for eight compounds in the A2780 model are shown in FIGS. 1-3. Table 2 shows the percent tumor growth inhibition observed in this study for the eight compounds and cisplatin and oxaliplatin as comparators. All of the tested compounds had increased inhibition of tumor growth compared to cisplatin and oxaliplatin in this model.

TABLE 2

| Treatment | TGI % | pValue |
|---|---|---|
| Cisplatin | 54.5 | p < 0.001 |
| Oxaliplatin | 45.9 | p < 0.001 |
| 4 | 57.7 | p < 0.001 |
| 2 | 68.5 | p < 0.001 |
| 7 | 73.3 | p < 0.001 |
| 8 | 72.4 | p < 0.001 |
| 11 | 69.6 | p < 0.001 |
| 3 | 74.0 | p < 0.001 |
| 13 | 58.3 | p < 0.001 |
| 14 | 61.7 | p < 0.001 |

Figure 4:
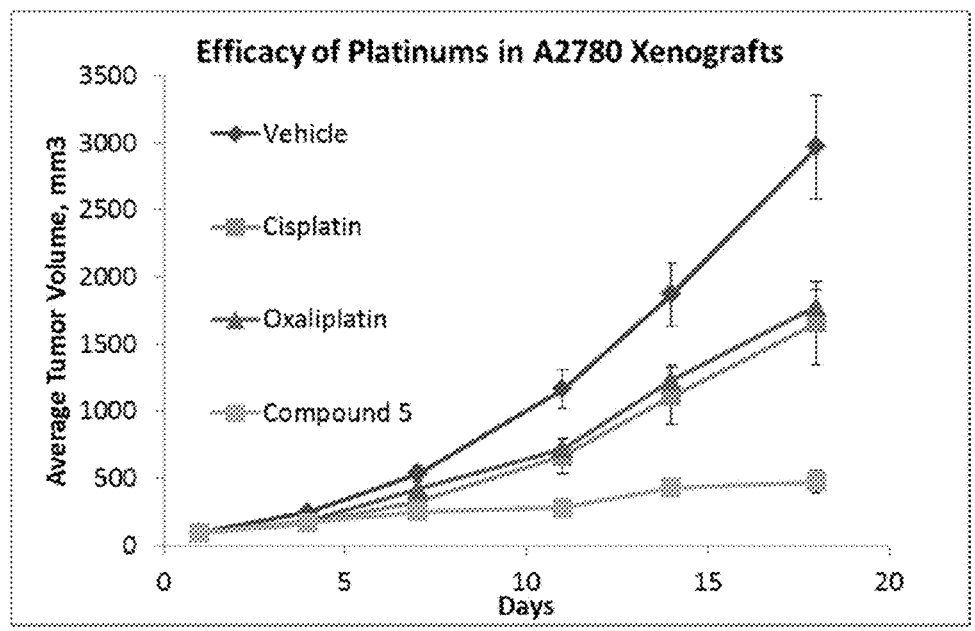
FIG. 4 is a graph illustrating growth curves of A2780 tumors in nude mouse xenografts when the mice were dosed with two control drugs, vehicle or a Pt(IV)M of the present teachings.

Efficacy data for compound 5 in the A2780 model are shown in FIG. 4. Table 3 shows the percent tumor growth inhibition (TGI %) observed in this study for compound 5 and cisplatin and oxaliplatin as comparators.

TABLE 3

| Treatment | TGI % | pValue |
|---|---|---|
| Cisplatin | 44.2 | p < 0.01 |
| Oxaliplatin | 40.1 | p < 0.05 |
| 5 | 84.1 | p < 0.001 |

Figure 5:
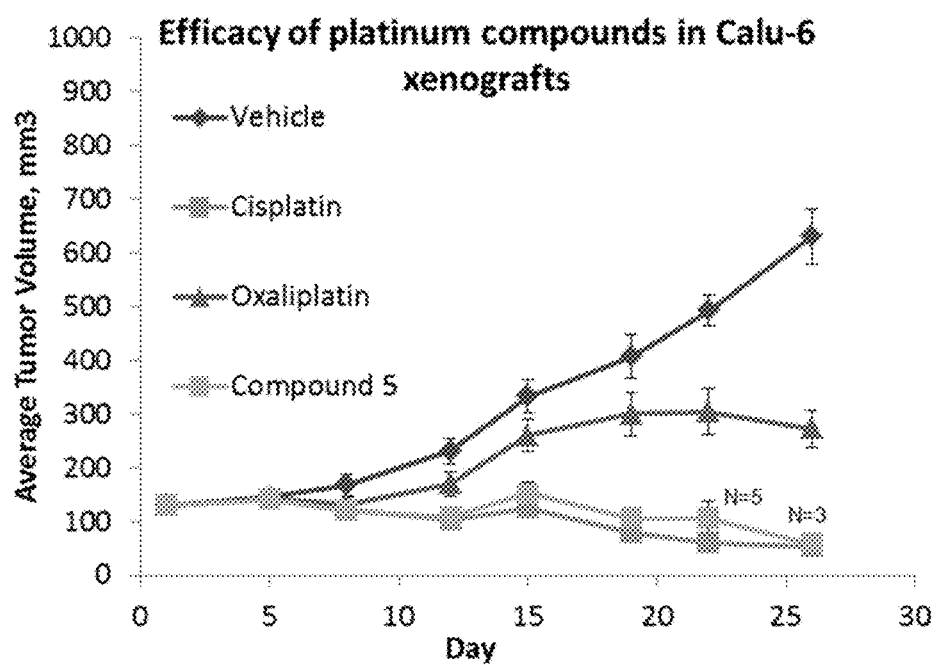
FIG. 5 is a graph illustrating growth curves of Calu-6 tumors in nude mouse xenografts when the mice were dosed with two control drugs, vehicle or a Pt(IV)M of the present teachings.

Efficacy data for compound 5 in the Calu-6 model are shown in FIG. 5. Table 4 shows the percent tumor growth inhibition (TGI %) observed in this study for compound 5 and cisplatin and oxaliplatin as comparators.

TABLE 4-1

| Treatment | TGI % | pValue |
|---|---|---|
| Cisplatin | 91.4 | p < 0.001 |
| Oxaliplatin | 56.7 | p < 0.001 |
| 5 | 90.7 | p < 0.001 |

Figure 15:
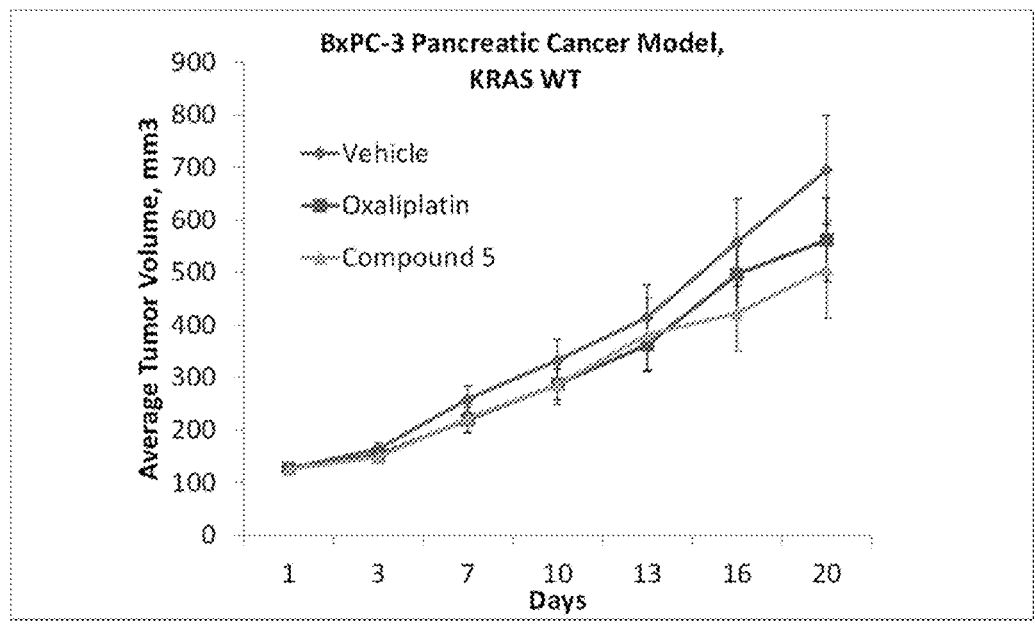
FIG. 15 is a graph illustrating growth curves of KRAS wild type BxPC-3 pancreatic cancer model when the mice were dosed with a control drug, vehicle or a Pt(IV)M of the present teachings.
Figure 16:
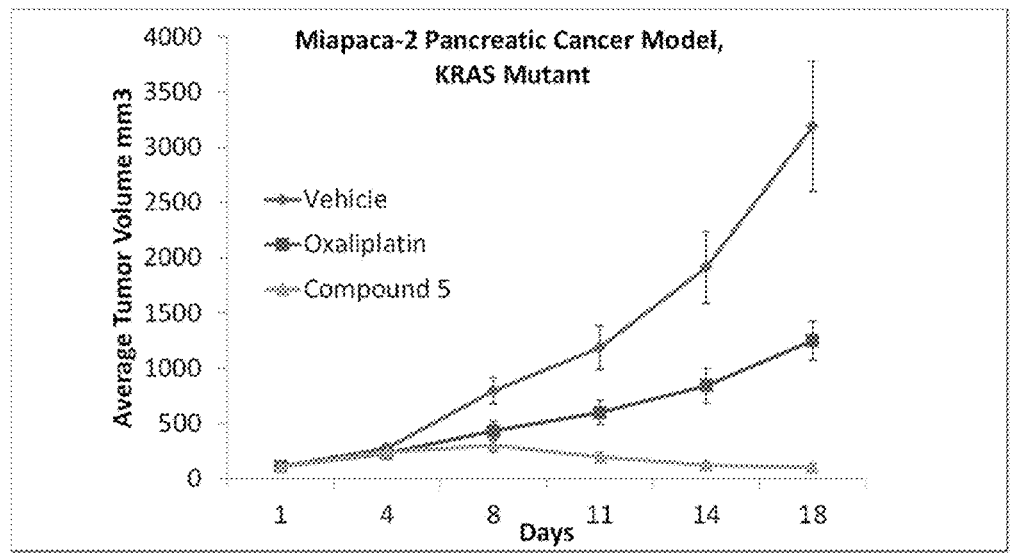
FIG. 16 is a graph illustrating growth curves of KRAS mutant Miapaca-2 pancreatic cancer model when the mice were dosed with a control drug, vehicle or a Pt(IV)M of the present teachings.

Efficacy data for compound 5 in the BxPC-3 model are shown in FIG. 15. Table 4-2 shows the percent tumor growth inhibition (TGI %) observed in this study for compound 5 and oxaliplatin a comparator. This pancreatic model is wild type for KRAS and the results of these data were directly compared to the results seen in Table 4-3, FIG. 16.

TABLE 4-2

| Treatment | TGI % | pValue |
|---|---|---|
| Oxaliplatin | 21.0 | NS |
| 5 | 47.0 | NS |

Efficacy data for compound 5 in the MIA Paca-2 model is shown in FIG. 15. Table 6 shows the percent tumor growth inhibition (TGI %) observed in this study for compound 5 and oxaliplatin as a comparator. These data demonstrate that in the KRAS mutant pancreatic model, MIA Paca-2, compound 5 significnatly inhibits tumor growth. Oxaliplatin also demonstrated tumor growth inhibition in this model, but to a lesser extent. The difference between the activity of Oxaliplatin and compound 5 is statistically significant (P<0.05). The results demonstrate greater efficacy of an albumin binding pro-drug vs. non-albumin binding drug in the presence of a KRAS mutation in the in vivo setting. This data supports the in vitro albumin uptake data, FIG. 13.

TABLE 4-3

| Treatment | TGI % | pValue |
|---|---|---|
| Oxaliplatin | 44.0 | p < 0.01 |
| 5 | 97.0 | p < 0.001 |

These data demonstrate that despite the weak inhibition of cell proliferation shown by compounds in vitro, surprisingly, the compounds demonstrated inhibition of tumor growth in xenografts equal to or greater than that of oxaliplatin and cisplatin. It is also of note that while oxaliplatin exhibited significantly different amounts of inhibition in the two models that were tested, compound 5 was highly effective for inhibiting tumor growth in both models.

Example 22

Tumor Accumulation of Pt(IV)M Monomaleimide Compounds

Figure 6:
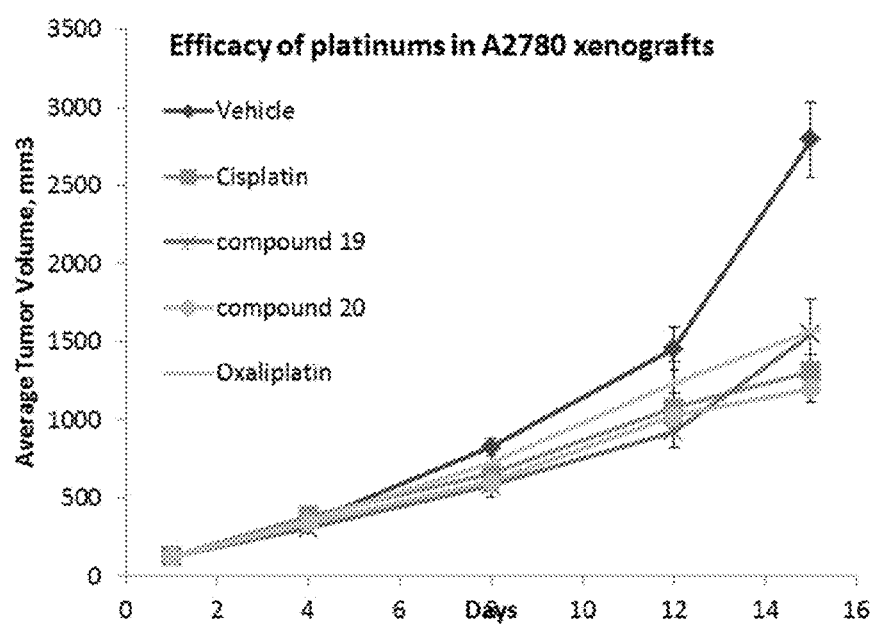
FIG. 6 is a graph illustrating growth curves of A2780 tumors in nude mouse xenografts when the mice were dosed with two control drugs, vehicle or two Pt(IV)M of the present teachings.
Figure 7:
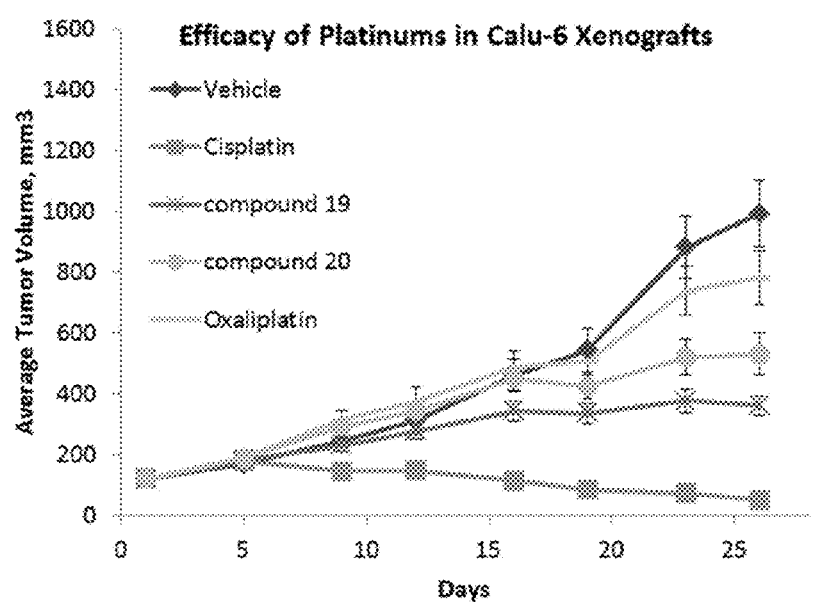
FIG. 7 is a graph illustrating growth curves of Calu-6 tumors in nude mouse xenografts when the mice were dosed with two control drugs, vehicle or two Pt(IV)M of the present teachings.

Applicants previously disclosed two platinum-maleimide compounds (see U.S. Ser. No. 61/922,274). The efficacy data for two maleimide compounds previously disclosed that they are similar to cisplatin and oxaliplatin in the A2780 model and intermediate between oxaliplatin and cisplatin in the Calu-6 model (FIGS. 6 and 7) and are inferior in tumor growth inhibition compared to the molecules disclosed in the present application. The tables below shows the percent tumor growth inhibition (TGI %) observed in these studies for compounds 19 and 20 and cisplatin and oxaliplatin as comparators.

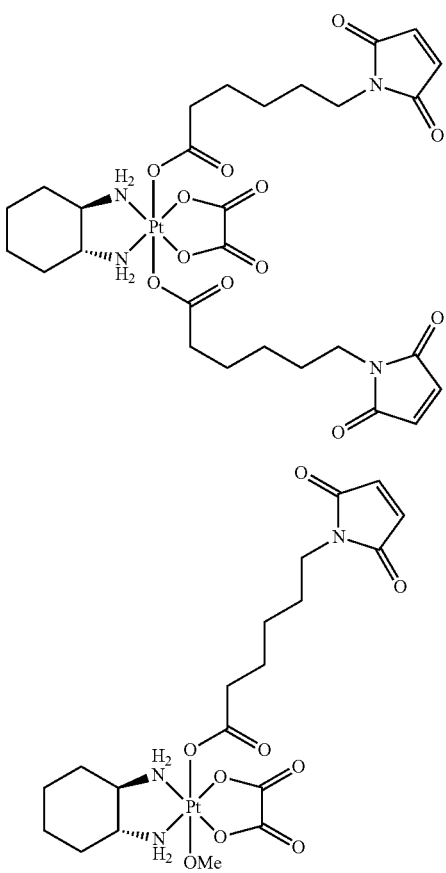

TABLE 5

| A2780 xenografts | | |
|---|---|---|
| Treatment | TGI % | pValue |
| Cisplatin | 53.04 | p < 0.001 |
| 19 | 44.53 | p < 0.001 |
| 20 | 56.98 | p < 0.001 |
| Oxaliplatin | 43.75 | p < 0.001 |

TABLE 6

| Calu-6 xenografts | | |
|---|---|---|
| Treatment | TGI % | pValue |
| Cisplatin | 94.57 | p < 0.001 |
| 19 | 63.57 | p < 0.001 |
| 20 | 46.47 | p < 0.05 |
| Oxaliplatin | 21.19 | p < 0.05 |

Example 23

Tumor Platinum Levels in Tumor-Bearing Nude Mice Dosed with Pt(IV)M Compounds

To examine the ability of compounds disclosed herein to accumulate in tumors, a murine cancer model was used. Animals were inoculated with $5 \times 10^5$ H460 small cell lung cancer cells via subcutaneous injection to the flank. Tumors were allowed to reach an approximate volume of ~500 mm³. Animals were then randomized into treatment groups of 3 animals per time point and were dosed at 4 mg/kg. The 24-hour time point was used as a benchmark across compounds.

Tumor platinum levels were determined by inductively coupled plasma mass spectrometry (ICP-MS). Tumors were excised from animals and dissolved in fuming nitric acid (60% w/w) by adding four parts nitric acid to 1 part tumor w/w and heating overnight at 60° C. The resulting digest was diluted 1:10 in ICP-MS analysis buffer (1% nitric acid, 2% Triton® X-100), and directly introduced into the ICP-MS unit by peristaltic pump. The end dilution factor for the samples as introduced to the ICP-MS was 50×.

Figure 8:
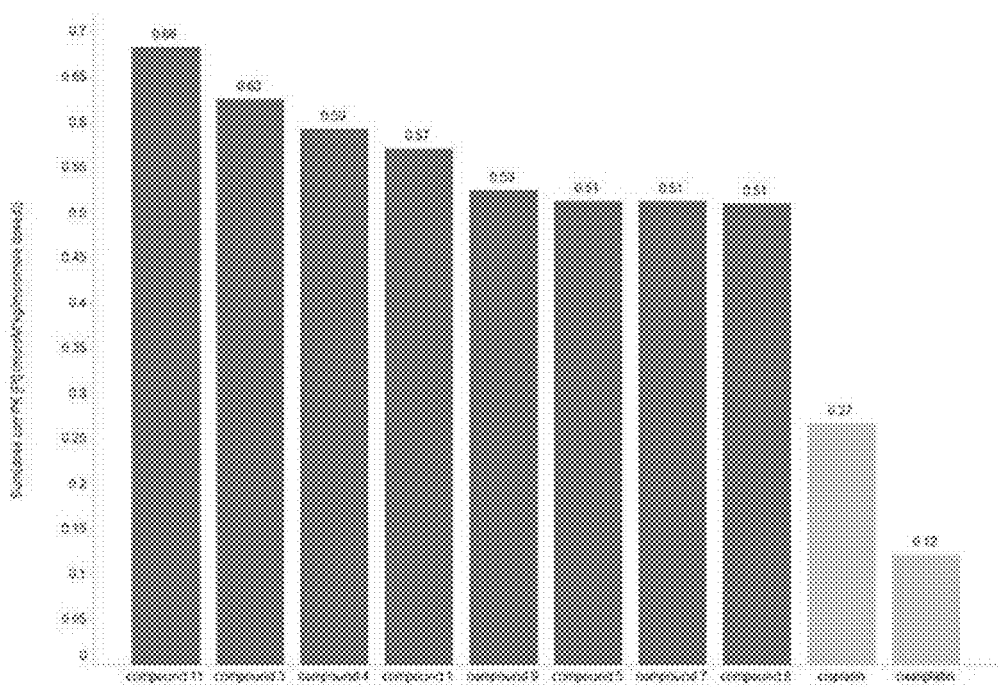
FIG. 8 is a graph depicting platinum levels in tumor when platinum (IV) was dosed in the form of eight exemplary compounds of the present teachings and two comparison compounds to tumor-bearing nude mice via intravenous administration.

FIG. 8 shows the platinum levels in the tumor for 8 exemplary compounds of the present teachings, respectively, plus cisplatin and oxaliplatin for comparison. These data demonstrate that these compounds show higher platinum levels in the tumors than do cisplatin and oxaliplatin. In addition, these data demonstrate a method of determining the ability of a Pt(IV)M compound to deliver platinum to a tumor.

TABLE 7

| Tumor platinum levels in tumor-bearing nude mice dosed with Pt(IV)M compounds | |
|---|---|
| Compound | Platinum in tumor (mM/mmole/kg platinum dosed) |
| Oxaliplatin | 0.12 |
| Cisplatin | 0.27 |
| 1 | 0.57 |
| 3 | 0.63 |
| 4 | 0.59 |
| 5 | 0.51 |
| 7 | 0.51 |
| 8 | 0.51 |
| 9 | 0.53 |
| 11 | 0.68 |

Example 24

Reaction of Compounds 5 and 8 with Albumin or Serum

Without committing to a specific mechanism, it is believed that effective delivery of a Pt(IV)M compound is related to the covalent attachment of the compound to albumin (e.g., human serum albumin; HSA). It is estimated that Pt(IV)M compounds bind to amino acid 34 (cysteine) on an intact alumin. The circulating amount of albumin in blood is high and the covalent bonding to a Pt(IV)M compound is expected to occur in blood. The compound-albumin bond is cleaved at a tumor site, creating an active platinum compound, e.g., a Pt(II) compound.

To confirm the ability of a Pt(IV)M compound to covalently bind to albumin and that the reaction can occur in blood, an assay system was used in which an HPLC system was coupled to an ICP-MS system to measure the platinum-containing trace for albumin reacted platinum compounds. A 300 angstrom pore size C18 column was run with gradient chromatography to effect separation. The weak buffer was 10 mM pH 5 ammonium formate. The strong buffer was 90% acetonitrile and 10 mM ammonium formate. The gradient was from 0% strong buffer to 100% strong buffer over 9 minutes. The injection volume was 5 µL of sample. Albumin containing samples were directly injected onto the LC-ICPMS system with no dilution, extraction, or other pretreatment.

An authentic sample of compound 5 conjugate to albumin was prepared as follows. A 20% HSA solution was used from Lee Solutions (#R8447). The albumin was diluted to a concentration of 5% (50 mg/mL) with PBS. The conjugation of compound 5 was accomplished as follows: 9 mg of 5 was dissolved in methanol and added to 20 mL of albumin solution (concentration=50 mg/mL). The reaction was conducted for 1 hour at 37 degrees C. After 1 hour, the reaction mixture was washed 25 fold with Water for Injection (WFI) by tangential filtration using a 10 KD membrane cutoff filter (Spectrum Labs). After 500 mL of the washed filtrate was collected, the final albumin:compound 5 conjugate solution was concentrated down to 16 mL. To the concentrate, 1.77 mL of 10×PBS was added to yield an albumin conjugate solution in 1×PBS. The mixture was sterile filtered (0.22 micron Millipore Steriflip). The concentration of albumin in the final solution was determined to be 53.17 mg/mL. The solution was stored at 4 degrees C.

Reactions of compound 5 with serum were conducted by spiking 990 µL of murine serum with 10 µL of compound 5 in DMF. The resulting reaction mixture was a 1:100 dilution of drug with only 1% of solvent present in the biological sample. The reaction was conducted at 37° C. for 30 minutes prior to submission of the sample to the LC-ICPMS analysis queue.

Figure 9:
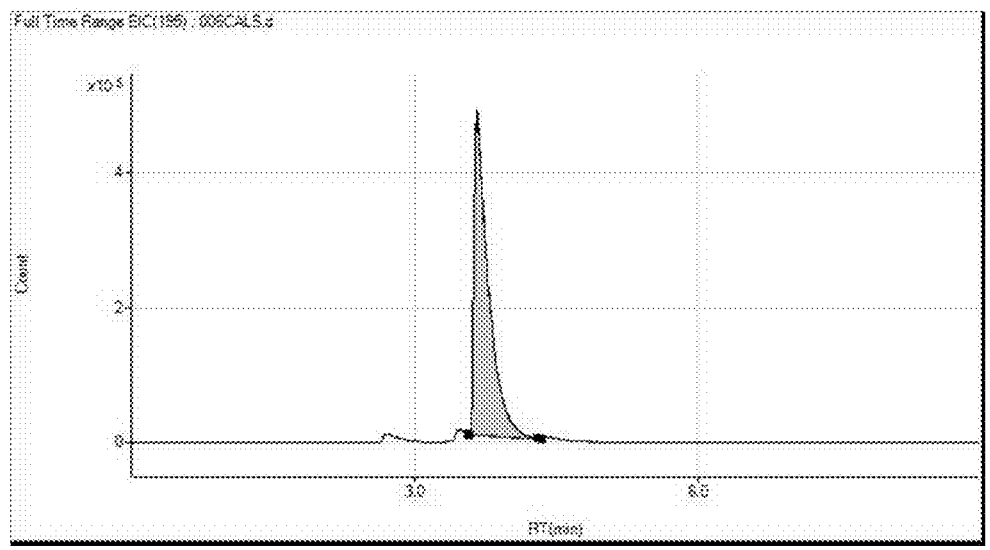
FIG. 9 is an liquid chromatography-inductively coupled plasma mass spectrometry (LC-ICPMS) chromatogram showing the retention time of a Pt(IV)M of the present teachings.
Figure 10:
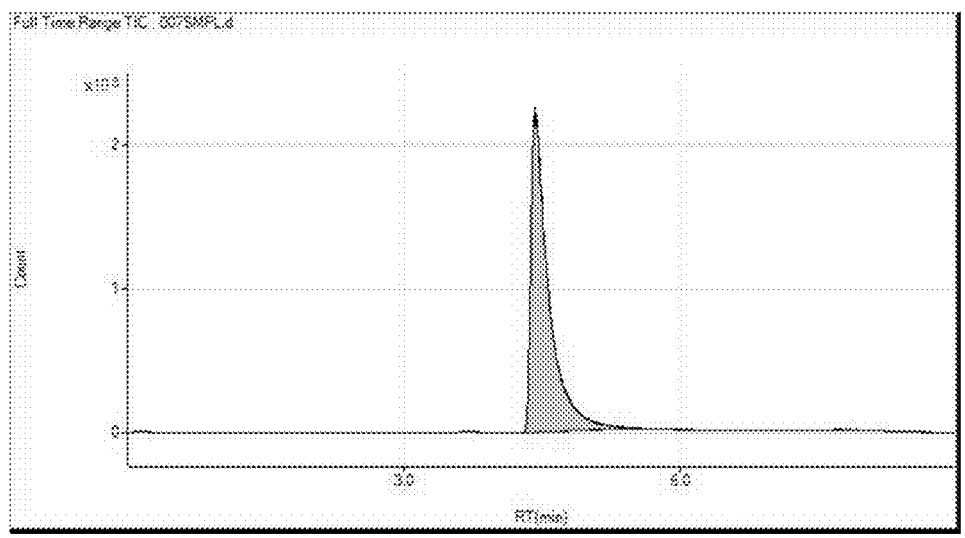
FIG. 10 is an LC-ICPMS chromatogram showing the retention time of a product of the incubation of a Pt(IV)M of the present teachings with commercial albumin.

Control samples were reacted to determine the retention times for various platinum containing species. These included compound 5 and compound 5 reacted with albumin. Following the characterization of the chromatography for retention times, rat serum was reacted with compound 5 to determine the extent of reaction with albumin and the specificity of the albumin reaction. Unreacted compound 5 had a retention time of 3.65 minutes (FIG. 9). Commercial human serum albumin reacted with compound 5 had a retention time of 4.35 minutes (FIG. 10).

Figure 11A:
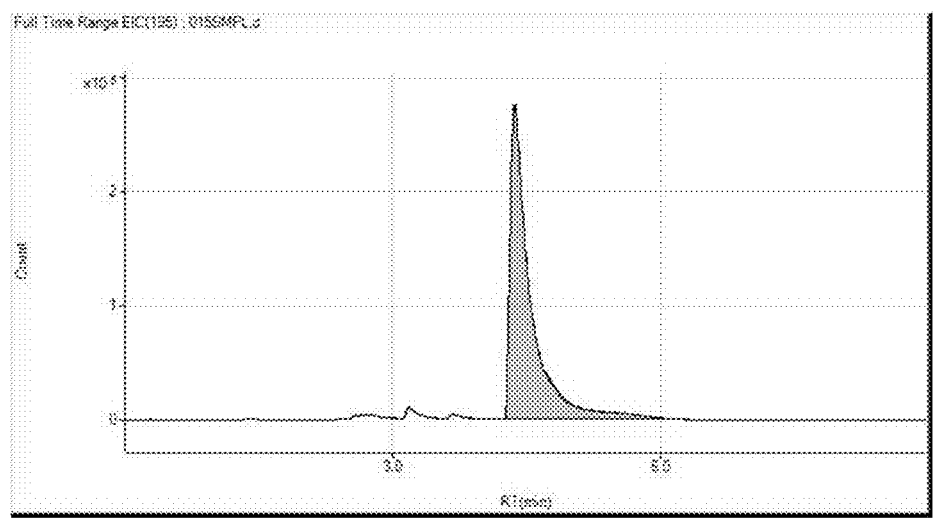
FIG. 11A is an LC-ICPMS chromatogram showing the retention time of a product of the incubation of a Pt(IV)M of the present teachings with rat serum.

When compound 5 at a concentration of 300 µM was incubated in murine serum the resulting LC-ICPMS chromatogram showed 96% of the platinum signal was observed to be albumin-bound (FIG. 11A).

Figure 11B:
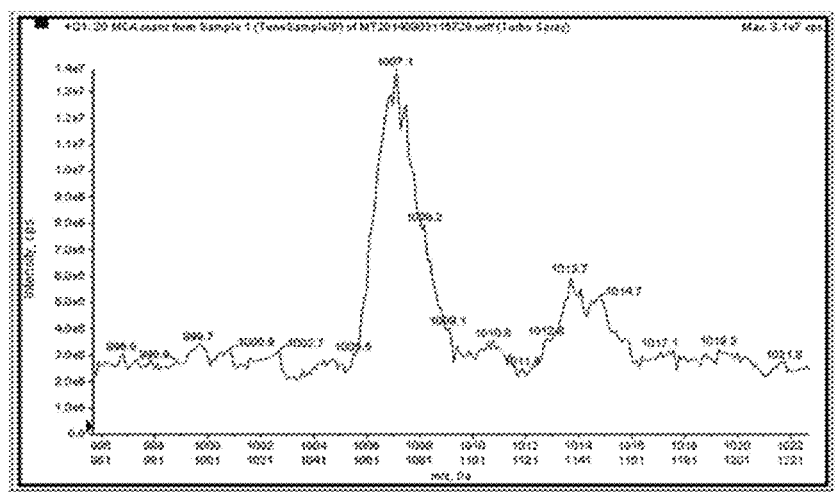
FIG. 11B is LC MS/MS analysis of a Pt(IV)M of the present teachings with albumin tryptic peptide T3.

Compound 8 was mixed with albmin tryptic peptide T3 and LC MS/MS analysis was conducted. The analysis result was shown in FIG. 11B. Signals of T3 endogenous conjugates and T3-Compound 8 conjugates were observed and were evidence that Compound 8 binds to T3.

Example 25

Uptake of Albumin by KRAS Mutant Cells and Treating KRAS Mutant Tumor Cells with Compound 5

Figure 13:
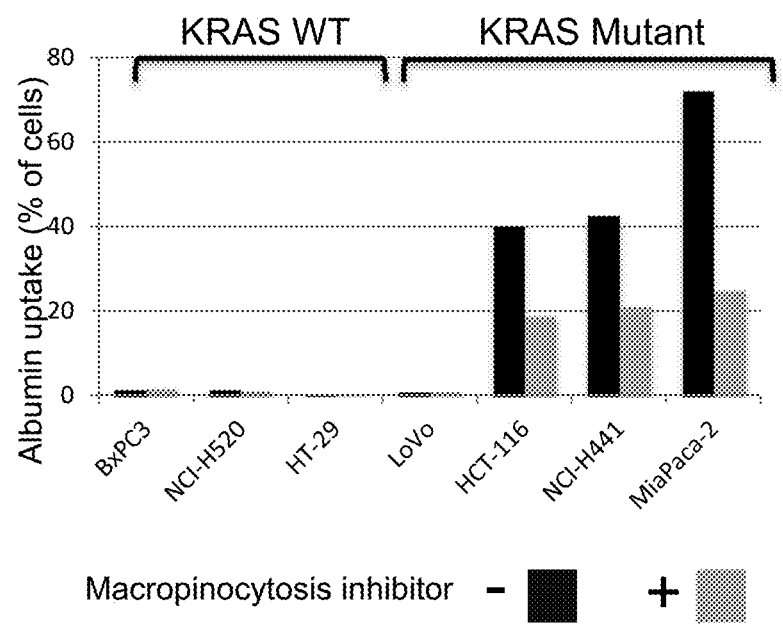
FIG. 13 is a graph illustrating albumin uptake in KRAS mutant cells and KRAS WT cells in vitro.

Albumin uptake was measured in BxPC3, NCI-H520, HT-29 wild type KRAS expressing cell lines and in MiaPaCa-2, NCI-H441, HCT-116 and LoVo KRAS mutation expressing cell lines. As used herein, a "KRAS mutant" is a cell, cell line, or tumor that harbors at least one KRAS mutation. FIG. 13 showed that albumin uptake was much higher in KRAS mutant cells compared to cells that do not harbor a KRAS mutation with the exception of LoVo cells. An inhibitor of macropinocytosis decreased albumin uptake.

Figure 14:
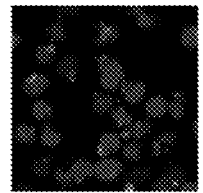
FIG. 14 shows uptake of fluorescently labeled albumin in KRAS mutant cells and KRAS WT cells in vitro.
Figure 14:
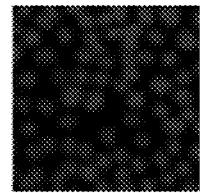

An example of albumin uptake measurements using fluorescently labeled albumin as an imaging agent was shown in FIG. 14. Fluorescently labeled albumin accumulates in KRAS mutant pancreatic Mia PaCa-2 cells more than in KRAS WT pancreatic BxPC3 cells. Radiolabelled albumin may be used as an imaging agent in humans.

Figure 12:
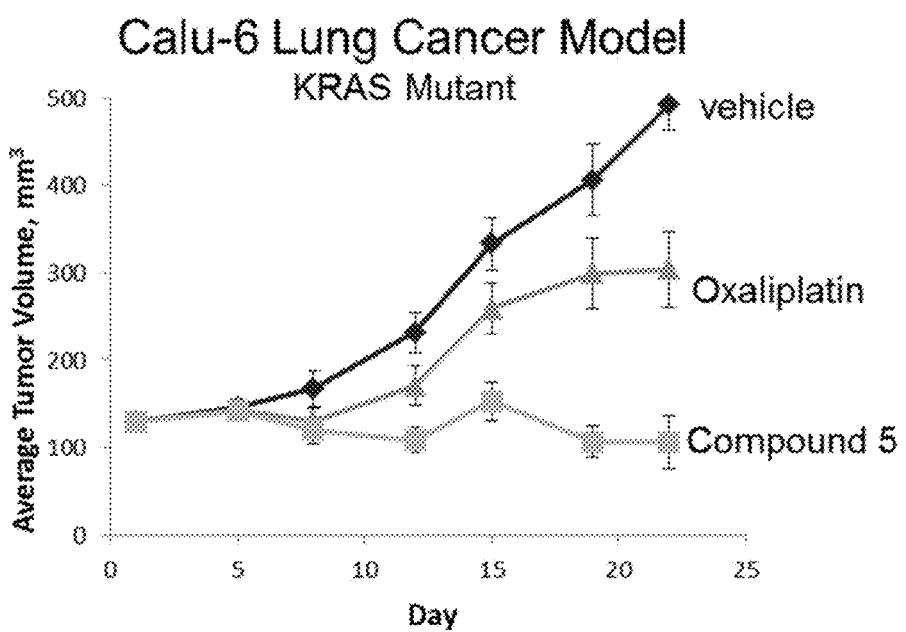
FIG. 12 is a graph illustrating growth curves of KRAS mutant Calu-6 tumors when the mice were dosed with a control drug, vehicle or a Pt(IV)M of the present teachings.

The effect of Pt(IV)M monomaleimide compounds on the growth of KRAS mutant and wild type expressing cells was tested using the same method as described in Examples 21-23. Efficacy data for Compound 5 was shown in FIG. 12, FIG. 15 and FIG. 16. Compound 5 demonstrated inhibition of tumor growth greater than that of oxaliplatin in the KRAS mutant cell lines, Miapaca-2 and Calu-6 as compared to the KRAS wild type line, BxPC-3. Compound 5 was highly effective for inhibiting tumor growth in KRAS mutant models Calu-6 and Miapaca-2.

Example 26

Improved Process for Synthesizing Compound 8

Preparation of compound 8 using improved procedures is presented below.

Improved Process for Synthesizing Compound 8

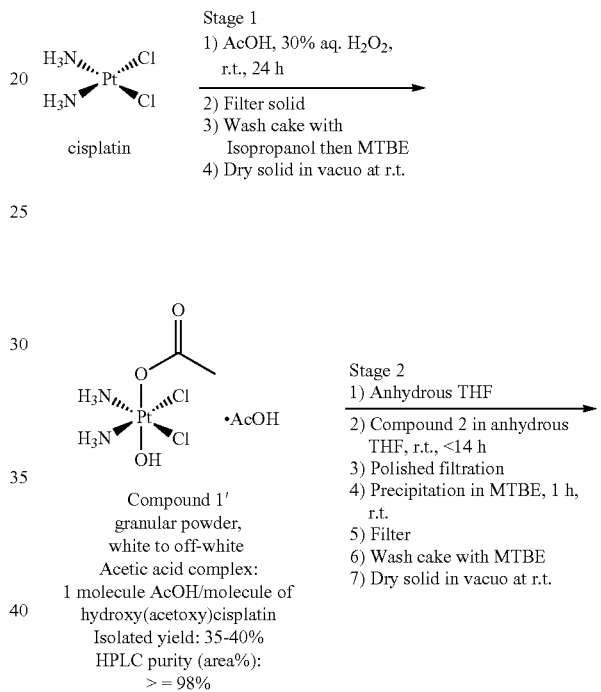

Stage 1
1) AcOH, 30% aq. $H_2O_2$, r.t., 24 h
2) Filter solid
3) Wash cake with Isopropanol then MTBE
4) Dry solid in vacuo at r.t.

cisplatin

Compound 1'
granular powder,
white to off-white
Acetic acid complex:
1 molecule AcOH/molecule of hydroxy(acetoxy)cisplatin
Isolated yield: 35-40%
HPLC purity (area%): >=98%

Stage 2
1) Anhydrous THF
2) Compound 2 in anhydrous THF, r.t., <14 h
3) Polished filtration
4) Precipitation in MTBE, 1 h, r.t.
5) Filter
6) Wash cake with MTBE
7) Dry solid in vacuo at r.t.

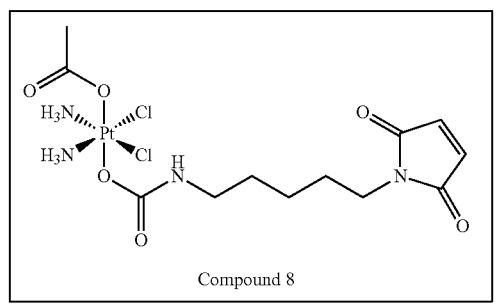

Compound 8

Fine powder, white to off-white
Reaction yield: quantitative
Isolated yield: 96%
HPLC purity (area%): >=95%
Overall yield from cisplatin: ~35%

Isocyanate Synthesis:

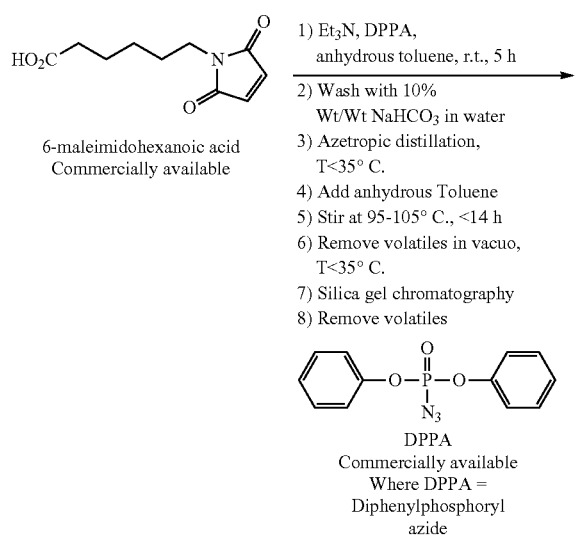

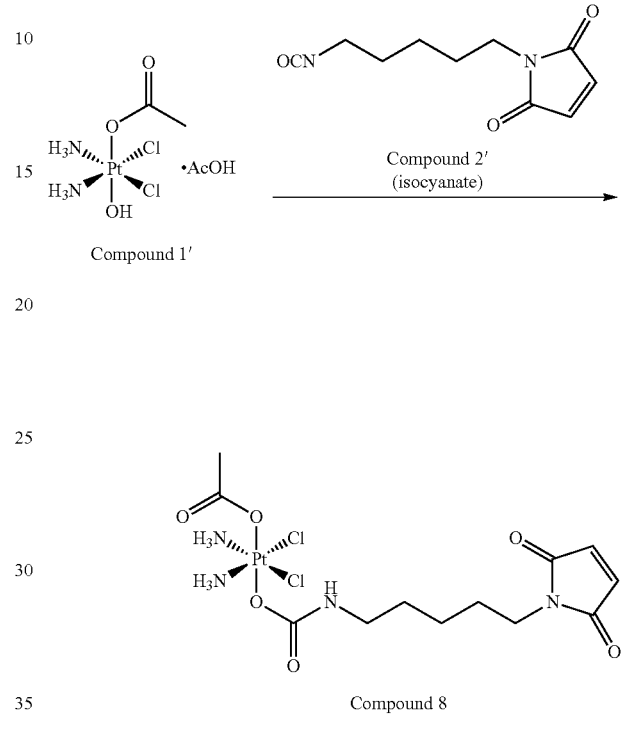

Description of the Improved Procedures for Synthesizing Compound 8

Stage 1

Preparation of Hydroxy(Acetoxy)Cisplatin Acetic Acid Complex (Compound 1')

Cisplatin (4.93 g, 16.4 mmol, 1.00) was charged into a reactor under nitrogen atmosphere. Acetic acid (40.0 mL, 699 mmol, 42.6 eq) was added and the resulting mixture was stirred to produce a suspension. Hydrogen peroxide 30% Wt/Wt in water (7.15 g, 63.1 mmol, 3.85 eq.) was added and stirring continued at temperatures between 23-30° C. for about 4 h (exothermic reaction). The reaction was monitored by reverse phase HPLC and stirring continued at 20-25° C. The suspension was filtered about 24 h after the hydrogen peroxide addition. The cake was washed with isopropanol (3×6 mL) then with MTBE (3×6 mL). The resulting solid was dried, in vacuo, to constant weight at 20-23° C.

Hydroxy(acetoxy)cisplatin acetic acid complex was isolated as a white to off-white powder (2.66 g, 37% yield). Purity based on HPLC>=98%. $^1$H NMR (500 MHz, DMSO) δ 6.57-6.10 (m, 6H), 2.33 (s, 3H), 2.29 (s, 3H); HPLC-MS 98%, m/z for $C_2H_{10}Cl_2N_2O_3Pt$ [(M+H)$^+$]=377.0.

Stage 2

Preparation of Compound 8

Hydroxy(acetoxy)cisplatin acetic acid complex (2.00 g, 4.59 mmol, 1.00 eq) was charged in a reactor under nitrogen atmosphere. Anhydrous THF (20 mL) was added. The resulting mixture was stirred at 20-25° C. to produce a suspension. Compound 2' (Isocyanate, 2.22 g, 10.7 mmol, 2.33 eq) was added as a solution in anhydrous THF (16 mL) and the reaction mixture was stirred at 20-25° C. until complete consumption of starting material (as determined by reverse phase HPLC, reaction completes within 14 h). The crude mixture was used immediately for the next step (precipitation/final isolation).

Compound 8 Precipitation/Final Isolation

MTBE (120 mL) was charged into a reactor under nitrogen atmosphere and stirred at 20-25° C. The crude compound 8 mixture from the previous step was filtered and the filtered solution was added drop-wise to the reactor containing MTBE. A precipitate readily formed when the crude compound 8 mixture became in contact with MTBE. The equipment was rinsed with anhydrous THF (2×2 mL). The suspension was stirred at 20-25° C. for about 1 h. The solid was filtered and the cake washed with MTBE (3×5 mL) under nitrogen atmosphere. The cake was homogenized and the resulting powder was dried in vacuo at 20-25° C. Compound 8 was isolated as a white to off-white fine powder (2.58 g, 96% yield). HPLC purity >=95%. $^1$H NMR (500 MHz, DMF-d7) δ 7.19-6.75 (m, 9H), 3.45 (t, J=7.2 Hz, 2H), 3.04-2.95 (m, 2H), 1.90 (s, 3H), 1.59-1.50 (m, 2H), 1.49-1.37 (m, 2H), 1.34-1.20 (m, 2H); HPLC-MS 96.7%. m/z for $C_{12}H_{22}Cl_2N_4O_6Pt$ [(M+H)$^+$]=585.2.

Preparation of Compound 2' (Isocyanate)

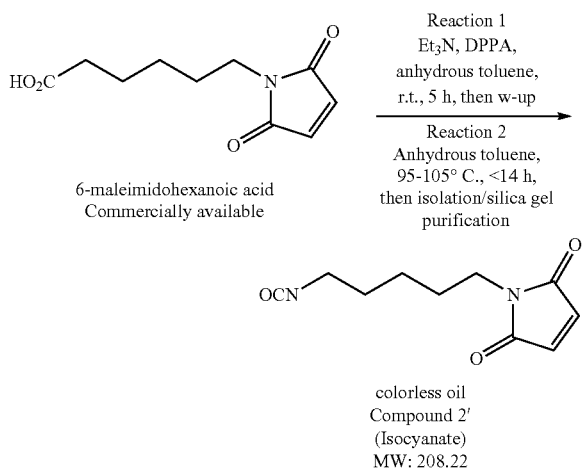

6-maleimidohexanoic acid
Commercially available

Reaction 1
Et₃N, DPPA,
anhydrous toluene,
r.t., 5 h, then w-up

Reaction 2
Anhydrous toluene,
95-105° C., <14 h,
then isolation/silica gel
purification colorless oil
Compound 2'
(Isocyanate)
MW: 208.22

Reaction 1

6-maleimido hexanoic acid (4.22 g, 20.0 mmol, 1.00 eq) was charged into a reactor under nitrogen atmosphere Anhydrous Toluene (200 mL) was added and the resulting mixture was stirred at 20-25° C. to obtain a suspension. Anhydrous triethylamine (3.36 mL, 24.0 mmol, 1.20 eq) was added. The resulting mixture was stirred at 20-25° C. until an homogenous solution was obtained at which point DPPA (4.76 mL, 22.0 mmol, 1.10 eq) was added while keeping the temperature at 20-25° C. Stirring was continued at 20-25° C. for about 5 h. NaHCO₃ 10% Wt/Wt in water (200 mL) was added. The resulting mixture was stirred 5 min then layers were separated within 10 min. The organic layer was concentrated in vacuo, while keeping the temperature <35° C., until toluene (90 mL) had distilled off. Anhydrous toluene (90 mL) was added to the resulting solution.

Reaction 2

The solution obtained from the previous step was heated to 95-105° C. for <14 h under nitrogen atmosphere. Volatiles were removed in vacuo while keeping the temperature <35° C. Crude isocyanate was isolated as a yellow oil (4.83 g, yield=116%). The material can be used as is for preparing compound 8. A small portion (0.4 g) was purified by silica gel chromatography for characterization purposes (purification described in the paragraph below) and to evaluate the performance of purified material in the compound 8 formation reaction (Stage 2, FIG. 1). Based on LC/MS analyses of the crude reaction mixture, purified isocyanate produced cleaner compound 8.

Purification of Compound 2' (Isocyanate)

Silica gel purification: crude oil (0.400 g/4.83 g) was dissolved in ethyl acetate/n-heptane (1:19 V/V, 2 mL) and loaded onto a Redisep column (4 g, 1 CV=4.8 mL). The column was eluted with a gradient of 0-50% (v/v) of ethyl acetate/n-heptane over 12 min. Targeted compound eluted between 4.5-6.5 min. Flow rate: 18 mL/min. Fractions size: 4-6 mL. Fractions were analyzed by LC/MS. Fractions containing compound 2' as a single component were combined and volatiles were removed in vacuo keeping T<30° C. Compound 2' was isolated as a colorless oil (0.180 g). $^1$H NMR (500 MHz, CDCl₃) δ 6.69 (s, 2H), 3.53 (t, J=7.3 Hz, 2H), 3.29 (t, J=6.8 Hz, 2H), 1.67-1.57 (m, 4H), 1.40-1.32 (m, 2H); MS: M+1=209. The NMR spectrum and MS data were consistent with the structure of compound 2'.

Discussion

The procedures disclosed in Example 26 had two stages to transform cisplatin into compound 8. It did not involve any chromatography or lyophilization steps. Compound 8 was purified by precipitation with a purity of >95%. Precipitation provides superior purity (>=95% vs<95% with chromatography and/or lyophilization) and yield (85% vs 51-75% with chromatography and/or lyophilization). Purification of compound 8 by precipitation is straightforward and conducted under conditions that: purge out impurities; provide targeted purity >=95%; prevent degradation of compound 8; provide high yields (85%). As far as cycle time is concerned, purification of compound 8 by precipitation translates into huge time savings: <1 day to precipitate compound 8 as a single batch and compound 8 is stable under these conditions; drastically cuts down the number of the samples to analyze for purity. Raw material costs are minimized by a straightforward purification via precipitation because of higher yields. Chromatography costs are also eliminated. Furthermore, synthesis safety and safety of patients are improved. At stage 1, diethyl ether was replaced by IPA and MTBE washes. These solvents are safe to use on large-scale. Compound 1' was isolated with consistently high-purity >=98% with no negative impact on yield. Diethyl ether is not suitable for scale-up due to its high-volatility, high-flammability, its tendency to form peroxides and sedative properties. Replacing diethyl ether by IPA and MTBE washes was found beneficial for purity and yield of compound 1'. Isocyanate compound 2' was purified to remove DPPA and DPPA by-products. Removal of toxic impurities such as DPPA and DPPA by-products gives higher purity isocyanate compound 2', improves quality of compound 8 and reduces risks for patients.

Conclusion

The method of Example 26 represents a novel path for synthesizing and/or purifying compound 8 (targeted scale of about 0.1-about 1 Kg) because it provides: 1) superior overall purity and yield of compound 8, 2) lesser risk for scalability (compound 8 is more stable under purification conditions), 3) shorter cycle-time (compound 8 is not purified by column chromatography nor lyophilization, 4) lower raw materials costs due to improved overall yield/removal of chromatography purification, 5) made safer by replacing diethyl ether washes by IPA and MTBE washes, 6) rendered safer for patients by preventing impurities such as DPPA and DPPA by-products from entering in the reaction/process to generate compound 8.

Example 27

Figure 17:
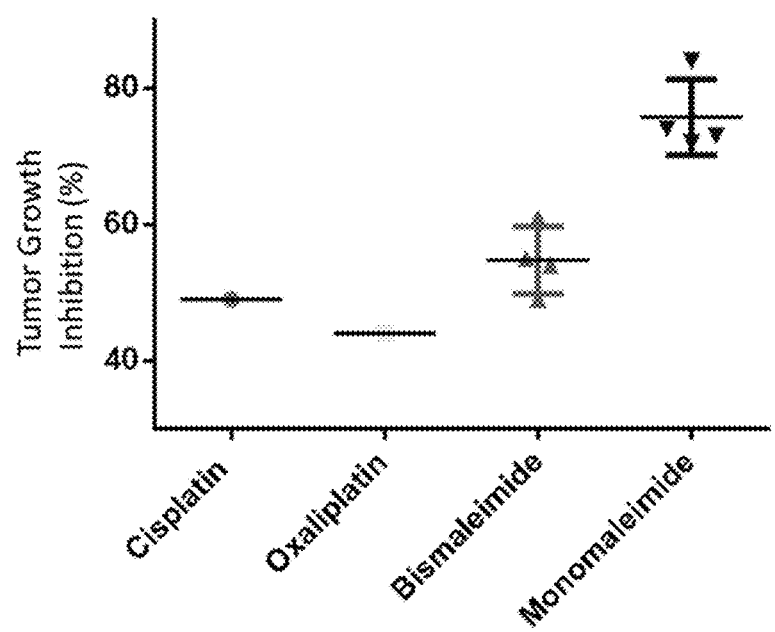
FIG. 17 shows TGI % of cisplatin, oxliplatin, bismaleimide compounds and Pt(IV)M monomaleimide compunds.

Pt(IV)M Monomaleimide Compounds Show Increased Tumor Growth Inhibition than Cisplatin and Oxaliplatin Pt(IV)M monomaleimide compounds (compounds 1, 3, 8 and 11) and compounds comprising two maleimide groups (bismaleimide compounds 19, 28, 29 and 30) were screened in vivo for tumor growth inhibition (TGI %) in A2780 model (ovarian cancer). Cisplatin and oxaliplatin were also tested. Results in FIG. 17 showed that Pt(IV)M monomaleimide have superior TGI % to cisplatin and oxaliplatin.

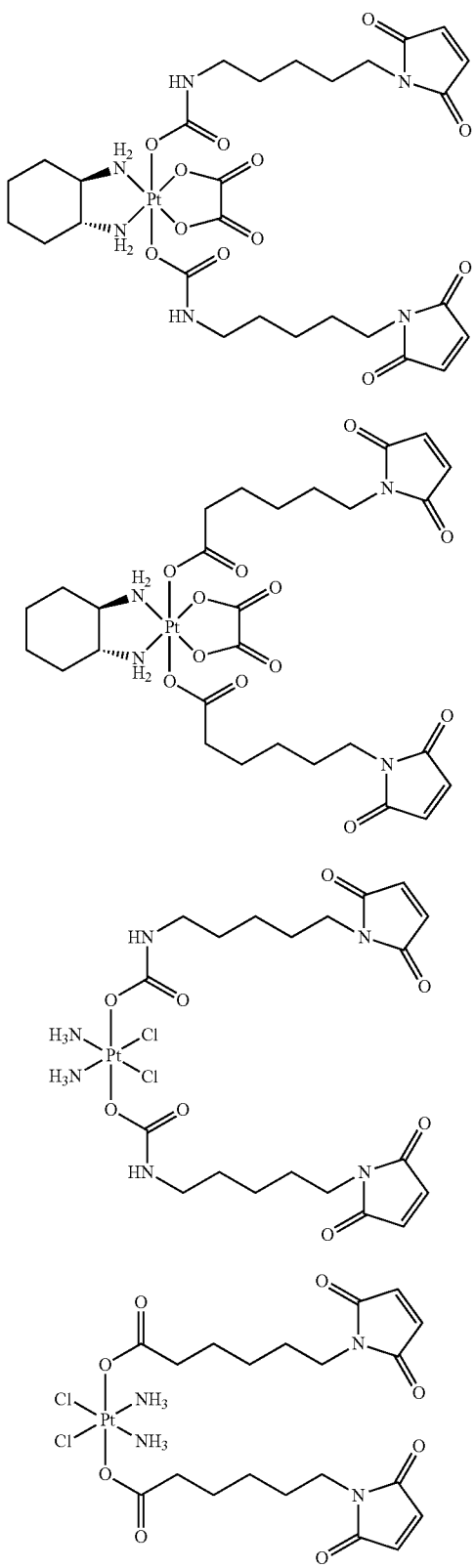

Not willing to be bound to any theory, the second maleimide in bismaleimide compounds has potential to covalently link to other cysteins and lead to cross-linking or toxicity.

Example 28

Figure 18:
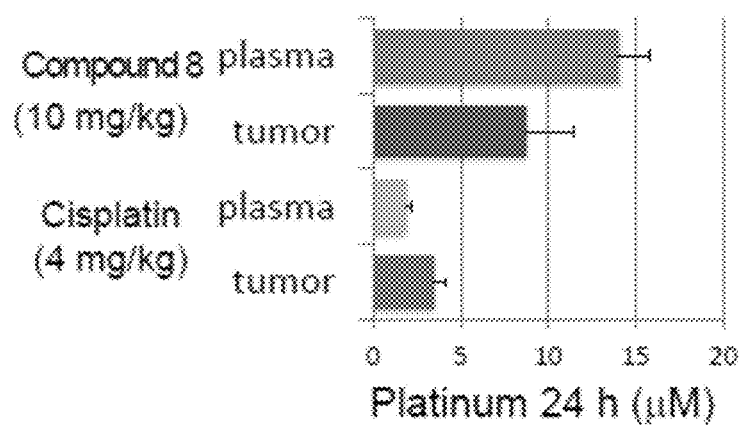
FIG. 18 shows platinum accumulation in plasma and tumor with a single dose of a Pt(IV)M monomaleimide compound and cisplatin in lung cancer model NCI-H460.
Figure 19:
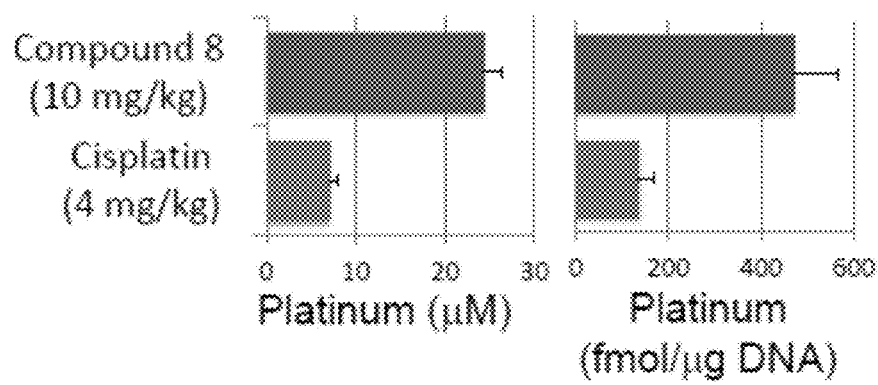
FIG. 19 shows platinum accumulation and DNA platination in plasma and tumor with two doses of a Pt(IV)M monomaleimide compound and cisplatin in lung cancer model NCI-H520.

Increased Platinum Accumulation and DNA Platination Resulting in Increased Tumor Growth Inhibition than Cisplatin Platinum levels in plasma and tumor 24 hr after a single dose of compound 8 at 10 mg/kg were measured in lung cancer model NCI-H460. Platinum levels in plasma and tumor at day 5 after two doses of compound 8 (dosed at days 1 and 4) at 10 mg/kg were measured in lung cancer model NCI-H520. Cisplatin was also tested. Results in FIG. 18 and FIG. 19 showed that compound 8 yielded a higher platinum accumulation in both plasma and tumor than cisplatin in both single does and two-dose studies. Increased tumor platinum results in higher levels of DNA platinum adducts.

Figure 20:
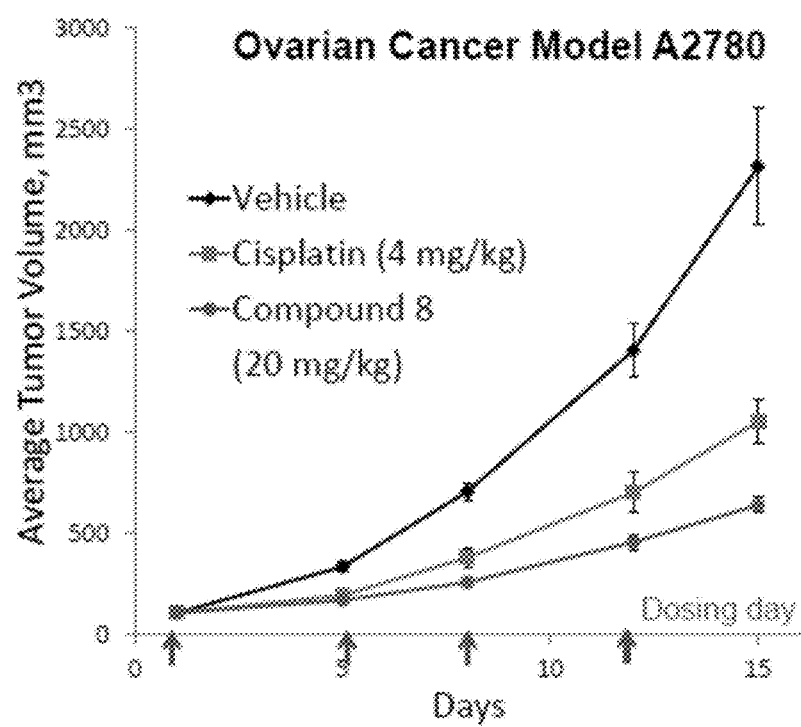
FIG. 20 compares tumor volume in ovarian cancer model A2780 with treatment with cisplatin and a Pt(IV)M monomaleimide compound.
Figure 21:
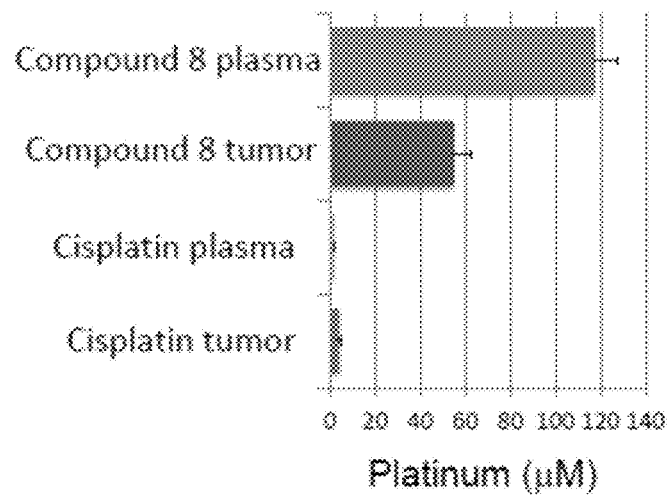
FIG. 21 shows post-study platinum levels in ovarian cancer model A2780 with treatment with cisplatin and a Pt(IV)M monomaleimide compound.

Tumor growth inhibition was measured in ovarian cancer model A2780 for treatment with compound 8 at 20 mg/kg and cisplatin. Results were shown in FIG. 20. Post-study platinum levels were also track and shown in FIG. 21. The concentration of platinum in A2780 xenograph tumor tissue treated with compound 8 was 14 fold higher than cisplatin.

Therefore, Pt(IV)M monomaleimide compound 8 provides higher platinum concentration in tumor tissues than cisplatin and has superior efficacy in tumor inhibition compared to cisplatin.

Example 29

Figure 22:
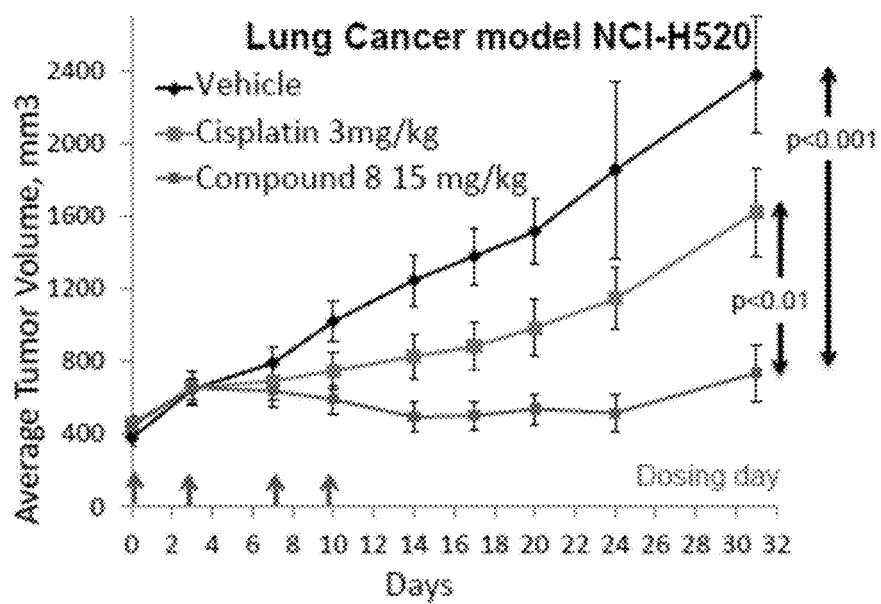
FIG. 22 compares tumor volume after multiple doses of cisplatin and a Pt(IV)M monomaleimide compound in lung cancer model NCI-H520 for 32 days.
Figure 23:
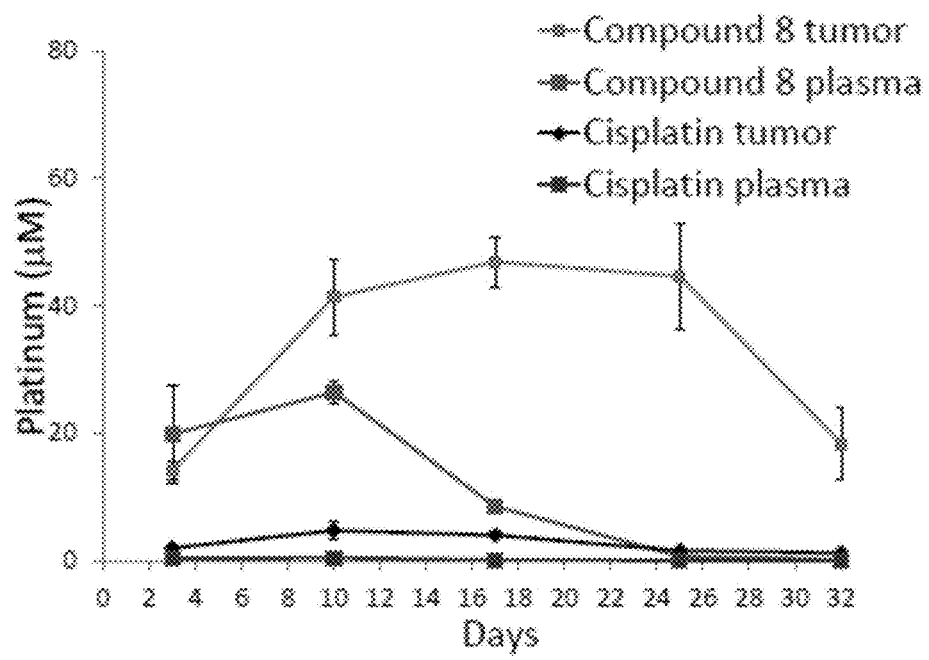
FIG. 23 shows platinum levels after multiple doses of cisplatin and a Pt(IV)M monomaleimide compound in lung cancer model NCI-H520 for 32 days.

Pt(IV)M Monomaleimide Compounds Delivers a Sustained Amount of Platinum to Tumors Tumor volumes and platinum levels were tracked over a course of 32 days after treatment of multiple doses of compound 8 (dosed at days 0, 3, 7 and 10) in lung cancer (NSCLC) model NCI-H520. Compound 8 was dosed at 15 mg/kg. Cisplatin was used as a compare and was dosed at 3 mg/kg. The results were shown in FIG. 22 and FIG. 23. Similarly high platinum levels were observed in tumor 16 days after the last dose at day 10. Sustained release of platinum results in superior tumor growth inhibition than cisplatin.

Figure 24:
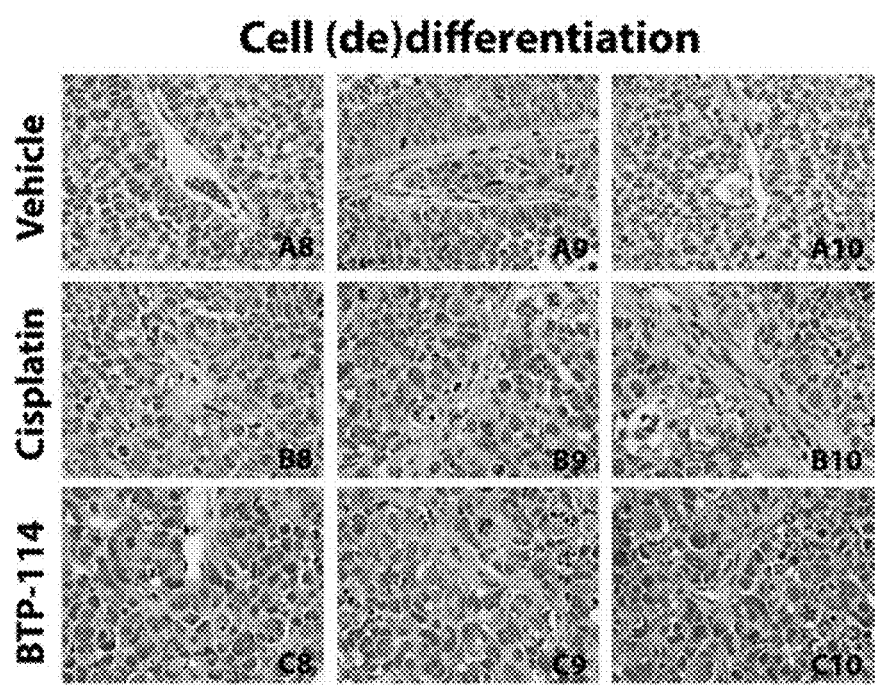
FIG. 24 shows cell dedifferentiation images from day 10 of NCI-H520 study.
Figure 25:
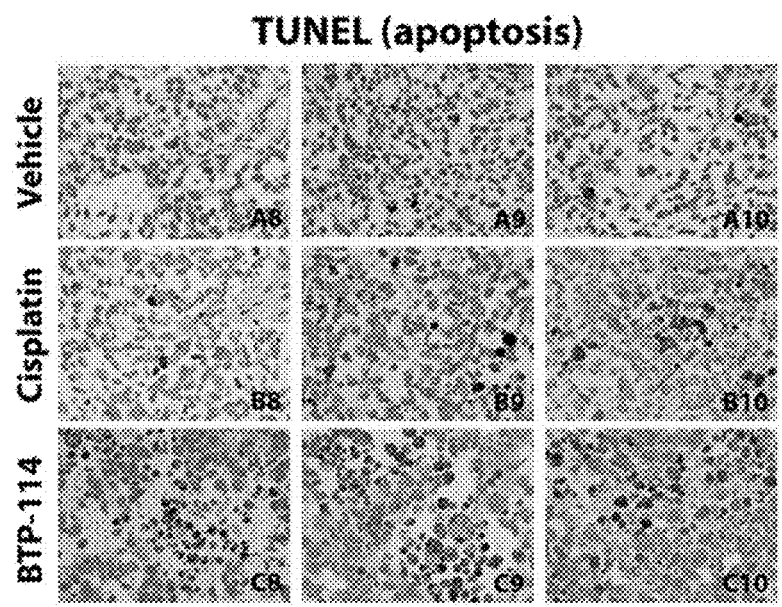
FIG. 25 shows TUNEL apoptosis images from day 10 of NCI-H520 study.

Cell dedifferentiation and apoptosis were studied with immunohistochemical (IHC) and TUNEL stainings Representative images from day 10 of NCI-H520 model were shown in FIG. 24 and FIG. 25. Tumors treated with compound 8 showed significant and sustained increase in apoptosis and dedifferentiation. These results are consistant with superior efficacy and platinum concentrations of compound 8 compared to cisplatin.

Example 30

Pharmacokinetics and Distribution of Pt(IV)M Monomaleimide Compounds

Figure 26:
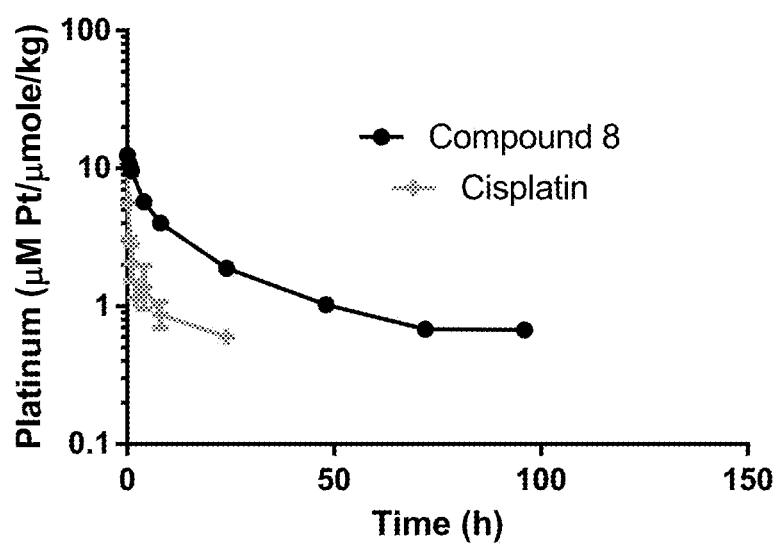
FIG. 26 shows platinum concentrations in rats over a period of up to 100 hours after treatment with cisplatin and a Pt(IV)M monomaleimide compound.
Figure 27:
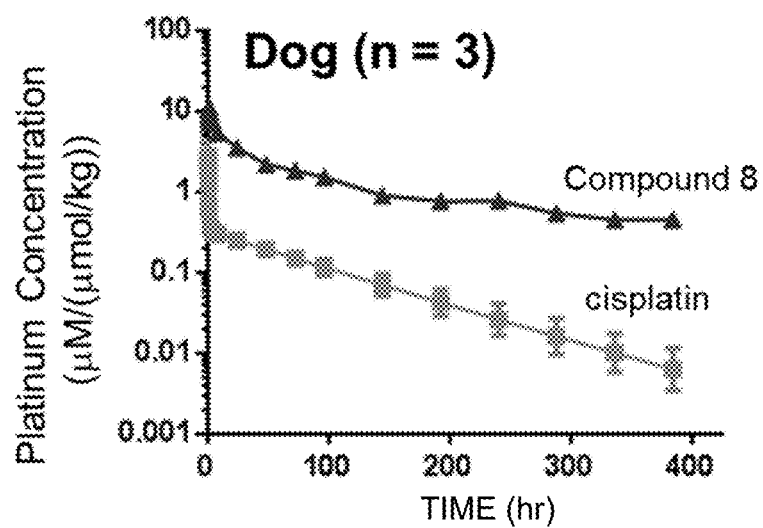
FIG. 27 shows platinum concentrations in dogs over a period of up to 400 hours after treatment with cisplatin and a Pt(IV)M monomaleimide compound.

Platinum concentrations in rat (n=3) and dog (n=3) were both measured in a course of 100 hours and 400 hours, respectively. Cisplatin was also tested as a compare. Results were shown in FIGS. 26 and 27. Half life of compound 8 in rat and dog was calculated and shown in Table 8 below. Albumin was used as a control.

Platinum exposure of compound 8 is 15-18 fold higher than cisplatin. Half-life of compound 8 parallels albumin. Therefore, Pt(IV)M monomaleimide compounds provide a sustained release of platinum and overcomes the rapid clearance of currently available platinum drug.

TABLE 8-1

Half-life of compound 8 and albumin in rat and dog

| Half-life | Rat (h) | Dog (h) |
|---|---|---|
| Compound 8 | 44 | 174 |
| Albumin | 55 | 211 |

Figure 28:
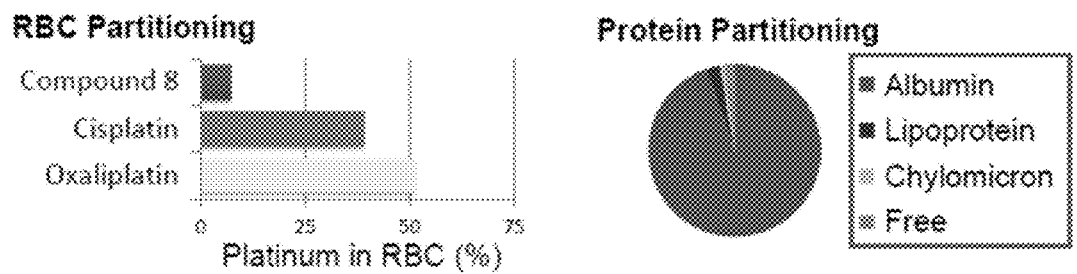
FIG. 28 shows RBC partitioning and protein partitioning after treatment with a Pt(IV)M monomaleimide compound.

RBC partitioning and protein partitioning were studied. Platinum in RBC and in proteins were measured after treatment with compound 8. Results in FIG. 28 showed that compound 8 is not sequestered in red blood cells and 98% of compound 8 is bound to protein in plasma.

Figure 29:
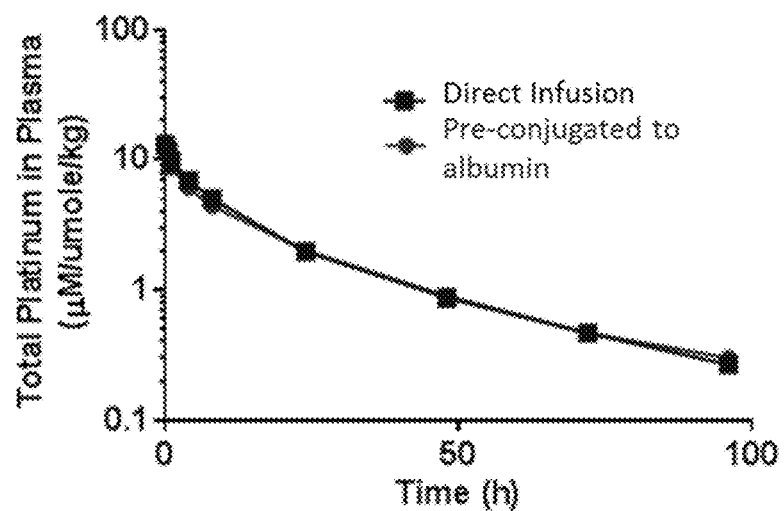
FIG. 29 shows platinum concentrations in plasma in rats treated with a Pt(IV)M compound in direct infusion or pre-conjugated to albumin.

Rat PK study (N=3 rats) was carried out using compound 19 direct infusion and compound 19 pre-conjugated to albumin. Dose normalized data in FIG. 29 show there was a minimal effect on pharmacokinetics of pre-conjugating compound 19 to albumin.

TABLE 8-2

Rat PK parameters of compound 19 direct infusion and compound 19 pre-conjugated to rat albumin

| Parameter | Unit | Direct Infusion | Pre-conjugated to rat albumin |
|---|---|---|---|
| Dose | mg/kg | 2.00 | 2.00 |
| Half life | hr | 26.8 | 27.3 |
| Cmax | umol/L | 29.3 | 29.2 |
| Clearance | mL/kg/min | 0.09 | 0.13 |
| DN AUC | umol/L*hr | 426 | 407 |
| Vss | mL/kg | 165 | 187 |

Example 31

A BRCA1/2 Mutant Model is Ultra-Sensitive to Pt(IV)M Monomaleimide Compounds

Figure 30:
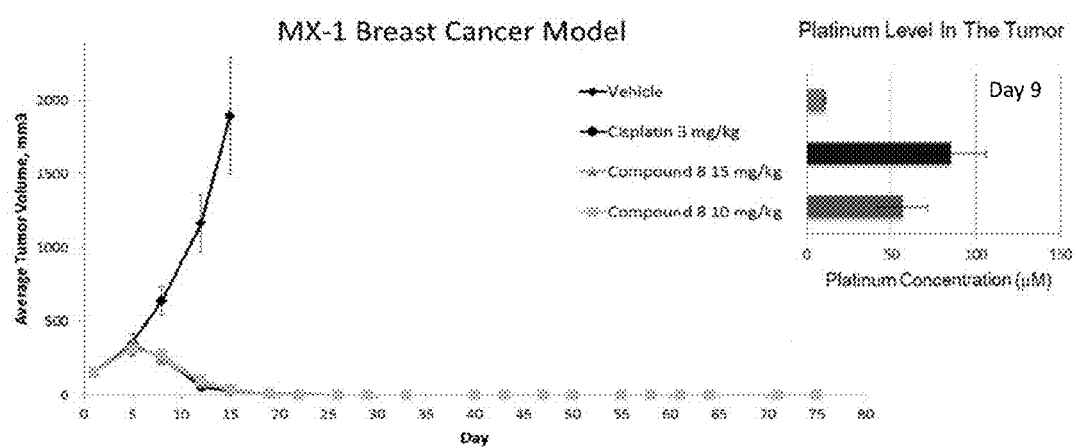
FIG. 30 shows average tumor volumes and platinum levels in the tumors in MX-1 breast cancer model treated with cisplatin and a Pt(IV)M monomaleimide compound.

In vivo MX-1 human breast cancer xenograft studies were carried out with cisplatin and a Pt(IV)M monomaleimide compound. Tumor volumes of MX-1 induced xenografts in mice were measured after multiple intravenous doses of compound 8 at 15 mg/kg at day 1, day 5, day 8 and day 12 (two times per week for two weeks) for the main study group. Compound 8 at 10 mg/kg and cisplatin at 3 mg/kg were also tested with the same dosing days. MX-1 cell line is estrogen receptor negative and Her2 normal. It is BRCA1 and BRCA2 mutant: BRCA1 truncating mutation (3363delGAAA) and BRCA2 mutations (16864A>C, Asn289His, and 22184A>G, Asn991Asp). Satellite groups (n=5) were collected on Day 9 for platinum tumor measurements. Average tumor volumes and platinum levels in the tumors were shown in FIG. 30. Tumor disappeared at day 12 after treatment with compound 8. Additionally, no tumor regrowth was observed for the 15 mg/kg group at end of study, Day 75 which was also seen with the cisplatin treated group. Only one tumor from the 10 mg/kg group began to grow back at on Day 71, with a volume of 39 mm$^3$ at end of study, Day 75. Compound 8 also delivered higher concentrations of platinum to the tumor than cisplatin.

TABLE 10

| Treatment | TGI % at Day 12 | pValue |
|---|---|---|
| Cisplatin (3 mg/kg) | 95.1 | p < 0.05 |
| Compound 8 (10 mg/kg) | 91.3 | p < 0.05 |
| Compound 8 (15 mg/kg) | 93.3 | p < 0.05 |

Example 32

Rat Toxicology Studies for Pt(IV)M Monomaleimide Compounds

Figure 31:
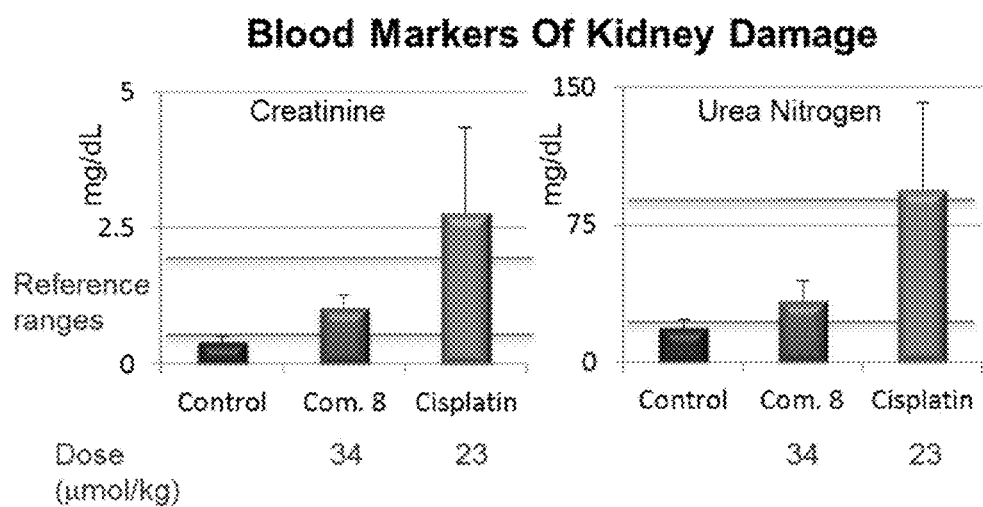
FIG. 31 shows levels of blood markers of kidney damage after treatments with cisplatin and a Pt(IV)M monomaleimide compound.

Compound 8 was evaluated in a rat toxicology study. Tubular necrosis values were shown in Table 11. Creatinine and urea nitrogen levels were shown in FIG. 31. Blood markers and histopathology showed an improvement in kidney toxicity compared to cisplatin at a higher dose of platinum. No other histopathology findings of compound 8 were observed.

TABLE 11

Kidney histopathology of cisplatin and compound 8

|  | Dose (umol/kg) | Tubular necrosis |
|---|---|---|
| Cisplatin | 23 | 2.3 |
| Compound 8 | 17 | 0 |
| Compound 8 | 34 | 1.3 |

Example 33

Effect of Pt(IV)M Monomaleimide Compounds on Colorectal Tumor Growth In Vitro and In Vivo A colorectal cancer cell line, e.g., HCT-15, LoVo, SW48, SW480, HCT 116, HT115, HT29, HCA-7, etc., is plated in 96 well plates (Costar) and 24 hours later are treated with Compound 5 for 48-72 hours. Compound 5 starting dose is 20 µM and three-fold serial dilutions are done for a total of ten points Inhibition of cell proliferation is measured using CellTiter-Glo® reagent using the standard protocol (Promega) and a Glomax® multi+detection system (Promega). Percent proliferation inhibition is calculated using the following formula: % inhibition=(control-treatment)/control*100. Control is defined as vehicle alone.

The ability of compound 5 to affect the growth of human colorectal cancer and colorectal cancer xenografts is tested. All mice are treated in accordance with the OLAW Public Health Service Policy on Human Care and Use of Laboratory Animals and the ILAR Guide for the Care and Use of Laboratory Animals. All in vivo studies are conducted following the protocols approved by the Charles River Institutional Animal Care and Use Committee. Colorectal cancer is induced in 10 week old mice. When tumors approach a volume of 100 mm$^3$, mice are randomized into three groups of ten animals. Mice are treated with vehicle control (10% Solutol® HS15 in saline) or compound 5 at a dose of 10 mg/kg-30 mg/kg by intravenous injection. Mice are dosed twice weekly for the duration of the study. Twenty-four hours after the final dose tumor volumes are measured again for calculation of tumor growth inhibition. All statistical analyses are performed using GraphPad PRISM® Version 6.00. Final tumor volumes are analyzed using with a one-way analysis of variance and Tukey multiple comparison test. It is observed that compound 5 inhibited tumor growth.

Equivalents and Scope

While several embodiments of the present teachings have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present teachings. More generally, those skilled in the art will appreciate that all parameters, dimensions, materials, and configurations described herein are meant to be exemplary and that the actual parameters, dimensions, materials, and/or configurations will depend upon the specific application or applications for which the teachings of the present teachings is/are used. Those skilled in the art will recognize, or be able to ascertain using no more than routine experimentation, many equivalents to the specific embodiments of the present teachings described herein.

It is, therefore, to be understood that the foregoing embodiments are presented by way of example only and that, within the scope of the appended claims and equivalents thereto, the present teachings may be practiced otherwise than as specifically described and claimed. The present teachings are directed to each individual feature and/or method described herein. In addition, any combination of two or more such features and/or methods, if such features and/or methods are not mutually inconsistent, is included within the scope of the present teachings.

The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

What is claimed is:

1. A compound of Formula IIb:

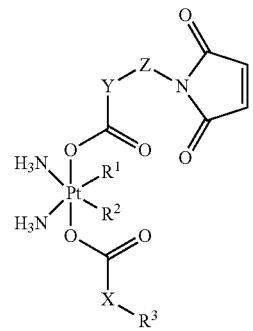

or a pharmaceutically acceptable salt thereof, wherein:

X and Y are independently selected from NH, alkyl and aryl;

$R^1$ and $R^2$ each is Cl, or $R^1$ and $R^2$ are joined to form an oxalate;

$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, and heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, and heterocyclyl, and Z is alternatively absent, alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine, wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, and heterocyclyl.

2. The compound of claim 1, wherein the compound conjugates with a functional group on a protein, engineered protein, antibody, antibody fragment, peptide, agonist, antagonist, aptamer or ligand which may be capable of recognizing a selected target cell population, and/or derivative/analogy/mimics thereof.

3. The compound of claim 2, wherein the conjugation between the compound and the functional group takes place in vivo.

4. The compound of claim 2, wherein the conjugation between the compound and the functional group is performed prior to administration in vivo.

5. The compound of claim 2, wherein the compound conjugates with a functional group on a protein which is albumin.

6. The compound of claim 1, wherein $R^1$ and $R^2$ each is Cl.

7. The compound of claim 1, wherein $R^1$ and $R^2$ are joined to form an oxalate.

8. The compound of claim 1, wherein $R^3$ is alkyl.

9. The compound of claim 1, wherein $R^3$ is methyl or ethyl.

10. A compound selected from:

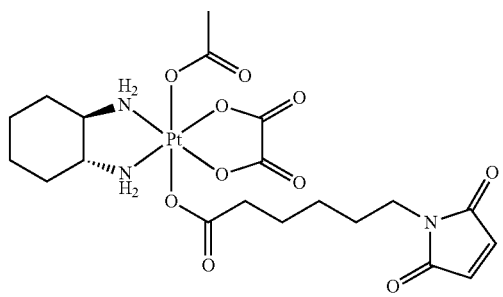

1

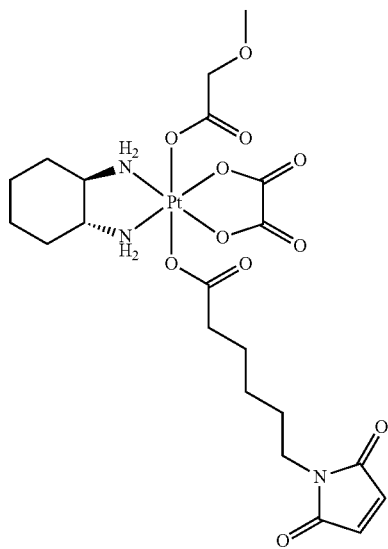

2

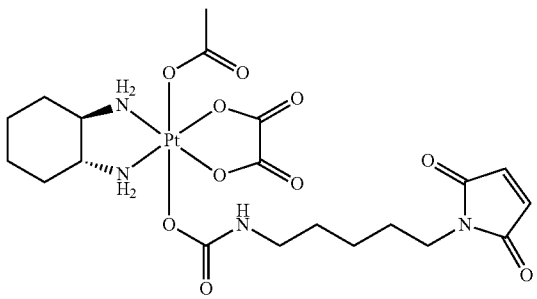

3

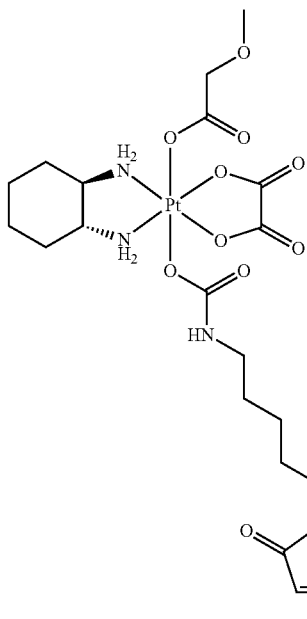

4

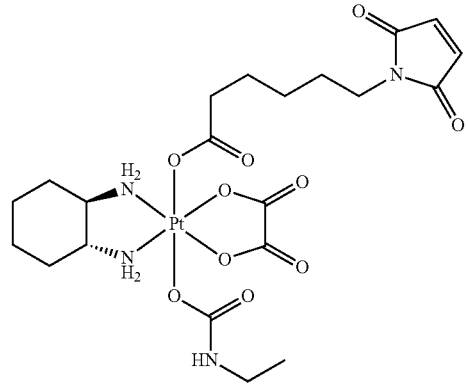

5

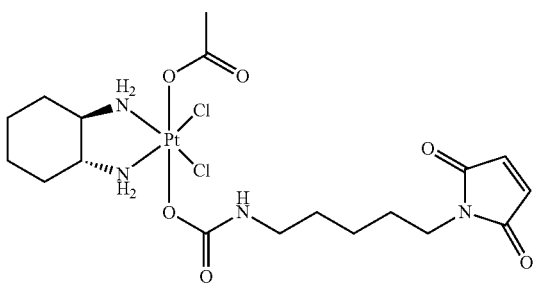

6

7
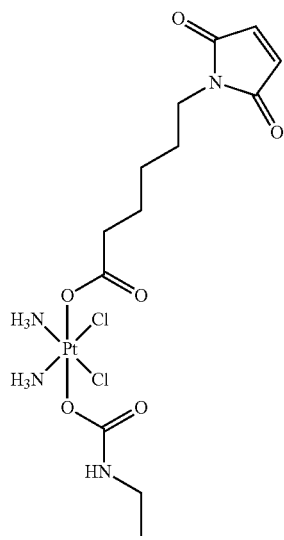
10
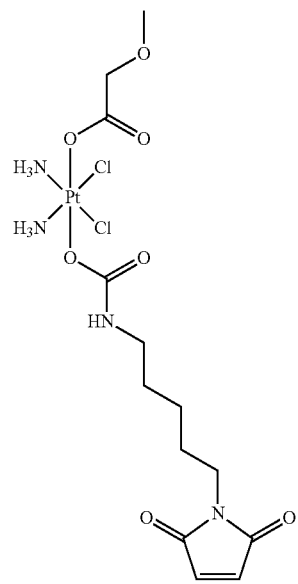
8
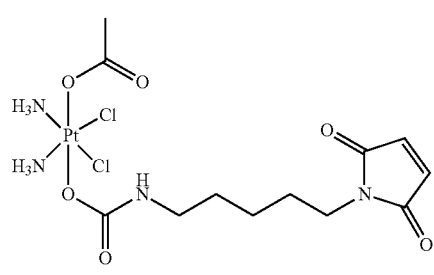
11
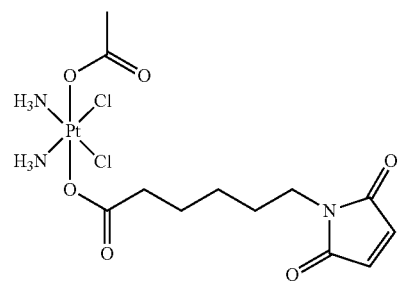
9
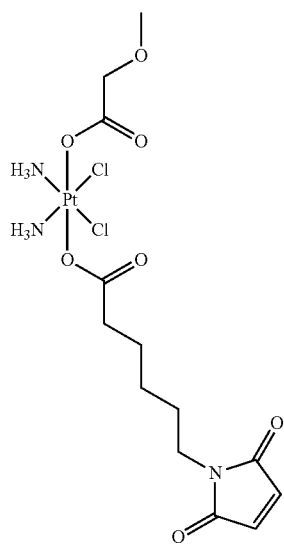
12
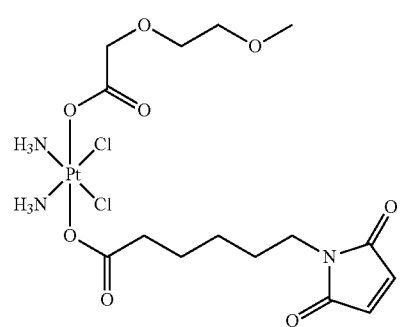

87
-continued
13
14
15
16
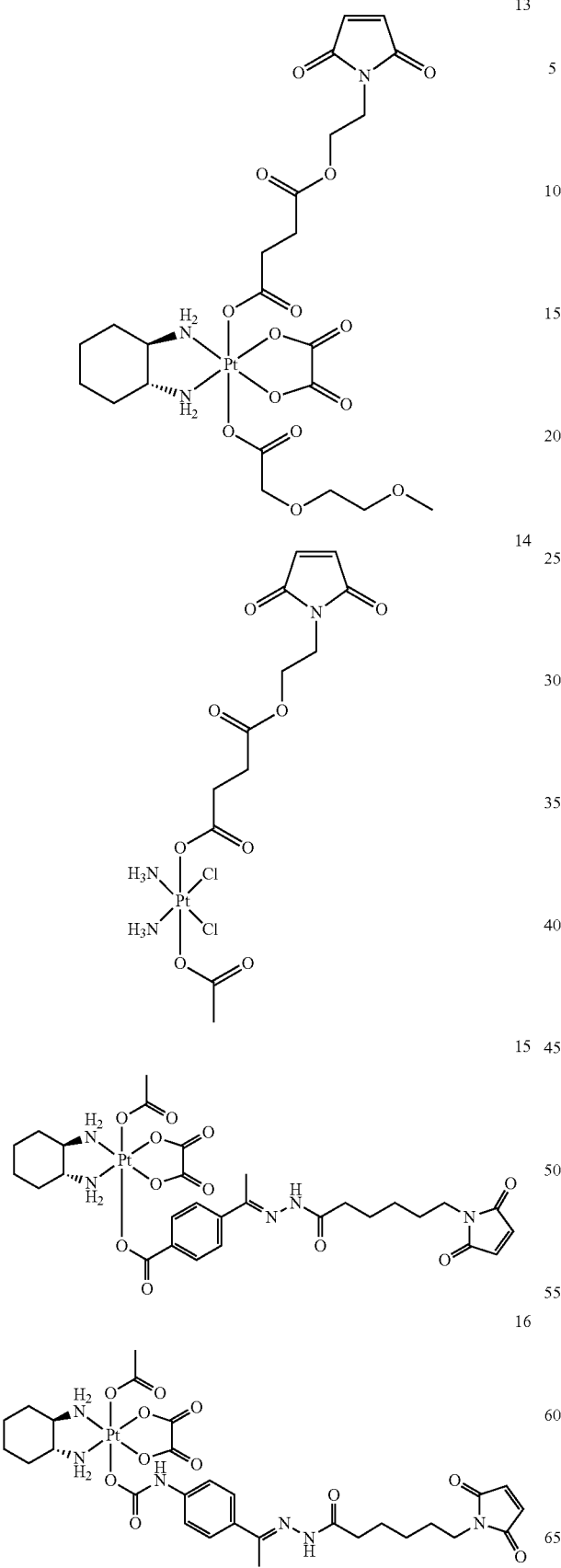
88
-continued
17
18
21
22
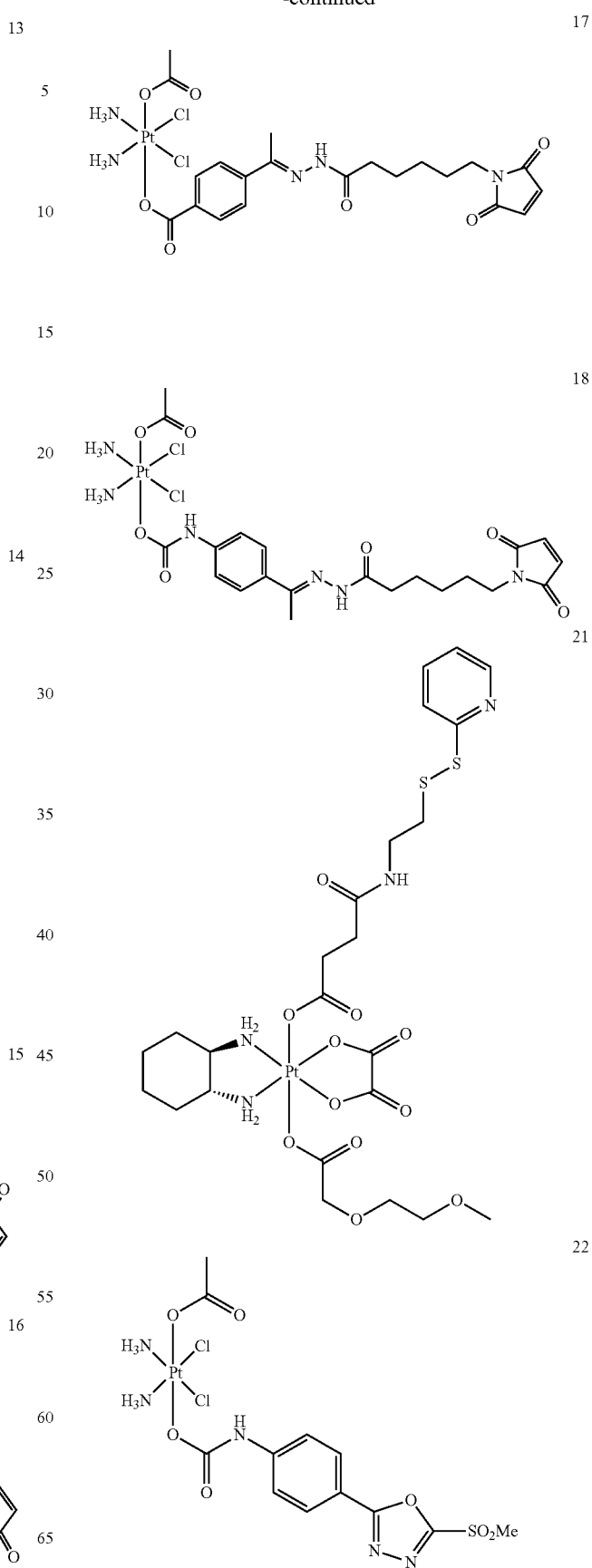

23
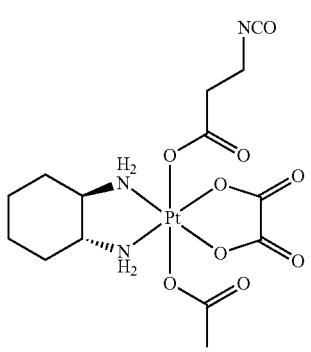
24
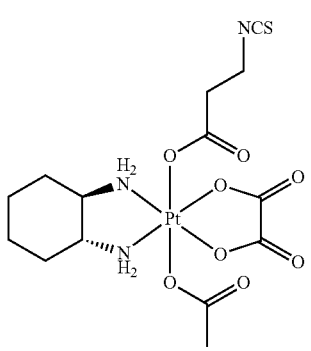
25
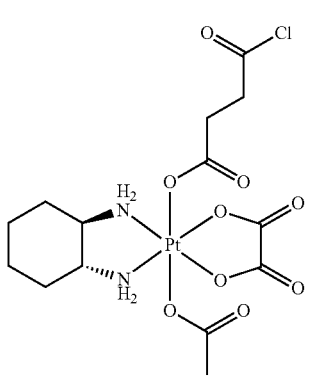
26
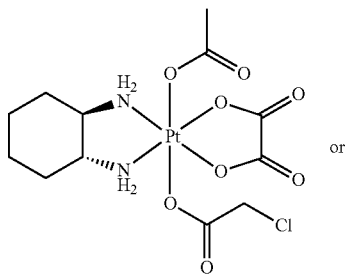
or
27
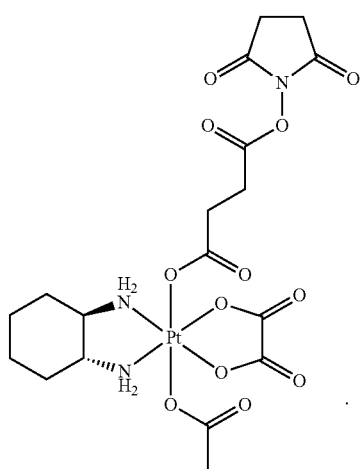
11. A pharmaceutical composition comprising the compound of claim 1 and a pharmaceutically acceptable carrier.
12. A pharmaceutical composition comprising any compound of claim 10 and a pharmaceutically acceptable carrier.
* * * * *